(12) United States Patent
Weiss et al.

(10) Patent No.: US 11,995,839 B2
(45) Date of Patent: *May 28, 2024

(54) AUTOMATED DETECTION, GENERATION AND/OR CORRECTION OF DENTAL FEATURES IN DIGITAL MODELS

(71) Applicant: Align Technology, Inc., San Jose, CA (US)

(72) Inventors: Assaf Weiss, Yavne (IL); Maxim Volgin, Moscow (RU); Pavel Agniashvili, Moscow (RU); Chad Clayton Brown, Cary, NC (US); Alexander Raskhodchikov, Moscow (RU); Avi Kopelman, Palo Alto, CA (US); Michael Sabina, Campbell, CA (US); Moti Ben-Dov, Tel Mond (IL); Shai Farkash, Hod Hasharon (IL); Igor Makiewsky, Ramat Gan (IL); Maayan Moshe, Ramat Hasharon (IL); Ofer Saphier, Rechovot (IL)

(73) Assignee: Align Technology, Inc., San Jose, CA (US)

( * ) Notice: Subject to any disclaimer, the term of this patent is extended or adjusted under 35 U.S.C. 154(b) by 783 days.

This patent is subject to a terminal disclaimer.

(21) Appl. No.: 17/011,930

(22) Filed: Sep. 3, 2020

(65) Prior Publication Data
US 2021/0059796 A1 Mar. 4, 2021

Related U.S. Application Data

(60) Provisional application No. 62/895,905, filed on Sep. 4, 2019.

(51) Int. Cl.
*G06T 7/12* (2017.01)
*A61C 13/00* (2006.01)
(Continued)

(52) U.S. Cl.
CPC ............ *G06T 7/12* (2017.01); *A61C 13/0004* (2013.01); *A61C 13/0019* (2013.01);
(Continued)

(58) Field of Classification Search
None
See application file for complete search history.

(56) References Cited

U.S. PATENT DOCUMENTS 9,760,978 B1 * 9/2017 Lu .............................. G06T 5/50
10,568,722 B2 2/2020 Kopelman et al.
(Continued)

FOREIGN PATENT DOCUMENTS

| CA | 2755555 A1 | 9/2010 |
|---|---|---|
| CN | 109986507 A | 7/2019 |
| WO | 2009006273 A2 | 1/2009 |

*Primary Examiner* — Bion A Shelden
(74) *Attorney, Agent, or Firm* — Lowenstein Sandler LLP

(57) ABSTRACT

Methods and systems are described that mark and/or correct margin lines and/or other features of dental sites. In one example a three-dimensional model of a dental site is generated from intraoral scan data of the dental site, the three-dimensional model comprising a representation of a preparation tooth. An image of the preparation tooth is received or generated. Data from the image is processed using a trained machine learning model that has been trained to identify margin lines of preparation teeth, wherein the trained machine learning model outputs a probability map comprising, for each pixel in the image, a probability that the pixel depicts a margin line. The three-dimensional model of the dental site is then updated by marking the margin line on the representation of the preparation tooth based on the probability map.

20 Claims, 33 Drawing Sheets

(51) Int. Cl.
    *A61C 13/34* (2006.01)
    *G06N 3/047* (2023.01)
    *G06N 3/08* (2023.01)
    *G06T 7/00* (2017.01)
    *G16H 30/40* (2018.01)

(52) U.S. Cl.
    CPC ............. *A61C 13/34* (2013.01); *G06N 3/047* (2023.01); *G06N 3/08* (2013.01); *G06T 7/0012* (2013.01); *G16H 30/40* (2018.01); *G06T 2207/20081* (2013.01); *G06T 2207/20084* (2013.01); *G06T 2207/30036* (2013.01)

(56) References Cited

U.S. PATENT DOCUMENTS

| | | | |
|---|---|---|---|
| 10,932,890 B1* | 3/2021 | Sant | A61C 13/0004 |
| 2004/0015327 A1 | 1/2004 | Sachdeva et al. | |
| 2006/0115793 A1 | 6/2006 | Kopelman et al. | |
| 2007/0100226 A1 | 5/2007 | Yankelevitz et al. | |
| 2009/0136103 A1* | 5/2009 | Sonka | G06V 10/7635 382/128 |
| 2009/0298017 A1 | 12/2009 | Boerjes et al. | |
| 2010/0027865 A1* | 2/2010 | Wels | G06T 7/162 382/131 |
| 2010/0281370 A1* | 11/2010 | Rohaly | G06T 15/205 715/810 |
| 2013/0110469 A1* | 5/2013 | Kopelman | G06T 19/00 703/1 |
| 2013/0243314 A1* | 9/2013 | Civit | G06T 7/11 382/164 |
| 2015/0178908 A1* | 6/2015 | Jesenko | A61C 19/04 433/29 |
| 2016/0256035 A1 | 9/2016 | Kopelman et al. | |
| 2018/0005371 A1 | 1/2018 | Sabina et al. | |
| 2018/0028294 A1* | 2/2018 | Azernikov | G06F 18/24143 |
| 2019/0313963 A1* | 10/2019 | Hillen | G06V 10/764 |
| 2019/0333627 A1* | 10/2019 | Johnson | G06N 3/02 |
| 2020/0170760 A1* | 6/2020 | Dawood | G06T 7/0012 |

* cited by examiner

```
┌─────────────────────────────────────────────────────────────────────────────┐
│ Receive a first intraoral scan of a preparation tooth after a gingival retraction tool has momentarily │
│ retracted a first portion of a gingiva surrounding the preparation tooth to partially expose a finish │
│ line, wherein a first portion of the finish line is exposed in the first intraoral scan 505 │
└─────────────────────────────────────────────────────────────────────────────┘
                                      ▼
┌─────────────────────────────────────────────────────────────────────────────┐
│ Receive a second intraoral scan of the preparation tooth after receiving the first intraoral scan, │
│ wherein the first portion of the finish line is obscured by the first portion of the gingiva in the second │
│ intraoral scan 510 │
└─────────────────────────────────────────────────────────────────────────────┘
                                      ▼
┌─────────────────────────────────────────────────────────────────────────────┐
│        Compare the first intraoral scan to the second intraoral scan 515         │
└─────────────────────────────────────────────────────────────────────────────┘
                                      ▼
┌─────────────────────────────────────────────────────────────────────────────┐
│ Identify, between the first intraoral scan and the second intraoral scan, a conflicting surface at a │
│ region of the preparation tooth corresponding to the first portion of the finish line 520 │
└─────────────────────────────────────────────────────────────────────────────┘
                                      ▼
┌─────────────────────────────────────────────────────────────────────────────┐
│              Determine that conflicting surface satisfies scan selection criteria 522              │
└─────────────────────────────────────────────────────────────────────────────┘
                                      ▼
┌─────────────────────────────────────────────────────────────────────────────┐
│     Discard or mark data for the region of the preparation tooth from the second intraoral scan 525     │
└─────────────────────────────────────────────────────────────────────────────┘
                                      ▼
┌─────────────────────────────────────────────────────────────────────────────┐
│ Stitch together the first intraoral scan and the second intraoral scan to generate a virtual model of │
│ the preparation tooth, wherein data for the region of the preparation tooth from the first intraoral │
│ scan is used to generate the virtual model of the preparation tooth, and wherein data for the region │
│ of the preparation tooth from the second intraoral scan is not used to generate the virtual model of │
│ the preparation tooth 530 │
└─────────────────────────────────────────────────────────────────────────────┘
```

FIG. 5A         ↘ 500

Receive a first intraoral scan of a preparation tooth after a gingival retraction tool has momentarily retracted a first portion of a gingiva surrounding the preparation tooth to partially expose a finish line, wherein a first portion of the finish line is exposed in the first intraoral scan, and wherein a second portion of the finish line is obscured by the gingiva in the first intraoral scan 555

Receive a second intraoral scan of the preparation tooth after the gingival retraction tool has momentarily retracted a second portion of the gingiva surrounding the preparation tooth to partially expose the finish line, wherein the second portion of the finish line is exposed in the second intraoral scan, and wherein the first portion of the finish line is obscured by the gingiva in the second intraoral scan 560

Generate a virtual model of the preparation tooth using the first intraoral scan and the second intraoral scan, wherein the first intraoral scan is used to generate a first region of the virtual model representing the first portion of the finish line, and wherein the second intraoral scan is used to generate a second region of the virtual model representing the second portion of the finish line 565

FIG. 5B   550

```
┌─────────────────────────────────────────────────────────────────────┐
│ Receive a first intraoral scan of a preparation tooth after a      │
│ gingival retraction cord that was packed around the preparation    │
│ tooth was removed to expose a finish line 605                      │
└─────────────────────────────────────────────────────────────────────┘
                                  ▼
┌─────────────────────────────────────────────────────────────────────┐
│ Generate a first surface for the preparation tooth using the first │
│ intraoral scan data and a first one or more algorithms 610         │
└─────────────────────────────────────────────────────────────────────┘
                                  ▼
┌─────────────────────────────────────────────────────────────────────┐
│ Determine whether, for a portion of the first surface depicting a  │
│ portion of the preparation tooth, the finish line is obscured by   │
│ gum tissue 615                                                     │
└─────────────────────────────────────────────────────────────────────┘
                                  ▼
```

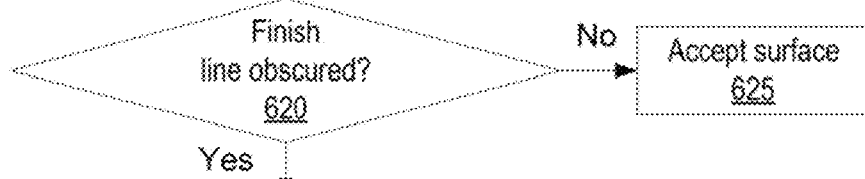

```
┌─────────────────────────────────────────────────────────────────────┐
│ Generate a second surface for the portion of the preparation tooth │
│ in which the finish line was obscured by the gingiva using the     │
│ first intraoral scan data and a second one or more algorithms 630  │
└─────────────────────────────────────────────────────────────────────┘
                                  ▼
┌─────────────────────────────────────────────────────────────────────┐
│ Determine whether, for the second surface depicting the portion of │
│ the preparation tooth, the finish line is obscured by gum tissue   │
│ 635                                                                │
└─────────────────────────────────────────────────────────────────────┘
                                  ▼
```

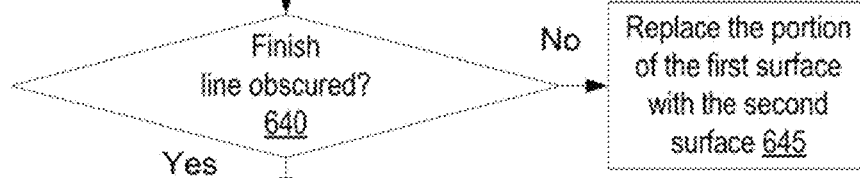

```
┌─────────────────────────────────────────────────────────────────────┐
│ Receive second intraoral scan data in which the finish line is     │
│ exposed at the portion of the preparation tooth 650                │
└─────────────────────────────────────────────────────────────────────┘
                                  ▼
┌─────────────────────────────────────────────────────────────────────┐
│ Generate a third surface for the portion of the preparation tooth  │
│ using the second intraoral scan data and the second one or more    │
│ algorithms 655                                                     │
└─────────────────────────────────────────────────────────────────────┘
                                  ▼
┌─────────────────────────────────────────────────────────────────────┐
│ Replace the portion of the first surface with the third surface 660│
└─────────────────────────────────────────────────────────────────────┘
```

FIG. 6A  600

Receive a plurality of intraoral scans of a preparation tooth comprising a finish line that underlies a gingiva, wherein at least a portion of the finish line is not shown in the plurality of intraoral scans 710

Receive at least one of a cone-beam computed tomography (CBCT) scan, an optical coherence tomography (OCT) scan, or an ultrasound scan of the preparation tooth, wherein the finish line is shown in at least one of the CBCT scan, the OCT scan or the ultrasound scan 715

Process the CBCT scan, the OCT scan or the ultrasound scan to identify a) the preparation tooth, b) the gingiva and c) the finish line 720

Generate a virtual three-dimensional model of the preparation tooth using the plurality of intraoral scans and at least one of the CBCT scan, the OCT scan, or the ultrasound scan, wherein at least one of the CBCT scan, the OBT scan or the ultrasound scan is used to depict the finish line in the virtual three-dimensional model 725

FIG. 7A  700

Merge together data from the plurality of intraoral scans to form a preliminary virtual three-dimensional model of the preparation tooth, wherein the finish line is covered by the gingiva in the preliminary virtual three-dimensional model 732

Merge data from the CBCT scan, the OCT scan or the ultrasound scan with the preliminary virtual three-dimensional model to generate a three-dimensional virtual model 734

Determine locations of the finish line from the CBCT scan, the OCT scan, or the ultrasound scan 736

Remove a gingival surface that overlies the finish line from the preliminary virtual three-dimensional model 738

Replace the removed gingival surface with a surface of the preparation tooth as depicted in the CBCT scan, the OCT scan or the ultrasound scan 740

AUTOMATED DETECTION, GENERATION AND/OR CORRECTION OF DENTAL FEATURES IN DIGITAL MODELS

RELATED APPLICATIONS

This patent application claims the benefit under 35 U.S.C. § 119(e) of U.S. Provisional Application No. 62/895,905, filed Sep. 4, 2019.

TECHNICAL FIELD

Embodiments of the present disclosure relate to the field of dentistry and, in particular, to the use of machine learning and other processing techniques to identify, generate and/or correct margin lines and/or other dental features in digital models.

BACKGROUND

For restorative dental work such as crowns and bridges, one or more intraoral scans may be generated of a preparation tooth and/or surrounding teeth on a patient's dental arch using an intraoral scanner. In cases of sub-gingival preparations, the gingiva covers at least portions of the margin line (also referred to herein as a finish line) and is retracted in order to fully expose the margin line. Thus, intraoral scans are generally created after a doctor packs a dental retraction cord (also referred to as packing cord or retraction cord) under the gums around the preparation tooth and then withdraws the retraction cord, briefly exposing a sub-gingival margin line. The process of packing the retraction cord between the preparation and the gums is lengthy, and can take about 10 minutes per preparation to complete. Additionally, this process is painful to the patient and can damage the gum. The intraoral scans taken after the retraction cord has been packed around the preparation tooth and then withdrawn must be taken within a narrow time window during which the gingiva collapses back over the margin line. If insufficient intraoral scans are generated before the gingiva collapses, then the process needs to be repeated. Once sufficient intraoral scans are generated, these are then used to generate a virtual three-dimensional (3D) model of a dental site including the preparation tooth and the surrounding teeth and gingiva. For example, a virtual 3D model of a patient's dental arch may be generated. The virtual 3D model may then be sent to a lab.

The lab may then perform a process called modeling in which it manually manipulates the virtual 3D model or a physical 3D model generated from the virtual 3D model to achieve a 3D model that is usable to create a crown, bridge, or other dental prosthetic. This may include manually marking a margin line in the virtual 3D model or the physical 3D model, for example. This may further include resculpting the virtual 3D model or physical 3D model, such as to correct the margin line if it is unclear or covered by gingiva in areas. Such work of modifying the virtual 3D model and/or the physical 3D model by the lab often results in an educated guess at what the actual geometry of the patient's preparation tooth is, including a guess at the margin line, a guess at the tooth's shape, and so on. A dental prosthetic may then be manufactured using the modified virtual 3D model or physical 3D model. If the guess at the true geometry of the patient's preparation tooth was incorrect, then this process is repeated, resulting in additional work on the part of the dentist and/or lab. Additionally, the process of manually modifying the virtual 3D model or physical 3D model is a time intensive task that is performed by experienced lab technicians, which increases the overall cost of the dental prosthetic and increases the amount of time that it takes to manufacture the dental prosthetic.

SUMMARY

In a first aspect of the disclosure, a method includes generating a three-dimensional model of a dental site from scan data of the dental site, the three-dimensional model comprising a representation of a preparation tooth. The method further includes receiving or generating an image of the preparation tooth, the image comprising a height map. The method further includes processing data from the image using a trained machine learning model that has been trained to identify margin lines of preparation teeth, wherein the trained machine learning model outputs a probability map comprising, for each pixel in the image, a probability that the pixel depicts a margin line. The method further includes updating the three-dimensional model of the dental site by marking the margin line on the representation of the preparation tooth based on the probability map.

A second aspect of the disclosure may further extend the first aspect of the disclosure. In the second aspect of the disclosure, the image of the preparation tooth is generated by projecting at least a portion of the three-dimensional model onto a two-dimensional surface. A third aspect of the disclosure may further extend the first or second aspects of the disclosure. In the third aspect of the disclosure, the scan data is intraoral scan data, and the image of the preparation tooth is an intraoral image included in the intraoral scan data.

A fourth aspect of the disclosure may further extend the first through third aspects of the disclosure. In the fourth aspect of the disclosure, the method further includes determining, for each point of a plurality of points on the three-dimensional model that maps to a pixel in the image of the preparation tooth, a probability that the point depicts the margin line using the probability map. Additionally, the method further includes computing the margin line by applying a cost function to the plurality of points on the three-dimensional model, wherein the cost function selects points that together form a contour having a combined minimal cost, wherein for each point a cost of the point is related to an inverse of the probability that the point depicts the margin line. A fifth aspect of the disclosure may further extend the fourth aspect of the disclosure. In the fifth aspect of the disclosure, the method further includes determining whether the combined minimal cost exceeds a cost threshold, and responsive to determining that the combined minimal cost exceeds the cost threshold, determining that the computed margin line has an unacceptable level of uncertainty.

A sixth aspect of the disclosure may further extend the fourth aspect of the disclosure. In the sixth aspect of the disclosure, the method further includes computing separate costs for different segments of the computed margin line, determining that a segment of the computed margin line has a cost that exceeds a cost threshold, and determining that the segment of the computed margin line has an unacceptable level of uncertainty. A seventh aspect of the disclosure may further extend the sixth aspect of the disclosure. In the seventh aspect of the disclosure, the method further includes highlighting the segment of the computed margin line having the unacceptable level of uncertainty in the three-dimensional model.

An eighth aspect of the disclosure may further extend the sixth aspect of the disclosure. In the eighth aspect of the disclosure, the method further includes locking regions of the three-dimensional model comprising segments of the computed margin line having acceptable levels of uncertainty, receiving a new intraoral image depicting the segment of the computed margin line with the unacceptable level of uncertainty, and updating the three-dimensional model using the new intraoral image to output an updated three-dimensional model, wherein a first region comprising the segment of the computed margin line with the unacceptable level of uncertainty is replaced using information from the new intraoral image, and wherein locked regions of the three-dimensional model comprising the segments of the computed margin line having the acceptable levels of uncertainty are unchanged during the updating.

A ninth aspect of the disclosure may further extend the eighth aspect of the disclosure. In the ninth aspect of the disclosure, the scan data comprises a plurality of blended images of the dental site, wherein each blended image of the plurality of blended images is based on a combination of a plurality of images. Additionally, receiving the new intraoral image comprises accessing a plurality of individual intraoral images used to generate at least some of the plurality of blended images, identifying a subset of the plurality of individual intraoral images that depict the segment of the computed margin line, and selecting the new intraoral image from the subset of the plurality of individual intraoral images, wherein the new intraoral image comprises an improved depiction of the margin line as compared to the image of the preparation tooth. A tenth aspect of the disclosure may further extend the ninth aspect of the disclosure. In the tenth aspect of the disclosure, the method further includes generating a plurality of different versions of the updated three-dimensional model, wherein each of the plurality of different versions is based on a different individual intraoral image from the subset of the plurality of individual intraoral images, and receiving a user selection of a particular version of the updated three-dimensional model corresponding to the new intraoral image.

An eleventh aspect of the disclosure may further extend the eighth aspect of the disclosure. In the eleventh aspect of the disclosure, the method further includes generating a projected image of the first region by projecting at least a portion of the updated three-dimensional model onto an additional two-dimensional surface, the projected image comprising an additional height map, processing data from the projected image using the trained machine learning model, wherein the trained machine learning model outputs an additional probability map comprising, for each pixel in the projected image, a probability that the pixel depicts the margin line, and further updating the updated three-dimensional model of the dental site by marking the margin line in the first region based on the additional probability map.

A $12^{th}$ aspect of the disclosure may further extend the first through eleventh aspects of the disclosure. In the $12^{th}$ aspect of the disclosure, the trained machine learning model further outputs an indication for at least a section of the margin line as to whether the section of the margin line depicted in the image is a high quality margin line or a low quality margin line. A $13^{th}$ aspect of the disclosure may further extend the first through $12^{th}$ aspects of the disclosure. In the $13^{th}$ aspect of the disclosure, the method further includes determining that the margin line is indeterminate in at least one section of the margin line associated with the image, processing data from the image or a new image generated from the three-dimensional model using a second trained machine learning model that has been trained to modify images of teeth, wherein the second trained machine learning model outputs a modified image comprising a modified height map, and updating the three-dimensional model of the dental site using the modified height map, wherein an updated three-dimensional model comprises an updated margin line with an increased level of accuracy.

A $14^{th}$ aspect of the disclosure may further extend the $13^{th}$ aspect of the disclosure. In the $14^{th}$ aspect of the disclosure, the modified image comprises a plurality of pixels that are identified as part of the margin line. A 15th aspect of the disclosure may further extend the $13^{th}$ aspect of the disclosure. In the $15^{th}$ aspect of the disclosure, the image comprises a depiction of an interfering surface that obscures the margin line, wherein at least a portion of the depiction of the interfering surface is removed in the modified image, and wherein a portion of the margin line that was obscured in the image is shown in the modified image. A $16^{th}$ aspect of the disclosure may further extend the $15^{th}$ aspect of the disclosure. In the $16^{th}$ aspect of the disclosure, the interfering surface comprises at least one of blood, saliva, soft tissue or a retraction material. A $17^{th}$ aspect of the disclosure may further extend the first through $16^{th}$ aspects of the disclosure. In the $17^{th}$ aspect of the disclosure, the image is a monochrome image, and an input to the machine learning model that initiates the processing of the image comprises data from the image and additional data from a two-dimensional color image that lacks a height map.

In an $18^{th}$ aspect of the disclosure, a method includes detecting a margin line in a three-dimensional model of a preparation tooth from one or more images of the preparation tooth, wherein each of the one or more images comprises a height map; determining, for each segment of a plurality of segments of the margin line, a quality score for the segment; determining whether any of the plurality of segments of the margin line has a quality score that is below a quality threshold; and responsive to determining that a segment of the margin line has a quality score that is below the quality threshold, updating the three-dimensional model of the preparation tooth by replacing a portion of the three-dimensional model associated with the segment of the margin line with image data from a new image.

A $19^{th}$ aspect of the disclosure may further extend the $18^{th}$ aspect of the disclosure. In the $19^{th}$ aspect of the disclosure, the method further includes prompting a user to generate a new intraoral image depicting the segment of the margin line, and receiving the new image, the new image having been generated by an intraoral scanner responsive to prompting the user to generate the new intraoral image. A $20^{th}$ aspect of the disclosure may further extend the $18^{th}$ or $19^{th}$ aspect of the disclosure. In the $20^{th}$ aspect of the disclosure, the method further includes locking portions of the three-dimensional model comprising segments of the margin line having quality scores that meet or exceed the quality threshold, and erasing the portion of the three-dimensional model associated with the segment of the margin line prior to replacing the portion of the three-dimensional model with the image data from the new image. The locked portions of the three-dimensional model may include the segments of the margin line having quality scores that meet or exceed the quality threshold are unchanged during the updating.

A $21^{st}$ aspect of the disclosure may further extend the $18^{th}$ through $20^{th}$ aspect of the disclosure. In the $21^{st}$ aspect of the disclosure, detecting the margin line comprises: processing data from each of the one or more images using a trained machine learning model that has been trained to identify margin lines of preparation teeth, wherein for each image the trained machine learning model outputs a probability map comprising, for each pixel in the image, a probability that the pixel depicts a margin line; and determining, for each of a plurality of points of the three-dimensional model, a probability that the point depicts the margin line using the probability map of one or more of the plurality of images. A $22^{nd}$ aspect of the disclosure may further extend the $21^{st}$ aspect of the disclosure. In the $22^{nd}$ aspect of the disclosure, detecting the margin line further comprises computing the margin line by applying a cost function to the plurality of points on the three-dimensional model, wherein the cost function selects points that together form a contour having a combined minimal cost, wherein for each point a cost of the point is related to an inverse of the probability that the point depicts the margin line. A $23^{rd}$ aspect of the disclosure may further extend the $22^{nd}$ aspect of the disclosure. In the $23^{rd}$ aspect of the disclosure, determining the quality score for each segment comprises computing a separate cost for each segment of the margin line using the cost function.

A $24^{th}$ aspect of the disclosure may further extend the $18^{th}$ through $23^{rd}$ aspect of the disclosure. In the $24^{th}$ aspect of the disclosure, the method further includes generating the three-dimensional model from scan data comprising a plurality of blended images, wherein each blended image of the plurality of blended images is based on a combination of a plurality of individual intraoral images generated by an intraoral scanner, accessing the plurality of individual intraoral images used to generate at least some of the plurality of blended images, identifying a subset of the plurality of individual intraoral images that depict the segment of the margin line, and selecting the new image from the subset of the plurality of individual intraoral images, wherein the new image comprises an improved depiction of the segment of the margin line as compared to a depiction of the segment of the margin line from the scan data. A $125^{th}$ aspect of the disclosure may further extend the $24^{th}$ aspect of the disclosure. In the $25^{th}$ aspect of the disclosure, the method further includes generating a plurality of different updated versions of the three-dimensional model, wherein each of the plurality of different updated versions is based on a different individual intraoral image from the subset of the plurality of individual intraoral images, and receiving a user selection of a particular updated version of the three-dimensional model corresponding to the new image.

A $26^{th}$ aspect of the disclosure may further extend the $18^{th}$ through $25^{th}$ aspect of the disclosure. In the $26^{th}$ aspect of the disclosure, the method further includes projecting a portion of the three-dimensional model onto a two-dimensional surface to generate a projected image depicting the segment of the margin line having the quality score that is below the quality threshold, the projected image comprising an additional height map, and processing data from the projected image using a trained machine learning model that has been trained to modify images of teeth, wherein the trained machine learning model outputs data for the new image, wherein the new image is a modified version of the projected image that comprises a modified height map.

A $27^{th}$ aspect of the disclosure may further extend the $26^{th}$ aspect of the disclosure. In the $27^{th}$ aspect of the disclosure, the image comprises a depiction of an interfering surface that obscures the margin line, wherein at least a portion of the depiction of the interfering surface is removed in the modified image, and wherein a portion of the margin line that was obscured in the image is shown in the modified image. A $28^{th}$ aspect of the disclosure may further extend the $26^{th}$ aspect of the disclosure. In the $28^{th}$ aspect of the disclosure, the new image comprises a fabricated version of the segment of the margin line.

A $29^{th}$ aspect of the disclosure may further extend the $86^{th}$ aspect of the disclosure. In the $29^{th}$ aspect of the disclosure, the three-dimensional model is generated from scan data comprising a plurality of blended images, wherein each blended image of the plurality of blended images is based on a combination of a plurality of individual intraoral images generated by an intraoral scanner. Additionally, the method further includes accessing the plurality of individual intraoral images used to generate at least some of the plurality of blended images, identifying a subset of the plurality of individual intraoral images that depict the segment of the margin line, determining a particular image from the subset of the plurality of individual intraoral images comprising a representation of the segment of the margin line that is most similar to the fabricated version of the segment of the margin line, and updating the three-dimensional model of the preparation tooth by replacing the portion of the three-dimensional model associated with the segment of the margin line with image data from the particular image.

In a $30^{th}$ aspect of the disclosure, a method includes generating a three-dimensional model of a dental site from scan data of the dental site, the three-dimensional model comprising a representation of a tooth, wherein a portion of the three-dimensional model comprises an interfering surface that obscures a portion of the tooth; receiving or generating an image of the tooth, the image comprising a height map, wherein the image depicts the interfering surface; processing the image to generate a modified image, wherein the modified image comprises a modified height map, and wherein the portion of the tooth that was obscured by the interfering surface in the image is shown in the modified image; and updating the three-dimensional model of the dental site by replacing, using the modified image comprising the modified height map, the portion of the three-dimensional model that comprises the interfering surface that obscures the portion of the tooth, wherein the portion of the tooth that was obscured in the three-dimensional model is shown in an updated three-dimensional model.

A $31^{st}$ aspect of the disclosure may further extend the $30^{th}$ aspect of the disclosure. In the $31^{st}$ aspect of the disclosure, processing the image comprises inputting data from the image into a trained machine learning model that has been trained to modify images of teeth, wherein the trained machine learning model outputs data for the modified image. A $32^{nd}$ aspect of the disclosure may further extend the $31^{st}$ aspect of the disclosure. In the $32^{nd}$ aspect of the disclosure, an input to the machine learning model comprises data from the image and at least one of a first identifier of a dental practitioner that generated the scan data or a second identifier of a laboratory that will manufacture a dental prosthetic from the updated three-dimensional model. A $33^{rd}$ aspect of the disclosure may further extend the $31^{st}$ or $32^{nd}$ aspect of the disclosure. In the $33^{rd}$ aspect of the disclosure, the image is a monochrome image, and wherein an input to the machine learning model comprises first data from the image and second data from a two-dimensional color image that lacks a height map.

A $34^{th}$ aspect of the disclosure may further extend the $30^{th}$ through $33^{rd}$ aspect of the disclosure. In the $34^{th}$ aspect of the disclosure, the method further includes displaying the updated three-dimensional model, receiving an indication that the updated three-dimensional model does not comprise an accurate depiction of the tooth, receiving one or more new intraoral images generated by an intraoral scanner, and updating the three-dimensional model using the one or more new intraoral images. A 35$^{th}$ aspect of the disclosure may further extend the 30th through 34$^{th}$ aspect of the disclosure. In the 35$^{th}$ aspect of the disclosure, the tooth is a preparation tooth comprising a margin line, the interfering surface obscures a segment of the margin line, the segment of the margin line that was obscured by the interfering surface in the image is shown in the modified image, and the segment of the margin line that was obscured in the three-dimensional model is shown in an updated three-dimensional model.

In a 36$^{th}$ aspect of the disclosure, a method includes receiving scan data comprising a plurality of images of at least a first dental site and a second dental site, wherein each of the plurality of images comprises a time stamp and a height map; determining a first subset of the plurality of images to use for the first dental site, wherein the first subset is determined based at least in part on a) time stamps of images in the first subset and b) geometrical data of the images in the first subset; determining a second subset of the plurality of images to use for the second dental site, wherein the second subset is determined based at least in part on a) time stamps of images in the second subset and b) geometrical data of the images in the second subset; and generating a three-dimensional model of at least a portion of a dental arch, the three-dimensional model comprising a representation of the first dental site generated using the first subset and a representation of the second dental site generated using the second subset.

A 37$^{th}$ aspect of the disclosure may further extend the 36$^{th}$ aspect of the disclosure. In the 37$^{th}$ aspect of the disclosure, the method further includes, for each image of the plurality of intraoral images, inputting data from the image and the time stamp associated with the image into a machine learning model trained to select images for use in generating representations of three-dimensional models of dental sites, wherein for each image the machine learning model outputs a first score associated with the first dental site and a second score associated with the second dental site. Each image in the first subset has a first score that exceeds a threshold, and each image in the second subset has a second score that exceeds the threshold.

A 38$^{th}$ aspect of the disclosure may further extend the 36$^{th}$ or 37$^{th}$ aspect of the disclosure. In the 38th aspect of the disclosure, each of the plurality of images is a blended image that is based on a combination of a plurality of individual intraoral images generated by an intraoral scanner. Additionally, the method further includes identifying a region of the first dental site that is unclear in the three-dimensional model, accessing the plurality of individual intraoral images used to generate at least some of the plurality of blended images, identifying a subset of the plurality of individual intraoral images that depict the region that is unclear, selecting a particular image from the subset of the plurality of individual intraoral images, wherein the particular image comprises an improved depiction of the region, and updating the three-dimensional model using the particular image.

A 39$^{th}$ aspect of the disclosure may further extend the 38$^{th}$ aspect of the disclosure. In the 39$^{th}$ aspect of the disclosure, the method further includes generating a plurality of different versions of the updated three-dimensional model, wherein each of the plurality of different versions is based on a different individual intraoral image from the subset of the plurality of individual intraoral images, and receiving a user selection of a particular version of the updated three-dimensional model.

In a 40$^{th}$ aspect of the disclosure, a method includes receiving a first plurality of intraoral scans of a dental arch while an intraoral scanning application is in a first scanning mode; processing the first plurality of intraoral scans using one or more algorithms configured to determine a three-dimensional surface of a static dental site while the intraoral scanning application is in the first scanning mode; determining, by a processing device, that a partial retraction scan of a first preparation tooth will be performed or has been performed, wherein the partial retraction scan comprises an intraoral scan of a preparation tooth that has not been packed with a gingival retraction cord; activating a partial retraction intraoral scanning mode; receiving a second plurality of intraoral scans; and processing the second plurality of intraoral scans using one or more algorithms configured to determine a three-dimensional surface of a non-static dental site comprising a collapsing gingiva while the intraoral scanning application is in the partial retraction intraoral scanning mode.

A 41$^{st}$ aspect of the disclosure may further extend the 40$^{th}$ aspect of the disclosure. In the 41$^{st}$ aspect of the disclosure, determining that the partial retraction scan will be performed or has been performed comprises receiving an indication based on user input.

A 42$^{nd}$ aspect of the disclosure may further extend the 40$^{th}$ or 41$^{st}$ aspect of the disclosure. In the 42$^{nd}$ aspect of the disclosure, the second plurality of intraoral scans is received prior to determining that the partial retraction scan will be performed or has been performed, the determining comprising automatically determining that the partial retraction scan has been performed based on an analysis of data from one or more of the second plurality of intraoral scans.

A 43$^{rd}$ aspect of the disclosure may further extend the 40$^{th}$ through the 42$^{nd}$ aspect of the disclosure. In the 43$^{rd}$ aspect of the disclosure, processing the second plurality of intraoral scans using the one or more algorithms configured to determine the three-dimensional surface of a non-static dental site comprises: determining a conflicting surface for a pair of intraoral scans from the second plurality of intraoral scans, wherein a first intraoral scan of the pair of intraoral scans has a first distance from a probe of an intraoral scanner for the conflicting surface and a second intraoral scan of the pair of intraoral scans has a second distance from the probe of the intraoral scanner for the conflicting surface; determining that the first distance is greater than the second distance; determining whether a difference between the first distance and the second distance is greater than a difference threshold; responsive to determining that the difference is greater than the difference threshold, discarding a representation of the conflicting surface from the first intraoral scan; and determining a surface of the non-static dental site by combining data from the first intraoral scan and the second intraoral scan, wherein the discarded representation of the conflicting surface from the first intraoral scan is not used to determine the surface.

A 44$^{th}$ aspect of the disclosure may further extend the 43$^{rd}$ aspect of the disclosure. In the 44$^{th}$ aspect of the disclosure, processing the second plurality of intraoral scans using the one or more algorithms configured to determine a three-dimensional surface of a non-static dental site further comprises: determining a first mean curvature for the conflicting surface from the first intraoral scan; determining a second mean curvature for the conflicting surface from the second intraoral scan; and determining that the second mean curvature is less than the first mean curvature.

A 45$^{th}$ aspect of the disclosure may further extend the 40$^{th}$ through the 44$^{th}$ aspect of the disclosure. In the 45$^{th}$ aspect of the disclosure, the method further comprises inputting a height map representing the surface of the non-static dental site into a machine learning model that has been trained to identify portions of gingiva that overlie a margin line, wherein the machine learning model outputs an indication of the portions of the gingiva that overlie the margin line; and hiding or removing, from the height map, data associated with the portions of the gingiva that overlie the margin line.

A 46$^{th}$ aspect of the disclosure may further extend the 45$^{th}$ aspect of the disclosure. In the 46$^{th}$ aspect of the disclosure, the machine learning model outputs a probability map comprising, for each pixel in the height map, a first probability that the pixel belongs to a first dental class and a second probability that the pixel belongs to a second dental class, wherein the first dental class represents portions of gingiva that overlie a margin line, the method further comprising: determining, based on the probability map, one or more pixels in the height map that are classified as portions of gingiva that overlie a margin line.

A 47$^{th}$ aspect of the disclosure may further extend the 40$^{th}$ through the 46$^{th}$ aspect of the disclosure. In the 47$^{th}$ aspect of the disclosure, processing the first plurality of intraoral scans using the one or more algorithms configured to determine a three-dimensional surface of a static dental site comprises: processing the first plurality of intraoral scans using a blending algorithm to generate one or more blended intraoral scans; and processing the blended intraoral scans using a stitching algorithm to stitch together the one or more blended intraoral scans; wherein the blending algorithm is not used to generate blended intraoral scans while in the partial retraction intraoral scanning mode.

A 48$^{th}$ aspect of the disclosure may further extend the 40$^{th}$ through the 47$^{th}$ aspect of the disclosure. In the 48$^{th}$ aspect of the disclosure, the method further comprises: generating a virtual three-dimensional model of the preparation tooth using the second plurality of intraoral scans; and generating a virtual three-dimensional model of a remainder of the dental arch from the first plurality of intraoral scans.

In a 49$^{th}$ aspect of the disclosure, a method comprises: determining that a partial retraction scan of a first preparation tooth will be performed or has been performed, wherein the partial retraction scan comprises an intraoral scan of a preparation tooth that has not been packed with a gingival retraction cord; receiving a plurality of intraoral scans generated by an intraoral scanner; processing, in accordance with a partial retraction intraoral scanning mode, the plurality of intraoral scans by a processing device using a stitching algorithm to stitch together the plurality of intraoral scans, the processing comprising: determining a conflicting surface for a pair of intraoral scans from the plurality of intraoral scans, wherein a first intraoral scan of the pair of intraoral scans has a first distance from a probe of the intraoral scanner for the conflicting surface and a second intraoral scan of the pair of intraoral scans has a second distance from the probe for the conflicting surface; determining that the second distance is greater than the first distance; determining whether a difference between the first distance from the probe and the second distance from the probe is greater than a difference threshold; and responsive to determining that the difference is greater than the difference threshold, discarding a representation of the conflicting surface from the first intraoral scan, wherein the representation of the conflicting surface from the second intraoral scan is used for the conflicting surface.

A 50$^{th}$ aspect of the disclosure may further extend the 49$^{th}$ aspect of the disclosure. In the 50$^{th}$ aspect of the disclosure, the processing further comprises: determining whether a size of the conflicting surface is less than a size threshold; and responsive to determining that the difference is greater than the difference threshold and that the size is less than the size threshold, discarding the representation of the conflicting surface from the first intraoral scan.

A 51$^{st}$ aspect of the disclosure may further extend the 49$^{th}$ or 50$^{th}$ aspect of the disclosure. In the 51$^{st}$ aspect of the disclosure, the method further comprises performing the following prior to determining that the partial retraction scan of a first preparation tooth will be performed or has been performed: receiving an additional plurality of intraoral scans of a dental arch; processing the additional plurality of intraoral scans using a blending algorithm to generate one or more blended intraoral scans; and processing the blended intraoral scans using a first stitching algorithm to stitch together the one or more blended intraoral scans; wherein the blending algorithm is not used to generate blended intraoral scans while in the partial retraction intraoral scanning mode.

A 52$^{nd}$ aspect of the disclosure may further extend the 51$^{st}$ aspect of the disclosure. In the 52$^{nd}$ aspect of the disclosure, the method further comprises: generating a virtual model of the preparation tooth using the plurality of intraoral scans; and generating a virtual model of the dental arch using the blended intraoral scans, wherein the preparation tooth is part of the dental arch.

A 53$^{rd}$ aspect of the disclosure may further extend the 49$^{th}$ through the 52$^{nd}$ aspect of the disclosure. In the 53$^{rd}$ aspect of the disclosure, the method further comprises: determining, by the processing device, that a full retraction intraoral scan of a second preparation tooth has been performed or will be performed; receiving a second plurality of intraoral scans; and processing, in accordance with a full retraction intraoral scanning mode, the plurality of intraoral scans using an alternate stitching algorithm to stitch together the second plurality of intraoral scans.

A 54$^{th}$ aspect of the disclosure may further extend the 49$^{th}$ through the 53$^{rd}$ aspect of the disclosure. In the 54$^{th}$ aspect of the disclosure, determining that the partial retraction scan will be performed or has been performed comprises receiving an indication based on user input.

A 55$^{th}$ aspect of the disclosure may further extend the 49$^{th}$ through the 54$^{th}$ aspect of the disclosure. In the 55$^{th}$ aspect of the disclosure, the plurality of intraoral scans is received prior to determining that the partial retraction scan will be performed or has been performed, the determining comprising automatically determining that the partial retraction scan has been performed based on an analysis of data from one or more of the plurality of intraoral scans.

In a 56$^{th}$ aspect of the disclosure, a method includes: receiving a first intraoral scan of a preparation tooth after a gingival retraction tool has momentarily retracted a first portion of a gingiva surrounding the preparation tooth to partially expose a margin line, wherein a first portion of the margin line is exposed in the first intraoral scan; receiving a second intraoral scan of the preparation tooth after receiving the first intraoral scan, wherein the first portion of the margin line is obscured by the first portion of the gingiva in the second intraoral scan; comparing, by a processing device, the first intraoral scan to the second intraoral scan; identifying, between the first intraoral scan and the second intraoral scan, a conflicting surface at a region of the preparation tooth corresponding to the first portion of the margin line; discarding or marking data for the region of the preparation tooth from the second intraoral scan; and stitching together the first intraoral scan and the second intraoral scan to generate a virtual model of the preparation tooth, wherein data for the region of the preparation tooth from the first intraoral scan is used to generate the virtual model of the preparation tooth, and wherein data for the region of the preparation tooth from the second intraoral scan is not used to generate the virtual model of the preparation tooth.

A $57^{th}$ aspect of the disclosure may further extend the $56^{th}$ aspect of the disclosure. In the $57^{th}$ aspect of the disclosure, the method further comprises performing the following prior to discarding the data for the region of the preparation tooth from the second intraoral scan: determining, for the region of the preparation tooth in the first intraoral scan, a distance from a probe of an intraoral scanner that generated the first intraoral scan; determining, for the region of the preparation tooth in the second intraoral scan, a distance from the probe of the intraoral scanner that generated the second intraoral scan, wherein the second distance is less than the first distance; and determining that a difference between the first distance and the second distance is greater than a difference threshold.

A $58^{th}$ aspect of the disclosure may further extend the $57^{th}$ aspect of the disclosure. In the $58^{th}$ aspect of the disclosure, the method further comprises: determining a size of the conflicting surface; determining whether the size of the conflicting surface is less than a size threshold; and discarding the data for the region of the preparation tooth from the second intraoral scan responsive to determining that the size of the conflicting surface is less than the size threshold and the difference between the first distance and the second distance is greater than the difference threshold.

A $59^{th}$ aspect of the disclosure may further extend the $56^{th}$ through the $58^{th}$ aspect of the disclosure. In the $59^{th}$ aspect of the disclosure, the method further comprises performing the following before receiving the first intraoral scan: receiving, by the processing device, an indication that a partial retraction scan will be performed, wherein the partial retraction scan comprises an intraoral scan of a preparation tooth that has not been packed with a gingival retraction cord; and activating a partial retraction intraoral scanning mode.

A $60^{th}$ aspect of the disclosure may further extend the $56^{th}$ through the $59^{th}$ aspect of the disclosure. In the $60^{th}$ aspect of the disclosure, the method further comprises: receiving a third intraoral scan of the preparation tooth after the gingival retraction tool has momentarily retracted a second portion of the gingiva surrounding the preparation tooth, wherein a second portion of the margin line is exposed in the third intraoral scan, and wherein the first portion of the margin line is obscured by the first portion of the gingiva in the third intraoral scan; receiving a fourth intraoral scan of the preparation tooth after receiving the third intraoral scan, wherein the second portion of the margin line is obscured by the second portion of the gingiva in the second intraoral scan; comparing the third intraoral scan to the fourth intraoral scan; identifying, between the third intraoral scan and the fourth intraoral scan, a conflicting surface at a second region of the preparation tooth corresponding to the second portion of the margin line; determining a third distance from the probe for the region of the preparation tooth in the third intraoral scan; determining a fourth distance from the probe for the region of the preparation tooth in the fourth intraoral scan, wherein the fourth distance is less than the third distance; determining that a difference between the third distance and the fourth distance is greater than a difference threshold; discarding data for the second region of the preparation tooth from the fourth intraoral scan; and stitching together the third intraoral scan and the fourth intraoral scan to generate the virtual model of the preparation tooth, wherein data for the second region of the preparation tooth from the third intraoral scan is used to generate the virtual model of the preparation tooth.

In a $61^{st}$ aspect of the disclosure, a method includes: receiving intraoral scan data of a preparation tooth; generating a first surface for the preparation tooth using the intraoral scan data and a first one or more algorithms, wherein the first surface depicts the preparation tooth without gingival surface information; generating a second surface for the preparation tooth using the intraoral scan data and a second one or more algorithms, wherein the second surface depicts the preparation tooth with the gingival surface information; selecting at least one of the first surface or the second surface; and displaying the selected at least one of the first surface or the second surface.

A $62^{nd}$ aspect of the disclosure may further extend the $61^{st}$ aspect of the disclosure. In the $62^{nd}$ aspect of the disclosure, displaying the selected at least one of the first surface or the second surface comprising displaying a superimposition of the first surface and the second surface.

A $63^{rd}$ aspect of the disclosure may further extend the $61^{st}$ or $62^{nd}$ aspect of the disclosure. In the $63^{rd}$ aspect of the disclosure, the method further comprises: receiving additional intraoral scan data of a dental arch comprising the preparation tooth; generating a third surface for the dental arch, the third surface not including the preparation tooth; and generating a virtual three-dimensional model of the dental arch using the third surface and at least one of the first surface or the second surface.

A $64^{th}$ aspect of the disclosure may further extend the $61^{st}$ through the $63^{rd}$ aspect of the disclosure. In the $64^{th}$ aspect of the disclosure, generating the first surface for the preparation tooth using the intraoral scan data and the first one or more algorithms comprises: determining a conflicting surface from the intraoral scan data, wherein a first intraoral scan of the intraoral scan data has a first distance from a probe of an intraoral scanner for the conflicting surface and a second intraoral scan of the intraoral scan data has a second distance from the probe for the conflicting surface; determining that the first distance is greater than the second distance; determining whether a difference between the first distance and the second distance is greater than a difference threshold; and responsive to determining that the difference is greater than the difference threshold, discarding a representation of the conflicting surface from the second intraoral scan, wherein the representation of the conflicting surface from the first intraoral scan is used for the conflicting surface in the first surface.

A $65^{th}$ aspect of the disclosure may further extend the $61^{st}$ through the $64^{th}$ aspect of the disclosure. In the $65^{th}$ aspect of the disclosure, generating the second surface for the preparation tooth using the intraoral scan data and the second one or more algorithms comprises: determining a conflicting surface from the intraoral scan data, wherein a first intraoral scan of the intraoral scan data has a first distance from a probe of an intraoral scanner for the conflicting surface and a second intraoral scan of the intraoral scan data has a second distance from the probe of the intraoral scanner for the conflicting surface; and averaging a representation of the conflicting surface from the first intraoral scan and a representation of the conflicting surface from the second intraoral scan.

In a $66^{th}$ aspect of the disclosure, a method includes: receiving a first intraoral scan of a preparation tooth after a gingival retraction tool has momentarily retracted a first portion of a gingiva surrounding the preparation tooth to partially expose a margin line, wherein a first portion of the margin line is exposed in the first intraoral scan, and wherein a second portion of the margin line is obscured by the gingiva in the first intraoral scan; receiving a second intraoral scan of the preparation tooth after the gingival retraction tool has momentarily retracted a second portion of the gingiva surrounding the preparation tooth to partially expose the margin line, wherein the second portion of the margin line is exposed in the second intraoral scan, and wherein the first portion of the margin line is obscured by the gingiva in the second intraoral scan; and generating, by a processing device, a virtual model of the preparation tooth using the first intraoral scan and the second intraoral scan, wherein the first intraoral scan is used to generate a first region of the virtual model representing the first portion of the margin line, and wherein the second intraoral scan is used to generate a second region of the virtual model representing the second portion of the margin line.

A $67^{th}$ aspect of the disclosure may further extend the $66^{th}$ aspect of the disclosure. In the $67^{th}$ aspect of the disclosure, the method further comprises performing the following before receiving the first intraoral scan: receiving, by the processing device, an indication that a partial retraction scan will be performed, wherein the partial retraction scan comprises an intraoral scan of a preparation tooth that has not been packed with a gingival retraction cord; and activating a partial retraction intraoral scanning mode.

A $68^{th}$ aspect of the disclosure may further extend the $66^{th}$ or $67^{th}$ aspect of the disclosure. In the 68th aspect of the disclosure, a third portion of the margin line is exposed in the first intraoral scan and in the second intraoral scan, and wherein both the first intraoral scan and the second intraoral scan are used to generate a third region of the virtual model representing the third portion of the margin line.

In a $69^{th}$ aspect of the disclosure, a method includes: receiving first intraoral scan data of a preparation tooth, the first intraoral scan data having been generated after a gingival retraction cord that was packed around the preparation tooth was removed to expose a margin line; generating a first surface for the preparation tooth using the first intraoral scan data and a first one or more algorithms; determining that, for a portion of the first surface depicting a portion of the preparation tooth, the margin line is obscured by gum tissue; generating a second surface for the portion of the preparation tooth obscured by the margin line using a) at least one of the first intraoral scan data or second intraoral scan data, and b) a second one or more algorithms; and replacing the portion of the first surface with the second surface.

A $70^{th}$ aspect of the disclosure may further extend the $69^{th}$ aspect of the disclosure. In the $70^{th}$ aspect of the disclosure, the method further comprises receiving the second intraoral scan data after a gingival retraction tool has momentarily retracted a portion of a gingiva above the portion of the preparation tooth to expose the margin line at the portion of the preparation tooth.

A $71^{st}$ aspect of the disclosure may further extend the $69^{th}$ or $70^{th}$ aspect of the disclosure. In the $71^{st}$ aspect of the disclosure, generating the second surface for the portion of the preparation tooth using a) at least one of the first intraoral scan data or the second intraoral scan data, and b) the second one or more algorithms comprises: determining a conflicting surface at the portion of the preparation tooth from at least one of the first intraoral scan data or the second intraoral scan data, wherein a first intraoral scan of at least one of the first intraoral scan data or second intraoral scan data has a first distance from a probe of an intraoral scanner for the conflicting surface and a second intraoral scan of at least one of the first intraoral scan data or second intraoral scan data has a second distance from the probe for the conflicting surface; determining that the first distance is greater than the second distance; determining whether a difference between the first distance and the second distance is greater than a difference threshold; and responsive to determining that the difference is greater than the difference threshold, discarding a representation of the conflicting surface from the first intraoral scan, wherein the representation of the conflicting surface from the second intraoral scan is used for the conflicting surface in the first surface.

A $72^{nd}$ aspect of the disclosure may further extend the $69^{th}$ through the $71^{st}$ aspect of the disclosure. In the $72^{nd}$ aspect of the disclosure, generating the first surface for the portion of the preparation tooth using the first intraoral scan data and the first one or more algorithms comprises: determining a conflicting surface at the portion of the preparation tooth from the first intraoral scan data, wherein a first intraoral scan of the first intraoral scan data has a first distance from a probe of an intraoral scanner for the conflicting surface and a second intraoral scan of the first intraoral scan data has a second distance from the probe of the intraoral scanner for the conflicting surface; and averaging a representation of the conflicting surface from the first intraoral scan and a representation of the conflicting surface from the second intraoral scan.

In a $73^{rd}$ aspect of the disclosure, a computer readable medium stores instructions that, when executed by a processing device, cause the processing device to execute the methods of any of the $1^{st}$ through the $72^{nd}$ aspects of the disclosure.

In a $74^{th}$ aspect of the disclosure, a computing device comprises a memory and a processing device operably coupled to the memory, wherein the processing device is to execute instructions from the memory which cause the processing device to perform the methods of any of the $1^{st}$ through the $72^{nd}$ aspects of the disclosure.

In a $75^{th}$ aspect of the disclosure, a system includes an intraoral scanner and a computing device operably coupled to the intraoral scanner, wherein the intraoral scanner is to generate scan data and the computing device is to execute the methods of any of the $1^{st}$ through the $72^{nd}$ aspects of the disclosure.

In a $76^{th}$ aspect of the disclosure, a system includes an intraoral scanner and an accompanying computer readable medium comprising instructions for performing the methods of any of the $1^{st}$ through the $72^{nd}$ aspects of the disclosure.

BRIEF DESCRIPTION OF THE DRAWINGS

Embodiments of the present disclosure are illustrated by way of example, and not by way of limitation, in the figures of the accompanying drawings.

FIG. 5A illustrates a flow diagram for a partial retraction method of scanning a preparation tooth, in accordance with an embodiment.

FIG. 5B illustrates another flow diagram for a partial retraction method of scanning a preparation tooth, in accordance with an embodiment.

FIG. 6A illustrates a flow diagram for a method of resolving an obscured margin line for a preparation tooth, in accordance with an embodiment.

FIG. 7A illustrates a flow diagram for generating a virtual 3D model of a preparation tooth using intraoral scan data of an intraoral scanner together with at least one of CBCT scan data, OCT scan data or ultrasound scan data, in accordance with an embodiment.

FIG. 7B illustrates another flow diagram for generating a virtual 3D model of a preparation tooth using intraoral scan data of an intraoral scanner together with at least one of CBCT scan data, OCT scan data or ultrasound scan data, in accordance with an embodiment.

DETAILED DESCRIPTION

Figure 1:
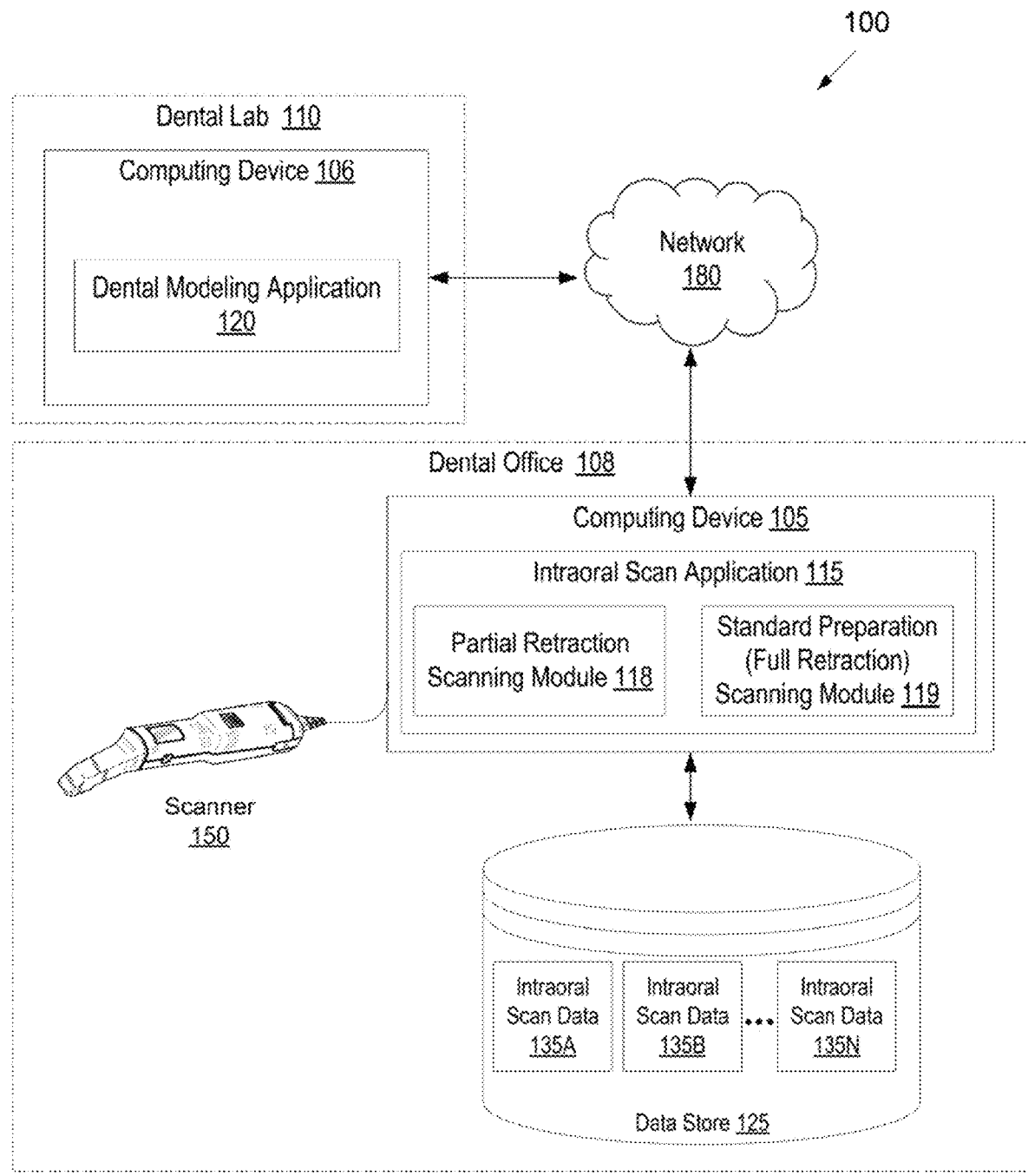
FIG. 1 illustrates one embodiment of a system for performing intraoral scanning and/or generating a virtual three-dimensional model of an intraoral site.

Described herein are methods and systems for accurately determining the shape, position and orientation of a margin line for a preparation tooth and/or for determining other accurate information for a dental site. Some embodiments enable the acquisition of accurate intraoral scan data of a margin line for a preparation tooth. For example, embodiments cover techniques for exposing just portions of the margin line at a time and generating intraoral scans of the exposed portions of the margin line without the use of a retraction cord (which exposes all of the margin line at one time). Other embodiments cover supplementing intraoral scan data with other image data (e.g., x-ray data, CBCT scan data, ultrasound data, etc.) to accurately define a margin line. Other embodiments provide multiple scanning modes, where one scanning mode is for scanning of a preparation tooth for which a retraction cord has been used to expose the margin line and another scanning mode is for scanning of a preparation tooth for which only a portion of the margin line is exposed at a time (e.g., using a technique other than a retraction cord to expose the margin line). For such embodiments tools such as a dental probe, spatula, stream of air, etc. may be used to expose a small region of the margin line while it is scanned. This process may be repeated for all of the regions of the margin line until the entire margin line is scanned.

Also described herein are methods and systems for identifying and/or correcting features in images of teeth and/or in virtual 3D models of teeth. In some embodiments, methods and systems identify and/or correct margin lines in images and/or virtual 3D models of preparation teeth. In other embodiments, other features of teeth (which may or may not be preparation teeth) are identified and/or corrected. Examples of other features that may be identified and/or corrected include cracks, chips, gum line, worn tooth regions, cavities (also known as caries), and so on. Additionally, blood, saliva, poor image capture areas, reflectances, etc. may be identified and/or corrected. Additionally, insertion paths may be identified, model orientation may be determined, blurry regions or regions of low image quality may be identified, and so on.

For many prosthodontic procedures (e.g., to create a crown, bridge, veneer, etc.), an existing tooth of a patient is ground down to a stump. The ground tooth is referred to herein as a preparation tooth, or simply a preparation. The preparation tooth has a margin line (also referred to as a margin line), which is a border between a natural (unground) portion of the preparation tooth and the prepared (ground) portion of the preparation tooth. The preparation tooth is typically created so that a crown or other prosthesis can be mounted or seated on the preparation tooth. In many instances, the margin line of the preparation tooth is sub-gingival (below the gum line). While the term preparation typically refers to the stump of a preparation tooth, including the margin line and shoulder that remains of the tooth, the term preparation herein also includes artificial stumps, pivots, cores and posts, or other devices that may be implanted in the intraoral cavity so as to receive a crown or other prosthesis. Embodiments described herein with reference to a preparation tooth also apply to other types of preparations, such as the aforementioned artificial stumps, pivots, and so on.

After the preparation tooth is created, a practitioner performs operations to ready that preparation tooth for scanning. Readying the preparation tooth for scanning may include wiping blood, saliva, etc. off of the preparation tooth and/or separating a patient's gum from the preparation tooth to expose the margin line. In some instances, a practitioner will insert a material (e.g., a retraction material such as a retraction cord) around the preparation tooth between the preparation tooth and the patient's gum. The practitioner will then remove the cord before generating a set of intraoral scans of the preparation tooth. The soft tissue of the gum will then revert back to its natural position, and in many cases collapses back over the margin line, after a brief time period. Accordingly, the practitioner uses an intraoral scanner to scan the readied preparation tooth and generate a set of intraoral images of the preparation tooth before the soft tissue reverts back to its natural position. The intraoral scanner may be used in a first scanning mode, referred to as a standard preparation or full retraction scanning mode, for this process. In some embodiments, the margin line of the preparation tooth is exposed, or mostly exposed, and the margin line is scanned using the standard preparation scanning mode without the practitioner having taken any steps to expose the margin line.

In one embodiment, the intraoral scanner is used in a second scanning mode, referred to as a partial retraction scanning mode. For the second scanning mode, a practitioner (e.g., a dentist or doctor) uses a tool such as a dental probe, a dental spatula, a triple syringe, a tool to output a stream of air or water, etc. to partially expose the margin line around a preparation tooth being scanned. While a portion of the margin line is exposed, the intraoral scanner generates a scan of the region of the preparation tooth with the exposed portion of the margin line. The practitioner then uses the tool to expose another portion of the margin line, which is also imaged. This process continues until all of the margin line has been exposed and scanned. Different algorithms, settings, rules and criteria may be used for stitching images together for the full retraction scanning mode and for the partial retraction scanning mode. The partial retraction scanning technique may be a more efficient technique for scanning sub-gingival preparations than standard techniques such as use of a retraction cord. The partial retraction scanning technique may be performed more quickly (e.g., on the order of 1-2 minutes, or even less than a minute) and with minimal patient discomfort. Additionally, the practitioner can perform the partial retraction scanning technique without needing to rush to avoid the gingiva collapsing back over the margin line.

In some embodiments, the preparation tooth (including the margin line of the preparation tooth) is scanned using the standard preparation scanning mode. A determination may then be made that one or more portions of the margin line are unclear and/or covered. Those portions of the margin line may then be re-scanned using the partial retraction scanning mode for a more efficient re-scanning process.

The intraoral site at which a prosthesis is to be implanted generally should be measured accurately and studied carefully, so that the prosthesis such as a crown, denture or bridge, for example, can be properly designed and dimensioned to fit in place. A good fit enables mechanical stresses to be properly transmitted between the prosthesis and the jaw, and can prevent infection of the gums and tooth decay via the interface between the prosthesis and the intraoral site, for example. After the intraoral site has been scanned, a virtual 3D model (also referred to herein simply as a 3D model) of the dental site may be generated, and that 3D model may be used to manufacture a dental prosthetic. However, if the area of a preparation tooth containing the margin line lacks definition, it may not be possible to properly determine the margin line, and thus the margin of a restoration may not be properly designed.

Accordingly, embodiments disclosed herein provide automated systems and methods for analyzing, marking, and/or updating the margin line in a virtual 3D model of a preparation tooth generated from an intraoral scan. The virtual 3D model (or images generated from the virtual 3D model or images used to generate the virtual 3D model) is analyzed to identify the margin line. In some embodiments, images from an intraoral scan and/or images generated by projecting a virtual 3D model onto a 2D surface are analyzed using a trained machine learning model that has been trained to determine margin lines on preparation teeth. The margin line may then be marked or drawn on the virtual 3D model. A quality of the margin line may be assessed, and a dental practitioner (also referred to herein as a doctor) may be notified that the margin line should be rescanned if the margin line has a low quality score (e.g., if the virtual 3D model has an unclear, inaccurate, indefinite, and/or indeterminate margin line). Additionally, or alternatively, quality scores may be computed for different segments of the margin line, and any segment of the margin line with a low quality score (e.g., a quality score that is below a quality threshold) may be highlighted or otherwise marked in the 3D model.

The virtual 3D model (or images generated from the virtual 3D model or images used to generate the virtual 3D model) may additionally or alternatively be analyzed to identify and/or correct inaccurate and/or unclear representations of teeth (e.g., a portion of a tooth that is covered by an interfering surface that obscures the margin line), and to correct the inaccurate and/or unclear representation of the tooth. For example, blood, saliva, soft tissue (e.g., a collapsing gum) and/or a retraction material may obscure a margin line in the 3D model. In some embodiments, images from an intraoral scan and/or images (e.g., height maps) generated by projecting a virtual 3D model onto a 2D surface are analyzed using a trained machine learning model that has been trained to redraw or reshape a surface of a tooth to correct inaccuracies and/or regions lacking clarity. Thus, the trained machine learning model may fabricate a correct margin line in a region of an image of a preparation tooth where no clear margin line was shown, and may output a modified image with the correct margin line. The trained machine learning model may also reshape the surface of the preparation tooth (or other tooth) in the image, and output a modified image with the reshaped surface. The modified image may be used to adjust the virtual 3D model of the tooth.

Embodiments provide improved 3D models of preparation teeth that are generated with minimal or no manual manipulation of the 3D models. Traditionally, 3D models are corrected by a lab to ensure a clear and accurate margin line. This may involve sending instructions back to a doctor to perform an additional scan of an unclear region, manually cutting a physical 3D model manufactured from the virtual 3D model, manually manipulating the virtual 3D model (e.g., using computer aided drafting (CAD) tools), and so on. Each of these manual operations takes time and resources, and increases the amount of time that it takes to manufacture a prosthodontic as well as the cost of the prosthodontic. Accordingly, the automated methods and systems described herein that can mark a margin line in a 3D model can enable a doctor to inspect the margin line in the 3D model before sending the 3D model to a lab, and to rescan portions of the preparation tooth in the same patient visit in which the original intraoral scan was performed. Additionally, the automated methods and systems described herein that adjust the preparation tooth and/or the margin line can correct and/or add the margin line in the 3D model. Each of these systems and methods, which may be used alone or together, reduce the cost and time of manufacturing an oral prosthetic.

Additional embodiments are also described that automatically select which intraoral images from one or more intraoral scans to use in generating a 3D model of a dental arch that depicts multiple dental sites (e.g., multiple teeth). Traditionally, a doctor selects a preparation tooth in scanning software, then scans the selected preparation tooth, selects another preparation tooth in the scanning software (if multiple preparation teeth are to be scanned), then scans the other preparation tooth, selects a particular arch to scan, and then scans the remainder of one or more other teeth on the dental arch with the preparation tooth or teeth. This notifies the scanning software which intraoral images to use for each of the teeth on the dental arch in generation of the 3D model. However, the process of separately selecting and then scanning each preparation tooth and the dental arch can be cumbersome to doctors. In embodiments, the scanning software can automatically identify which intraoral images to use for each tooth and/or which scanning mode settings (e.g., partial retraction scanning mode or standard preparation scanning mode) to use without a doctor manually identifying images to be associated with particular preparation teeth and/or scanning mode settings to use for particular preparation teeth. Accordingly, doctors may scan preparation teeth and other teeth in any desired order and using any desired technique for exposing the margin line, and the scanning software may use the automated techniques set forth herein to select which scanning mode settings to use and/or which images to use for depiction of a first preparation tooth, which scanning mode settings to use and/or which other images to use for depiction of a second preparation tooth, and so on, reducing a burden on the doctor.

Embodiments are also described that automatically identify teeth represented in height maps, identify excess gingiva (i.e. gingiva that overlies a margin line) in height maps, identify gums represented in height maps, identify excess material (e.g., material that is not gums or teeth) in height maps, identify low quality surfaces (e.g., blurry surfaces) in height maps, identify model orientation from height maps, identify insertion path from height maps, and/or identify margin line in height maps.

Various embodiments are described herein. It should be understood that these various embodiments may be implemented as stand-alone solutions and/or may be combined. Accordingly, references to an embodiment, or one embodiment, may refer to the same embodiment and/or to different embodiments. Additionally, some embodiments are discussed with reference to restorative dentistry, and in particular to preparation teeth and margin lines. However, it should be understood that embodiments discussed with reference to restorative dentistry (e.g., prosthodontics) may also apply to corrective dentistry (e.g., orthodontia). Additionally, embodiments discussed with reference to preparation teeth may also apply to teeth generally, and not just preparation teeth. Furthermore, embodiments discussed with reference to margin lines may also apply to other dental features, such as cracks, chips, gum lines, caries, and so on. For example, embodiments discussed herein that can identify and correct margin lines can also identify and remove blood and/or saliva on a tooth surface, foreign objects that obscure a tooth surface, poor data capture caused by reflections, captured areas with low clarity, and so on.

Some embodiments are discussed herein with reference to intraoral scans and intraoral images. However, it should be understood that embodiments described with reference to intraoral scans also apply to lab scans or model/impression scans. A lab scan or model/impression scan may include one or more images of a dental site or of a model or impression of a dental site, which may or may not include height maps, and which may or may not include color images. In embodiments a machine learning model may be trained to identify a margin line from images of a lab scan of model/impression scan, for example.

FIG. 1 illustrates one embodiment of a system 100 for performing intraoral scanning and/or generating a virtual three-dimensional model of an intraoral site. In one embodiment, one or more components of system 100 carries out one or more operations described below with reference to FIGS. 2-24B.

System 100 includes a dental office 108 and a dental lab 110. The dental office 108 and the dental lab 110 each include a computing device 105, 106, where the computing devices 105, 106 may be connected to one another via a network 180. The network 180 may be a local area network (LAN), a public wide area network (WAN) (e.g., the Internet), a private WAN (e.g., an intranet), or a combination thereof.

Computing device 105 may be coupled to an intraoral scanner 150 (also referred to as a scanner) and/or a data store 125. Computing device 106 may also be connected to a data store (not shown). The data stores may be local data stores and/or remote data stores. Computing device 105 and computing device 106 may each include one or more processing devices, memory, secondary storage, one or more input devices (e.g., such as a keyboard, mouse, tablet, and so on), one or more output devices (e.g., a display, a printer, etc.), and/or other hardware components.

Intraoral scanner 150 may include a probe (e.g., a hand held probe) for optically capturing three-dimensional structures. The intraoral scanner 150 may be used to perform an intraoral scan of a patient's oral cavity. An intraoral scan application 115 running on computing device 105 may communicate with the scanner 150 to effectuate the intraoral scan. A result of the intraoral scan may be intraoral scan data 135A, 135B through 135N that may include one or more sets of intraoral images. Each intraoral image may be a two-dimensional (2D) or 3D image that includes a height map of a portion of a dental site, and may include x, y and z information. In one embodiment, the intraoral scanner 150 generates numerous discrete (i.e., individual) intraoral images. Sets of discrete intraoral images may be merged into a smaller set of blended intraoral images, where each blended image is a combination of multiple discrete images. The scanner 150 may transmit the intraoral scan data 135A, 135B through 135N to the computing device 105. Computing device 105 may store the intraoral scan data 135A-135N in data store 125.

According to an example, a user (e.g., a practitioner) may subject a patient to intraoral scanning. In doing so, the user may apply scanner 150 to one or more patient intraoral locations. The scanning may be divided into one or more segments. As an example, the segments may include a lower buccal region of the patient, a lower lingual region of the patient, an upper buccal region of the patient, an upper lingual region of the patient, one or more preparation teeth of the patient (e.g., teeth of the patient to which a dental device such as a crown or other dental prosthetic will be applied), one or more teeth which are contacts of preparation teeth (e.g., teeth not themselves subject to a dental device but which are located next to one or more such teeth or which interface with one or more such teeth upon mouth closure), and/or patient bite (e.g., scanning performed with closure of the patient's mouth with the scan being directed towards an interface area of the patient's upper and lower teeth). Via such scanner application, the scanner 150 may provide intraoral scan data 135A-N to computing device 105. The intraoral scan data 135A-N may be provided in the form of intraoral image data sets, each of which may include 2D intraoral images and/or 3D intraoral images of particular teeth and/or regions of an intraoral site. In one embodiment, separate image data sets are created for the maxillary arch, for the mandibular arch, for a patient bite, and for each preparation tooth. Alternatively, a single large intraoral image data set is generated (e.g., for a mandibular and/or maxillary arch). Such images may be provided from the scanner to the computing device 105 in the form of one or more points (e.g., one or more pixels and/or groups of pixels). For instance, the scanner 150 may provide such a 3D image as one or more point clouds. The intraoral images may each comprise a height map that indicates a depth for each pixel.

The manner in which the oral cavity of a patient is to be scanned may depend on the procedure to be applied thereto. For example, if an upper or lower denture is to be created, then a full scan of the mandibular or maxillary edentulous arches may be performed. In contrast, if a bridge is to be created, then just a portion of a total arch may be scanned which includes an edentulous region, the neighboring preparation teeth (e.g., abutment teeth) and the opposing arch and dentition. Additionally, the manner in which the oral cavity is to be scanned may depend on a doctor's scanning preferences and/or patient conditions. For example, some doctors may perform an intraoral scan (e.g., in a standard preparation scanning mode) after using a retraction cord to expose a margin line of a preparation. Other doctors may use a partial retraction scanning technique in which only portions of the margin line are exposed and scanned at a time (e.g., performing a scan in a partial retraction scanning mode).

By way of non-limiting example, dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity (intraoral site), or a real or virtual model thereof, or directed to the design and preparation of the intraoral site to receive such a prosthesis. A prosthesis may include any restoration such as crowns, veneers, inlays, onlays, implants and bridges, for example, and any other artificial partial or complete denture. The term orthodontic procedure refers, inter alia, to any procedure involving the oral cavity and directed to the design, manufacture or installation of orthodontic elements at a intraoral site within the oral cavity, or a real or virtual model thereof, or directed to the design and preparation of the intraoral site to receive such orthodontic elements. These elements may be appliances including but not limited to brackets and wires, retainers, clear aligners, or functional appliances.

For many prosthodontic procedures (e.g., to create a crown, bridge, veneer, etc.), a preparation tooth is created (e.g., by grinding a portion of a tooth to a stump). The preparation tooth has a margin line that can be important to proper fit of a dental prosthesis. After the preparation tooth is created, a practitioner performs operations to ready that preparation tooth for scanning. Readying the preparation tooth for scanning may include wiping blood, saliva, etc. off of the preparation tooth and/or separating a patient's gum from the preparation tooth to expose the margin line.

In some instances, a practitioner will perform a standard preparation (full retraction) technique to expose an entirety of the margin line at once by inserting a cord around the preparation tooth between the preparation tooth and the patient's gum and then removing the cord before generating a set of intraoral scans of the preparation tooth. The soft tissue of the gum will then revert back to its natural position, and in many cases collapses back over the margin line, after a brief time period. Accordingly, some of intraoral scan data 135A-N may include images that were taken before the gum has collapsed over the margin line, and other intraoral scan data 135A-N may include images that were taken after the gum has collapsed over the martin line. As a result, some image data is superior to other image data in depicting the preparation tooth, and in particular in depicting the margin line. In some embodiments, the dental practitioner may provide an indication that a standard preparation technique will be used for a preparation tooth (e.g., by pressing a button or making a selection). Alternatively, intraoral scan application 115 may analyze the scan data and automatically determine (i.e. without user input) that a standard preparation technique was performed based on the scan data.

In some instances a dental practitioner performs a partial retraction scanning technique. For the partial retraction scanning technique, the gingiva is pushed aside by a tool to expose a small section of the margin line of the sub-gingival preparation. That small section is scanned, and the tool is moved, allowing the small section of the gingiva to collapse back over margin line and exposing another small section of the margin line. Accordingly, readying the preparation tooth for scanning may include using a tool to expose just a portion of the margin line, which is then scanned while it is exposed. Readying the preparation tooth may then include using the tool to expose another portion of the margin line, which is scanned while it is exposed. This process may continue until all of the margin line has been scanned.

Examples of tools that may be used to expose a portion of the margin line at a time include a dental probe, a dental spatula, a triple syringe, an air gun, dental floss, a water gun, and so on. In some embodiments, specific tools are developed for exposing one or more portions of the margin line around one or more teeth (e.g., a first tool for exposing an interproximal portion of a margin line, a second tool for exposing a lingual portion of a margin line, and so on). Different tools developed for exposing different portions of the margin line of a tooth may have protrusions, lengths, probes, spatulas, etc. with different lengths, widths, angles, and so on.

In some embodiments, the dental practitioner may provide an indication that a partial preparation technique will be used for a preparation tooth (e.g., by pressing a button or making a selection). Alternatively, intraoral scan application 115 may analyze the scan data and automatically determine (i.e. without user input) that a partial retraction preparation technique was performed based on the scan data.

When a scan session is complete (e.g., all images for an intraoral site or dental site have been captured), intraoral scan application 115 may generate a virtual 3D model of one or more scanned dental sites. To generate the virtual 3D model, intraoral scan application 115 may register and "stitch" or merge together the intraoral images generated from the intraoral scan session. In one embodiment, performing image registration includes capturing 3D data of various points of a surface in multiple images (views from a camera), and registering the images by computing transformations between the images. The 3D data may be in the form of multiple height maps, which may be projected into a 3D space of a 3D model to form a portion of the 3D model. The images may be integrated into a common reference frame by applying appropriate transformations to points of each registered image and projecting each image into the 3D space.

In one embodiment, image registration is performed for adjacent or overlapping intraoral images (e.g., each successive frame of an intraoral video). In one embodiment, image registration is performed using blended images. Image registration algorithms are carried out to register two adjacent intraoral images (e.g., two adjacent blended intraoral images) and/or to register an intraoral image with a 3D model, which essentially involves determination of the transformations which align one image with the other image and/or with the 3D model. Image registration may involve identifying multiple points in each image (e.g., point clouds) of an image pair (or of an image and the 3D model), surface fitting to the points, and using local searches around points to match points of the two images (or of the image and the 3D model). For example, intraoral scan application 115 may match points of one image with the closest points interpolated on the surface of another image, and iteratively minimize the distance between matched points. Other image registration techniques may also be used.

Intraoral scan application may repeat image registration for all images of a sequence of intraoral images to obtain transformations for each image, to register each image with the previous one and/or with a common reference frame (e.g., with the 3D model). Intraoral scan application 115 integrates all images into a single virtual 3D model by applying the appropriate determined transformations to each of the images. Each transformation may include rotations about one to three axes and translations within one to three planes.

In many instances, data from one or more intraoral images does not perfectly correspond to data from one or more other intraoral images. Accordingly, in embodiments intraoral scan application 115 may process intraoral images (e.g., which may be blended intraoral images) to determine which intraoral images (and/or which portions of intraoral images) to use for portions of a 3D model (e.g., for portions representing a particular dental site). Intraoral scan application 115 may use data such as geometric data represented in images and/or time stamps associated with the images to select optimal images to use for depicting a dental site or a portion of a dental site (e.g., for depicting a margin line of a preparation tooth).

In one embodiment, images are input into a machine learning model that has been trained to select and/or grade images of dental sites. In one embodiment, one or more scores are assigned to each image, where each score may be associated with a particular dental site and indicate a quality of a representation of that dental site in the intraoral images. Once a set of images as selected for use in generating a portion of a 3D model that represents a particular dental site (e.g., a preparation tooth), those images and/or portions of those images may be locked. Locked images or portions of locked images that are selected for a dental site may be used exclusively for creation of a particular region of a 3D model (e.g., for creation of the associated tooth in the 3D model).

Additionally, or alternatively, intraoral images may be assigned weights based on scores assigned to those images. Assigned weights may be associated with different dental sites. In one embodiment, a weight may be assigned to each image (e.g., to each blended image) for a dental site (or for multiple dental sites). During model generation, conflicting data from multiple images may be combined using a weighted average to depict a dental site. The weights that are applied may be those weights that were assigned based on quality scores for the dental site. For example, processing logic may determine that data for a particular overlapping region from a first set of intraoral images is superior in quality to data for the particular overlapping region of a second set of intraoral images. The first image data set may then be weighted more heavily than the second image data set when averaging the differences between the image data sets. For example, the first images assigned the higher rating may be assigned a weight of 70% and the second images may be assigned a weight of 30%. Thus, when the data is averaged, the merged result will look more like the depiction from the first image data set and less like the depiction from the second image data set.

In one embodiment, intraoral scan application includes a partial retraction scanning module 118 and a standard preparation (full retraction) scanning module 119. Standard preparation scanning module 119 may provide a standard preparation (full retraction) scanning mode in which one or more first algorithms are used to process intraoral scan data. Partial retraction scanning module 118 may provide a partial preparation scanning mode in which one or more second algorithms are used to process intraoral scan data. The first algorithms and second algorithms may use different rules, settings, thresholds and so on to select which images and which portions of images are used to construct portions of a virtual 3D model.

As mentioned, standard preparation scanning module 119 may provide a standard preparation (full retraction) scanning mode in which one or more first algorithms are used to process intraoral scan data. The first algorithms of the standard preparation scanning mode may be optimized to generate a virtual 3D model of a preparation tooth with as clear and accurate a depiction of a margin line as possible given the scan data generated using the full retraction technique for exposing the margin line. The first algorithms may include, for example, a moving tissue detection algorithm, an excess material removal algorithm, a blending algorithm, a stitching and/or registration algorithm, and so on. Such algorithms may be configured on the assumption that the dental region being scanned is static (e.g., unmoving). Accordingly, if there is a disturbance or rapid change (e.g., a feature that is shown for only a short amount of time), the first algorithms may operate to minimize or filter out such data on the assumption that it is not part of the scanned object. For example, the first algorithms may classify such data as depictions of a tongue, cheek, finger of a doctor, tool, etc., and may not use such data in generation of a 3D model of the preparation tooth. However, such algorithms may also remove margin line data if used on scan data generated using a partial retraction scanning technique.

In one embodiment, in the standard preparation scanning mode raw intraoral scans are received from the intraoral scanner 150, and are preliminarily registered to one another using an initial registration algorithm. A blending algorithm is then applied to the raw scans. If the scans are similar (e.g., all having a time stamp that differs by less than a time difference threshold and with surface differences that are less a surface difference threshold and/or position/orientation differences that are less than a position/orientation threshold), then the scans are blended together by the blending algorithm. For example, up to 10-20 consecutive scans taking within seconds or micro-seconds of one another may be blended together. This includes averaging the data of the scans being blended and generating a single blended scan from the averaged data. Generation of blended scans reduces the total number of scans that are processed at later scan processing stages.

The blended scans are then processed using an excess material tissue algorithm which identifies moving tissue with a size that is larger than a size threshold (e.g., over 100 or 200 microns) and then erases such excess material from the blended scans. In one embodiment, the excess material identification algorithm is a trained machine learning model (e.g., a neural network such as a convolutional neural network) that has been trained to identify such excess material. One embodiment of the machine learning model that is used for excess material removal is described in U.S. patent application Ser. No. 16/865,162, filed May 1, 2020, which is incorporated by reference herein.

Another registration algorithm then registers the blended scans together. A moving tissue algorithm then identifies moving tissue based on differences between blended scans. The moving tissue algorithm may identify moving tissue with a size that is greater than some threshold (e.g., 100 or 200 microns), and may erase such moving tissue from the blended scans. A merging algorithm may then merge together all of the remaining image data of the blended scans to generate a virtual 3D model of the preparation. The merging algorithm may average differences in data between the scans. Such differences may have a difference that is less than a threshold difference value, such as less than 0.5 mm.

Partial retraction scanning module 118 may provide a partial preparation scanning mode in which one or more second algorithms are used to process intraoral scan data. The second algorithms of the partial retraction scanning mode may be optimized to generate a virtual 3D model of a preparation tooth with as clear and accurate a depiction of a margin line as possible given the scan data generated using the partial retraction technique for exposing the margin line.

The second algorithms may include, for example, a moving tissue detection algorithm, an excess material removal algorithm, a blending algorithm, a registration algorithm, a stitching or merging algorithm, and so on. In some embodiments, the second algorithms include an excess material removal algorithm, a registration algorithm and a stitching or merging algorithm. The scan data will be different for the two techniques, and the differences in the algorithms may be to account for the differences in the scan data produced by the different scanning techniques.

When the partial retraction scanning technique is used, the size of the exposed region of the margin line may be on the order of tens of microns. Such an exposed region of the margin line may change between scans, and may be removed by the excess material removal algorithms and/or moving tissue removal algorithms of the standard preparation scanning mode. Additionally, for partial retraction scanning there may be interrupts between scans due to the doctor moving the retraction tool between scans, whereas for standard scanning the scanning may be continuous with no interruptions. This can increase a time and difficulty in registration between scans, which are minimized in embodiments of the second algorithms. The second algorithms may omit the moving tissue and/or excess material removal algorithms so as not to identify and remove excess material (e.g., fingers, tongue, cheeks, tools, etc.). In some embodiments, the second algorithms include a different version of a moving tissue algorithm and/or a different version of an excess material removal algorithm than is included in the first algorithms. For example, the criteria for what constitutes excess material and/or moving tissue may be changed for the excess material removal algorithm and/or moving tissue detection algorithm so that portions of margin lines are not classified as excess material or moving tissue.

Additionally, the first algorithms may blend scan data of multiple scans together to generate blended scans, whereas scans may not be blended using the second algorithms in some embodiments. Alternatively, the criteria for what scans can be blended together (and/or what portions of scans can be blended together) in the second algorithms may be stricter than the criteria of what scans (and/or what portions of scans) can be blended together in the first algorithms. In one embodiment, the first algorithms average the blended images at least for areas that meet some criteria (e.g., size of a matching region criterion). In one embodiment, the second algorithms omit blending for all or parts of the scans.

In one embodiment in the partial retraction scanning mode raw intraoral scans are received from the intraoral scanner 150. The raw scans may or may not be preliminarily registered to each other using an initial registration algorithm. In some instances blended scans are generated by blending together the raw scans. In one embodiment, blended scans are generated from multiple raw scans that were generated while a same region of a margin line was exposed. Accordingly, a blended scan may not include different scans in which different portions of a margin line are exposed. As discussed above, if a blending algorithm is used, then the blending algorithm may have stricter criteria for what data can be blended together than the blending algorithm used for the standard preparation scanning mode.

In some embodiments, the partial retraction scanning mode does not use an excess material removal algorithm. Alternatively, the partial retraction scanning mode may use an excess material removal algorithm with stricter criteria than the criteria used to identify excess material in the standard preparation scanning mode. In one embodiment, the excess material removal algorithm includes a size threshold that is higher than 200 microns, such as 300 microns, 400 microns or 500 microns, and areas that exceed this size criterion may be identified as excess material and removed. This is to prevent removal of margin line information from scans.

In one embodiment, the excess material identification algorithm is a trained machine learning model (e.g., a neural network such as a convolutional neural network) that has been trained to identify such excess material. The machine learning model may have been specifically trained with training data that includes depictions of margin lines, so that it does not identify areas of margin lines that are changing between scans as excess material. The machine learning model may have been trained using a training dataset that includes scans of gingiva over margin lines and scans of exposed margin lines not covered by gingiva. Such a machine learning model may be trained to remove gingiva and leave exposed margin lines in an embodiment. In one embodiment, a specific excess gingiva removal algorithm (e.g., trained machine learning model) is used rather than a generic excess material removal algorithm. In one embodiment, two excess material removal algorithms are used, where one is for removing excess gingiva and the other is for removing other excess material. In one embodiment, inputs for the trained machine learning model that has been trained to remove excess gingiva are sets of scans. The trained machine learning model may determine for the sets of scans which scan data represents excess gingiva and should be removed.

One embodiment of the machine learning model that is used for excess material removal and/or excess gingiva removal is described in U.S. patent application Ser. No. 16/865,162, except that the training dataset that is used to train the machine learning model is different from the training dataset described in the referenced patent application. In particular, the training dataset used to train the machine learning model includes scans showing gingiva over margin lines, in which the areas with gingiva over the margin lines are labeled with pixel-level labeling as excess material as well as scans showing exposed margin lines with retracted gingiva that does not cover portions of the margin lines, which are labeled with pixel-level labels identifying areas of gingiva that are not classified as excess material. The machine learning model may be trained to perform image segmentation in a manner that classifies pixels representing excess gingiva that is over margin lines as such, for example.

In one embodiment, an excess gingiva removal algorithm is used to identify and remove excess gingiva that overlies the margin line of a preparation. The excess gingiva removal algorithm may be similar to the excess material removal algorithm, but may be trained specifically to identify excess gingiva overlying a margin line for removal.

One type of machine learning model that may be used for the excess material removal algorithm and/or for the excess gingiva removal algorithm is an artificial neural network, such as a deep neural network. Artificial neural networks generally include a feature representation component with a classifier or regression layers that map features to a desired output space. A convolutional neural network (CNN), for example, hosts multiple layers of convolutional filters. Pooling is performed, and non-linearities may be addressed, at lower layers, on top of which a multi-layer perceptron is commonly appended, mapping top layer features extracted by the convolutional layers to decisions (e.g. classification outputs). Deep learning is a class of machine learning algorithms that use a cascade of multiple layers of nonlinear processing units for feature extraction and transformation. Each successive layer uses the output from the previous layer as input. Deep neural networks may learn in a supervised (e.g., classification) and/or unsupervised (e.g., pattern analysis) manner. Deep neural networks include a hierarchy of layers, where the different layers learn different levels of representations that correspond to different levels of abstraction. In deep learning, each level learns to transform its input data into a slightly more abstract and composite representation. In an image recognition application, for example, the raw input may be a matrix of pixels; the first representational layer may abstract the pixels and encode edges; the second layer may compose and encode arrangements of edges; the third layer may encode higher level shapes (e.g., teeth, lips, gums, etc.); and the fourth layer may recognize that the image contains a face or define a bounding box around teeth in the image. Notably, a deep learning process can learn which features to optimally place in which level on its own. The "deep" in "deep learning" refers to the number of layers through which the data is transformed. More precisely, deep learning systems have a substantial credit assignment path (CAP) depth. The CAP is the chain of transformations from input to output. CAPs describe potentially causal connections between input and output. For a feedforward neural network, the depth of the CAPs may be that of the network and may be the number of hidden layers plus one. For recurrent neural networks, in which a signal may propagate through a layer more than once, the CAP depth is potentially unlimited.

In one embodiment, a U-net architecture is used. A U-net is a type of deep neural network that combines an encoder and decoder together, with appropriate concatenations between them, to capture both local and global features. The encoder is a series of convolutional layers that increase the number of channels while reducing the height and width when processing from inputs to outputs, while the decoder increases the height and width and reduces the number of channels. Layers from the encoder with the same image height and width may be concatenated with outputs from the decoder. Any or all of the convolutional layers from encoder and decoder may use traditional or depth-wise separable convolutions.

In one embodiment, the machine learning model is a recurrent neural network (RNN). An RNN is a type of neural network that includes a memory to enable the neural network to capture temporal dependencies. An RNN is able to learn input-output mappings that depend on both a current input and past inputs. The RNN will address past and future scans and make predictions based on this continuous scanning information. RNNs may be trained using a training dataset to generate a fixed number of outputs (e.g., to classify time varying data such as video data as belonging to a fixed number of classes). One type of RNN that may be used is a long short term memory (LSTM) neural network.

A common architecture for such tasks is LSTM (Long Short Term Memory). Unfortunately, LSTM is not well suited for images since it does not capture spatial information as well as convolutional networks do. For this purpose, one can utilize ConvLSTM—a variant of LSTM containing a convolution operation inside the LSTM cell. ConvLSTM is a variant of LSTM (Long Short-Term Memory) containing a convolution operation inside the LSTM cell. ConvLSTM replaces matrix multiplication with a convolution operation at each gate in the LSTM cell. By doing so, it captures underlying spatial features by convolution operations in multiple-dimensional data. The main difference between ConvLSTM and LSTM is the number of input dimensions. As LSTM input data is one-dimensional, it is not suitable for spatial sequence data such as video, satellite, radar image data set. ConvLSTM is designed for 3-D data as its input. In one embodiment, a CNN-LSTM machine learning model is used. A CNN-LSTM is an integration of a CNN (Convolutional layers) with an LSTM. First, the CNN part of the model processes the data and a one-dimensional result feeds an LSTM model.

In one embodiment, a class of machine learning model called a MobileNet is used. A MobileNet is an efficient machine learning model based on a streamlined architecture that uses depth-wise separable convolutions to build light weight deep neural networks. MobileNets may be convolutional neural networks (CNNs) that may perform convolutions in both the spatial and channel domains. A MobileNet may include a stack of separable convolution modules that are composed of depthwise convolution and pointwise convolution (cony 1×1). The separable convolution independently performs convolution in the spatial and channel domains. This factorization of convolution may significantly reduce computational cost from $HWNK^2M$ to $HWNK^2$ (depthwise) plus HWNM (cony 1×1), $HWN(K^2+M)$ in total, where N denotes the number of input channels, $K^2$ denotes the size of convolutional kernel, M denotes the number of output channels, and H×W denotes the spatial size of the output feature map. This may reduce a bottleneck of computational cost to cony 1×1.

In one embodiment, a generative adversarial network (GAN) is used. A GAN is a class of artificial intelligence system that uses two artificial neural networks contesting with each other in a zero-sum game framework. The GAN includes a first artificial neural network that generates candidates and a second artificial neural network that evaluates the generated candidates. The GAN learns to map from a latent space to a particular data distribution of interest (a data distribution of changes to input images that are indistinguishable from photographs to the human eye), while the discriminative network discriminates between instances from a training dataset and candidates produced by the generator. The generative network's training objective is to increase the error rate of the discriminative network (e.g., to fool the discriminator network by producing novel synthesized instances that appear to have come from the training dataset). The generative network and the discriminator network are co-trained, and the generative network learns to generate images that are increasingly more difficult for the discriminative network to distinguish from real images (from the training dataset) while the discriminative network at the same time learns to be better able to distinguish between synthesized images and images from the training dataset. The two networks of the GAN are trained once they reach equilibrium. The GAN may include a generator network that generates artificial intraoral images and a discriminator network that segments the artificial intraoral images. In embodiments, the discriminator network may be a MobileNet.

In one embodiment, the machine learning model is a conditional generative adversarial (cGAN) network, such as pix2pix. These networks not only learn the mapping from input image to output image, but also learn a loss function to train this mapping. GANs are generative models that learn a mapping from random noise vector z to output image y, $G:z \rightarrow y$. In contrast, conditional GANs learn a mapping from observed image x and random noise vector z, to y, $G:x\{x, z\} \rightarrow y$. The generator G is trained to produce outputs that cannot be distinguished from "real" images by an adversarially trained discriminator, D, which is trained to do as well as possible at detecting the generator's "fakes". The generator may include a U-net or encoder-decoder architecture in embodiments. The discriminator may include a Mobile-Net architecture in embodiments. An example of a cGAN machine learning architecture that may be used is the pix2pix architecture described in Isola, Phillip, et al. "Image-to-image translation with conditional adversarial networks." arXiv preprint (2017).

Training of a neural network may be achieved in a supervised learning manner, which involves feeding a training dataset consisting of labeled inputs through the network, observing its outputs, defining an error (by measuring the difference between the outputs and the label values), and using techniques such as deep gradient descent and backpropagation to tune the weights of the network across all its layers and nodes such that the error is minimized. In many applications, repeating this process across the many labeled inputs in the training dataset yields a network that can produce correct output when presented with inputs that are different than the ones present in the training dataset. In high-dimensional settings, such as large images, this generalization is achieved when a sufficiently large and diverse training dataset is made available.

Training of the machine learning model and use of the trained machine learning model (e.g., for the excess material removal algorithm and/or the excess gingiva removal algorithm) may be performed by processing logic executed by a processor of a computing device. For training of the machine learning model, a training dataset containing hundreds, thousands, tens of thousands, hundreds of thousands or more images should be used to form a training dataset. In embodiments, up to millions of cases of patient dentition that underwent a prosthodontic or orthodontic procedure may be available for forming a training dataset, where each case may include a final virtual 3D model of a dental arch (or other dental site such as a portion of a dental arch) that lacks excess material and/or excess gingiva as well as an initial virtual 3D model of the dental arch (or other dental site) that includes excess material and/or includes excess gingiva. Cases may additionally or alternatively include virtual 3D models of dental arches (or other dental sites) with labeled dental classes. Each case may include, for example, data showing an initial 3D model of one or more dental sites generated from an intraoral scan, data showing a final 3D model as corrected by lab technicians, data showing whether the doctor accepted the modified 3D model, and so on. This data may be processed to generate a training dataset for training of one or more machine learning models. The machine learning models may be trained to automatically classify and/or segment intraoral scans during or after an intraoral scanning session, and the segmentation/classification may be used to automatically remove excess material and/or excess gingiva from the images. Such trained machine learning models can reduce the amount of post processing that a lab technician spends cleaning up a virtual 3D model, and can improve the accuracy of 3D models of dental arches or other dental sites produced from an intraoral scan.

In one embodiment, a machine learning model is trained to segment intraoral images by classifying regions of those intraoral images into one or more dental classes. A set of many (e.g., thousands to millions) 3D models of dental arches with labeled dental classes may be collected. Alternatively, or additionally, many pairs of original 3D models and modified 3D models may be collected. Each pair of an original 3D model that includes excess material and/or excess gingiva and a corresponding modified 3D model that lacks excess material and/or excess gingiva may be associated with a particular case and/or patient. Processing logic may compare original 3D models to corresponding modified 3D models to determine differences therebetween. The differences may represent excess material and/or excess gingiva that was removed from the original 3D model by software and/or by a lab technician. Processing logic may automatically label each point on the original 3D model that is not present in the corresponding modified 3D model as excess material. Other points on the modified 3D model and/or original 3D model may additionally include labels (e.g., be labeled as teeth or gingiva not overlying a margin line). The labels from the modified 3D models may be transferred to the corresponding original 3D models in embodiments. Accordingly, the original 3D models may be modified to include at a minimum a first label representing excess material and/or excess gingiva (i.e., gingiva overlying a margin line) and a second label representing non-excess material and/or gingiva not overlying a margin line. In an example, each point in an original 3D model may be modified to include a label having a first value for a first label representing excess gingiva, a second value for a second label representing other excess material, a third value for a third label representing teeth, and a fourth value for a fourth label representing non-excess gingiva. One of the four values may be 1, and the other three values may be 0, for example.

For each 3D model with labeled dental classes, a set of images (e.g., height maps) may be generated. Each image may be generated by projecting the 3D model (or a portion of the 3D model) onto a 2D surface or plane. Different images of a 3D model may be generated by projecting the 3D model onto different 2D surfaces or planes in some embodiments. For example, a first image of a 3D model may be generated by projecting the 3D model onto a 2D surface that is in a top down point of view, a second image may be generated by projecting the 3D model onto a 2D surface that is in a first side point of view (e.g., a buccal point of view), a third image may be generated by projecting the 3D model onto a 2D surface that is in a second side point of view (e.g., a lingual point of view), and so on. Each image may include a height map that includes a depth value associated with each pixel of the image. For each image, a probability map or mask may be generated based on the labeled dental classes in the 3D model and the 2D surface onto which the 3D model was projected. The probability map or mask may have a size that is equal to a pixel size of the generated image. Each point or pixel in the probability map or mask may include a probability value that indicates a probability that the point represents one or more dental classes. For example, there may be four dental classes, including a first dental class representing excess gingiva, a second dental class representing other excess material, a third dental class representing teeth, and a fourth dental class representing non-excess gingiva. Alternatively, a single dental class may be used both for excess gingiva and other excess material. In such an embodiment, there may be three dental classes, including a first dental class representing excess material (including excess gingiva), a second dental class representing teeth, and a third dental class representing non-excess gingiva. In this example, points that have a first dental class may have a value of (1, 0, 0) (100% probability of first dental class and 0% probability of second and third dental classes), points that have a second dental class may have a value of (0, 1, 0), and points that have a third dental class may have a value of (0, 0, 1), for example.

A training dataset may be gathered, where each data item in the training dataset may include an image (e.g., an image comprising a height map) and an associated probability map. Additional data may also be included in the training data items. Accuracy of segmentation can be improved by means of additional classes, inputs and multiple views support. Multiple sources of information can be incorporated into model inputs and used jointly for prediction. Multiple dental classes can be predicted concurrently from a single model. Multiple problems can be solved simultaneously: excess material removal, teeth/gums segmentation, stitching conflicts resolution, holes filling, etc. Accuracy is higher than traditional image and signal processing approaches.

Additional data may include a color image. For example, for each image (which may be a monochrome), there may also be a corresponding color image. Each data item may include the height map as well as the color image. Two different types of color images may be available. One type of color image is a viewfinder image, and another type of color image is a scan texture. A scan texture may be a combination or blending of multiple different viewfinder images. Each intraoral scan may be associated with a corresponding viewfinder image generated at about the same time that the intraoral image was generated. If blended scans are used, then each scan texture may be based on a combination of viewfinder images that were associated with the raw scans used to produce a particular blended scan.

The default method may be based on depth info only and still allows distinguishing several dental classes: teeth, gums, excess material (e.g., moving tissues). However, sometimes depth info is not enough for good accuracy. For example, a partially scanned tooth may look like gums or even excess material in monochrome. In such cases color info may help. In one embodiment, color info Is used as an additional 3 layers (e.g., RGB), thus, getting 4 layers input for the network. Two types of color info may be used, which may include viewfinder images and scan textures. Viewfinder images are of better quality but need alignment with respect to height maps. Scan textures are aligned with height maps, but may have color artifacts.

Another type of additional data may include an image generated under specific lighting conditions (e.g., an image generated under ultraviolet or infrared lighting conditions). The additional data may be a 2D or 3D image, and may or may not include a height map.

In some embodiments, sets of data points are associated with the same dental site, and are sequentially labeled. In some embodiments a recurrent neural network is used, and the data points are input into a machine learning model during training in ascending order.

In some embodiments, each image includes two values for each pixel in the image, where the first value represents height (e.g., provides a height map), and where the second value represents intensity. Both the height values and the intensity values may be used to train a machine learning model.

In an example, a confocal intraoral scanner may determine the height of a point on a surface (which is captured by a pixel of an intraoral image) based on a focus setting of the intraoral scanner that resulted in a maximum intensity for that point on the surface. The focus setting provides a height or depth value for the point. Typically the intensity value (referred to as a grade) is discarded. However, the intensity value (grade) associated with the height or depth value may be kept, and may be included in the input data provided to the machine learning model.

A machine learning model may be trained using the images generated from the 3D models with the labeled dental classes. The machine learning model may be trained to classify pixels in images as belonging to one or more dental classes. The result of this training is a function that can predict dental classes directly from height maps. In particular, the machine learning model may be trained to generate a probability map, where each point in the probability map corresponds to a pixel of an input image and indicates one or more of a first probability that the pixel represents a first dental class, a second probability that the pixel represents a second dental class, a third probability that the pixel represents a third dental class, a fourth probability that the pixels represents a fourth dental class, a fifth probability that the pixel represents a fifth dental class, and so on. In the case of teeth/gums/excess material segmentation, three valued labels are generated.

During an inference stage (i.e., use of the trained machine learning model), the intraoral scan or scans (and optionally other data) is input into the trained model, which may have been trained as set forth above. The trained machine learning model outputs a probability map, where each point in the probability map corresponds to a pixel in the image and indicates probabilities that the pixel represents one or more dental classes. In the case of teeth/non-excess gingiva/ excess material segmentation, three valued labels are generated for each pixel. The corresponding predictions have a probability nature: for each pixel there are three numbers that sum up to 1.0 and can be interpreted as probabilities of the pixel to correspond to these three classes.

In case of three classes, it is convenient to store such predictions of dental classes in an RGB format. For example, a first value for a first dental class may be stored as a red intensity value, a second value for a second dental class may be stored as a green intensity value, and a third value for a third dental class may be stored as a blue intensity value. This may make visualization of the probability map very easy. Usually, there is no need in high precision and chars can be used instead of floats—that is 256 possible values for every channel of the pixel. Further optimization can be done in order to reduce the size and improve performance (e.g., use 16 values quantization instead of 256 values).

In one embodiment, the probability map is used to update the intraoral image/scan to generate a modified intraoral image/scan. The probability map may be used to determine pixels that represent excess material (including excess gingiva). Data for pixels labeled as excess material may then be removed from or hidden in the intraoral image/scan. This may include actually removing the pixels labeled as excess material from the intraoral image/scan, applying a filter to the intraoral image/scan, or modifying the pixels of the intraoral image/scan labeled as excess material to a value that indicates that there is no surface at the pixel (e.g., reducing a height map value for the pixel to zero or another predefined value).

A registration algorithm registers the raw and/or blended scans (that may have been processed by the excess material removal and/or excess gingiva removal algorithms) to each other. In some embodiments, a moving tissue algorithm is not used in the partial retraction scanning mode so as to avoid accidental removal of margin line data. Alternatively, a moving tissue algorithm with stricter criteria than the moving tissue algorithm of the standard preparation scanning mode may be used.

A merging algorithm (also referred to as a stitching algorithm) may then merge together all of the remaining image data of the scans (which may be raw or blended scans) to generate a virtual 3D model of the preparation. For any merging of multiple scans to generate a 3D model, there will inevitably be some differences between those scans that are addressed in some manner. Such differences may be determined by identifying conflicting surfaces between overlapping areas of scans, and then determining whether those conflicting surfaces meet one or more criteria. The merging algorithm may average some differences in data between the scans, and for other differences some data may be discarded. Criteria used to determine whether to average data between scans or to discard data from some of the scans include a size of a conflicting surface, differences in distances (e.g., heights or depths) between the conflicting surfaces in the scans, differences in mean or Gaussian curvature between the conflicting surfaces in the scans, and so on.

The first algorithms may include a first merging algorithm with a first size threshold and a first similarity threshold for determining whether to average together data from conflicting surfaces. The second algorithms may include a second merging algorithm with a second size threshold for determining whether to average together data from conflicting surfaces, where the second size threshold may be larger than the first size threshold. Additionally, the second merging algorithm may include a second similarity threshold that is higher than the first similarity threshold.

The size of a conflicting area may be used to determine whether to perform merging, where the size of the conflicting area must exceed some size threshold or be averaged. Thus, averaging may be performed for areas that are smaller than a threshold size and may not be performed for areas that are larger than or equal to the threshold size in embodiments for the second algorithms.

Additionally, the merging algorithm of the second algorithms may determine which image data to use for specific overlapping regions based on criteria such as distance from a scanner (depth or height) and/or curvature. For example, points from a first scan that have a larger distance from the probe and that have a greater curvature (e.g., a greater mean curvature or greater Gaussian curvature) may be selected and conflicting points from an overlapping second scan with a lower distance and/or a lower curvature may be omitted or removed. In an example, scan data may include height maps, where each height map includes a different value representing height (or conversely depth) for each pixel of the scan. Scans may be registered together, and may be determined to include overlapping pixels. The heights of these overlapping pixels may be compared, and the smaller height value (i.e., greater depth value) from one of the scans may be retained while the larger height value (i.e., smaller depth value) of the other scan may be discarded. Additionally, or alternatively, the mean curvature or Gaussian curvature may be computed for the conflicting surface from each of the scans. The scan having the higher mean curvature or higher Gaussian curvature may be selected for use in depicting that surface area, and the scan with the lower mean curvature data or lower Gaussian curvature for the conflicting surface may not be used for the surface area.

In one embodiment, a difference in the height values of the two scans is determined, and if the difference in height values for the overlapping pixels exceeds a threshold, then the smaller height value is selected. If the difference in height values of the overlapping pixels is less than the threshold, then the height values may be averaged (e.g., with a weighted or non-weighted average). Such computations may be made based on average depth values of some or all of the pixels within a conflicting surface in embodiments.

Accordingly, portions of scan data may be selected for use based on one or more criteria such as size of overlapping area (e.g., number of adjacent overlapping pixels in question), difference in height values for overlapping pixels, and/or differences in mean curvature or Gaussian curvature. For areas that are larger than a size threshold, the data for the areas from a scan that has smaller height values and/or larger mean curvature values may be selected and the data for the areas from another scan that has larger height values and/or smaller mean curvature values may be discarded or erased. This prevents data representing gingiva from being averaged with data representing a margin line, as margin lines are associated with high curvature values and gingiva are associated with much lower curvature values.

In some embodiments, data from a first set of scans is discarded, and data from a second set of scans is averaged together. For example, 7 scans may have an overlapping area with a size that meets or exceeds a size threshold. Data from 4 of the scans depicting the area may be discarded, while data from the remaining 3 scans depicting the area may be averaged. In one embodiment, a percentile is computed for the scans with an overlapping area, and those with height values within a certain percentile value (e.g., $80^{th}$ percentile) may be selected for removal.

Intraoral scan application 115 may generate a 3D model from intraoral images, and may display the 3D model to a user (e.g., a doctor) via a user interface. The 3D model can then be checked visually by the doctor. The doctor can virtually manipulate the 3D model via the user interface with respect to up to six degrees of freedom (i.e., translated and/or rotated with respect to one or more of three mutually orthogonal axes) using suitable user controls (hardware and/or virtual) to enable viewing of the 3D model from any desired direction. The doctor may review (e.g., visually inspect) the generated 3D model of an intraoral site and determine whether the 3D model is acceptable (e.g., whether a margin line of a preparation tooth is accurately represented in the 3D model).

Intraoral scan application 115 may include logic for automatically identifying (e.g., highlighting) a margin line in an image and/or 3D model of a preparation tooth. This may make it easier for the doctor to inspect the margin line for accuracy. Intraoral scan application 115 may additionally mark and/or highlight specific segments of the margin line that are unclear, uncertain, and/or indeterminate. Additionally, or alternatively, intraoral scan application 115 may mark and/or highlight specific areas (e.g., a surface) that is unclear, uncertain and/or indeterminate. For example, segments of the margin line that are acceptable may be shown in a first color (e.g., green), while segments of the margin line that are unacceptable may be shown in a second color (e.g., red). In one embodiment, a first trained machine learning model is used to identify a margin line in a preparation tooth.

If portions of the margin line are determined to be unclear or covered by gingiva, a practitioner may be advised by intraoral scan application 115 to rescan those portions of the margin line. The practitioner may have generated the original set of intraoral scan data used to generate the 3D model of the preparation tooth using a partial retraction technique, and intraoral scan application 115 may have used a partial scanning mode provided by partial retraction scanning module 118 to generate the 3D model. Alternatively, the practitioner may have generated the original set of intraoral scan data used to generate the 3D model of the preparation tooth using a full retraction technique, and intraoral scan application 115 may have used a standard scanning mode provided by standard preparation scanning module 119 to generate the 3D model. In either case, the practitioner may not wish to subject the patient to packing of retraction cord around the preparation tooth to obtain additional scan data of the unclear portions of the margin line. Accordingly, the practitioner may use a partial retraction technique to obtain the intraoral scans of the unclear portions of the margin line, and the partial retraction scanning module 118 may execute a partial retraction scanning mode for the acquisition and/or processing of such intraoral scans. Thus, the amount of time committed for rescanning the preparation tooth and patient discomfort associated with such rescanning may be minimized.

Intraoral scan application 115 may additionally or alternatively include logic for automatically correcting a surface of a tooth in an image and/or 3D model of the tooth and/or for modifying a margin line of a preparation tooth that is unacceptable. This may be referred to as "virtual cleanup" or "sculpting" of the margin line. In one embodiment, a second trained machine learning model is used to modify an image and/or 3D model of a preparation tooth, such as to correct a margin line of the preparation tooth (e.g., to sculpt or perform virtual cleanup of the margin line). An updated margin line (e.g., a virtually cleaned up or sculpted margin line) may be indicated in the modified image and/or the modified 3D model. A doctor may inspect the modified margin line to determine if it is accurate.

In an example, a part of a real margin line of a scanned preparation tooth may not be sufficiently clearly defined in the 3D model. For example, during the initial 3D data collection step, for example via scanning, that resulted in the first 3D virtual model being generated, a part of the physical dental surface may have been covered with foreign material, such as for example saliva, blood, or debris. The part of the physical dental surface may also have been obscured by another element such as for example part of the gums, cheek, tongue, dental instruments, artifacts, etc. Alternatively, for example, during the initial 3D data collection step (e.g., via scanning) that resulted in the first virtual 3D model being generated, the region may have been distorted or otherwise defective and may not properly correspond to a physical dental surface (e.g., due to some defect in the actual scanning process). Automatic correction may be performed to remove the representation of the foreign material and show the underlying tooth surface and/or margin line. If automatic correction of the dental surface and/or margin line was performed, then the obscured region may be created, and the obscuring object may be removed in the 3D model.

A doctor may inspect the 3D model with the marked and/or corrected margin line. Based on the inspection of the marked margin line and/or corrected margin line, the doctor may determine a portion of the 3D model that depicts a segment of the margin line is unsuitable or undesired, and that a remainder of the 3D model is acceptable. Alternatively, or additionally, intraoral scan application 115 may automatically select a portion of the 3D model that depicts an unclear or otherwise unsuitable region of a tooth. The unacceptable portion of the 3D model can correspond, for example, to a part of a real margin line of a scanned preparation tooth that was not sufficiently clearly defined in the 3D model. Via the user interface, a user may mark or otherwise demarcate the unacceptable portion of the 3D model. Alternatively, the unacceptable portion may be demarcated or marked automatically using techniques set forth herein.

Intraoral scan application 115 may then apply eraser logic to delete, erase or otherwise remove the marked portion from the 3D model. All regions other than the marked portion may be locked. For example, a dental procedure of interest may be providing a dental prosthesis, and the deleted or removed part of the 3D model may be part of a margin line of a tooth preparation that exists in a real dental surface, but was not clearly represented in the 3D model (or in the intraoral scan data 135A-N used to create the 3D model).

Intraoral scan application 108 may direct a user to generate one or more additional intraoral images of the dental site corresponding to the portion of the 3D model (and corresponding set or sets of intraoral images) that was deleted or removed. The user may then use the scanner 150 to generate the one or more additional intraoral images (e.g., using a partial retraction scanning technique or a full retraction scanning technique), which at least partially overlaps with previously generated intraoral images. The one or more additional intraoral images may be registered with the 3D model (and/or with the intraoral image data sets used to create the 3D model) to provide a composite of the 3D model and the one or more additional intraoral images. In the composite, the part of the 3D model that was previously deleted/removed is at least partially replaced with a corresponding part of the one or more additional intraoral images. However, the portions of the one or more additional images that are outside of the deleted or removed part of the 3D model may not be applied to the composite or updated 3D model.

Once the doctor (e.g., dentist) has determined that the 3D model is acceptable, the doctor may instruct computing device 105 to send the 3D model to computing device 106 of dental lab 110. Computing device 106 may include a dental modeling application 120 that may analyze the 3D model to determine if it is adequate for manufacture of a dental prosthetic. Dental modeling application 120 may include logic to identify the margin line and/or to modify the surface of one or more dental sites and/or to modify a margin line, as discussed with reference to intraoral scan application 115. If the 3D model is deemed suitable (or can be modified such that it is placed into a condition that is deemed suitable), then the dental prosthetic may be manufactured from the 3D model. If the 3D model cannot be placed into a suitable condition, then instructions may be sent back to the dental office 108 to generate one or more additional intraoral images of one or more regions of the dental site.

FIGS. 2-22 illustrate methods related to intraoral scanning and generation and manipulation of virtual 3D models of dental sites. The methods may be performed by a processing logic that may comprise hardware (e.g., circuitry, dedicated logic, programmable logic, microcode, etc.), software (e.g., instructions run on a processing device to perform hardware simulation), or a combination thereof. In one embodiment, at least some operations of the methods are performed by a computing device executing dental modeling logic, such as dental modeling logic 2550 of FIG. 25. The dental modeling logic 2550 may be, for example, a component of an intraoral scanning apparatus that includes a handheld intraoral scanner and a computing device operatively coupled (e.g., via a wired or wireless connection) to the handheld intraoral scanner. Alternatively, or additionally, the dental modeling logic may execute on a computing device at a dental lab.

For simplicity of explanation, the methods are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

Figure 2A:
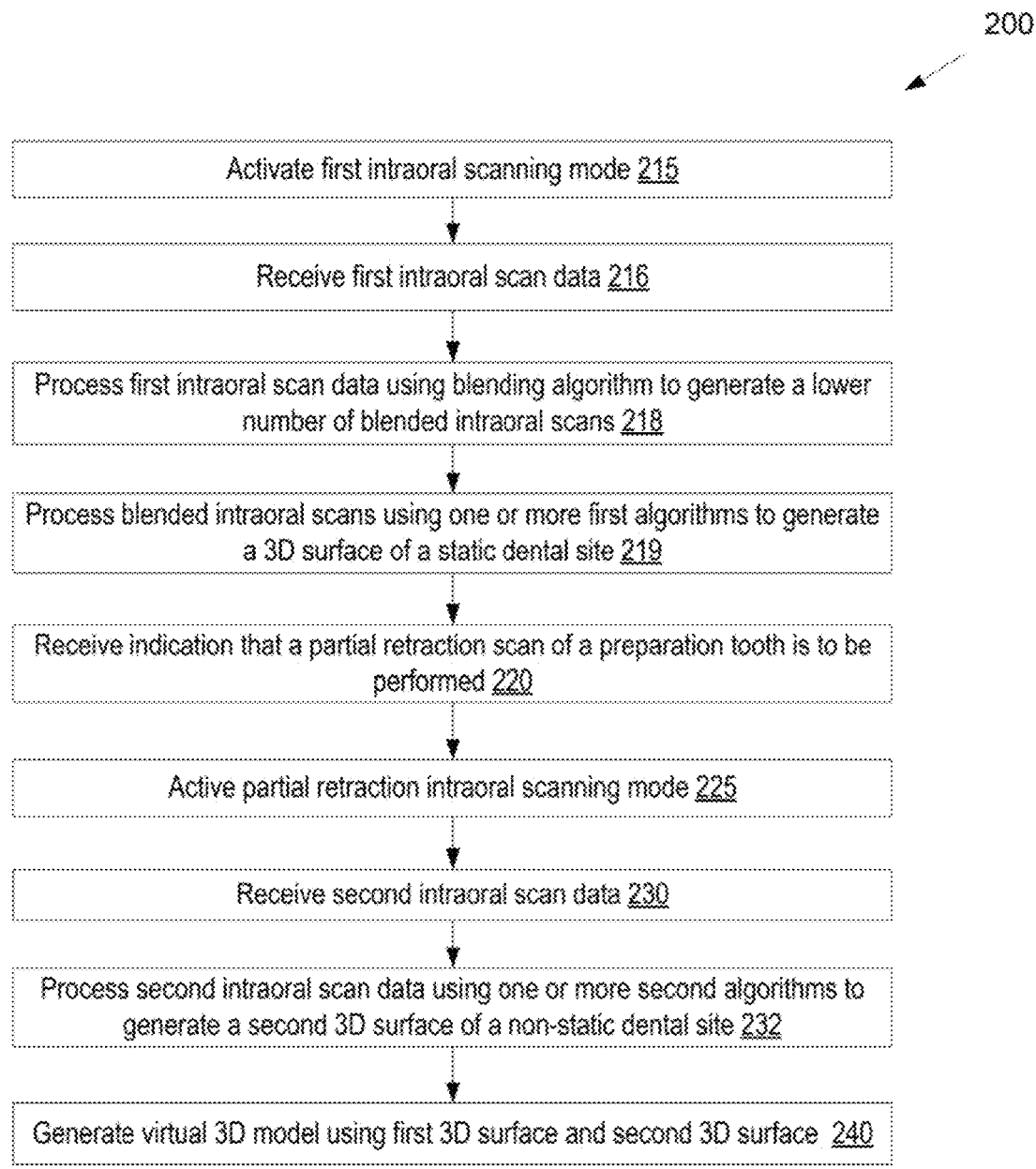
FIG. 2A illustrates a flow diagram for a method of scanning a preparation tooth, in accordance with an embodiment.

FIG. 2A illustrates a flow diagram for a method 200 of scanning a preparation tooth, in accordance with an embodiment. At block 215 of method 200, processing logic activates a first intraoral scanning mode. The first intraoral scanning mode may be, for example, a default intraoral scanning mode that is activated automatically. For example, the standard preparation scanning mode may be a default intraoral scanning mode, and may be activated automatically. Alternatively, a user input may be received selecting the first intraoral scanning mode.

At block 216, processing logic receives first intraoral scan data. The first intraoral scan data may include a sequence of intraoral scans, which may be consecutive and/or raw intraoral scans. The first intraoral scan data may be received during an intraoral scanning session shortly after the first intraoral scan data was generated by an intraoral scanner and while the intraoral scanner continues to generate additional intraoral scan data in embodiments.

At block 218, processing logic processes the first intraoral scan data using a blending algorithm to generate a lower number of blended intraoral scans. At block 219, processing logic processes the blended intraoral scans using one or more first algorithms to generate a 3D surface of a static dental site. The dental site may be static in the sense that no clinically significant changes occur at the dental site within a minimum time period (e.g., within a 30 second time period, within a 1 minute time period, within a 2 minute time period, etc.). A preparation tooth which has been prepared by packing the gingiva around the tooth with packing cord and then removing the packing cord to expose the sub-gingival margin line is considered to be a static dental site because of the rate at which the gingiva collapses back over the gingiva after such a procedure has been performed. The one or more first algorithms may correspond, for example, to the first algorithms of standard preparation scanning module 119 described with reference to FIG. 1. The first dental site may be or include, for example, an upper dental arch and/or a lower dental arch of a patient. The first dental site (e.g., one of the dental arches) may include a preparation tooth thereon, where the preparation tooth includes a sub-gingival margin line. Alternatively, a doctor may have scanned all of the dental site (e.g., the dental arch) except for the preparation tooth. In either case, there may be insufficient detail of the margin line.

At block 220, processing logic receives an indication that a partial retraction scan of a preparation tooth is to be performed. The indication may or may not identify the specific preparation tooth that is to be scanned. If the specific preparation tooth is not identified by the doctor, then processing logic may later automatically identify the preparation tooth based on the shape of the preparation tooth and/or surrounding surfaces around the preparation tooth (e.g., adjacent teeth). In alternative embodiments, an indication that a partial retraction scan of the preparation tooth was performed may be received after receiving the second intraoral scan data. In further embodiments, processing logic may automatically determine that a partial retraction scanning technique was used to scan the preparation tooth based on analysis of second intraoral scan data received at block 230 (and the partial retraction intraoral scanning mode may be activated after receiving and analyzing the second intraoral scan data).

At block 225, processing logic activates a partial retraction intraoral scanning mode. At block 230, processing logic receives second intraoral scan data. The second intraoral scan data may be a sequence of intraoral scans of the preparation tooth. The sequence of intraoral scans may have been generated while a doctor applies a partial retraction intraoral scanning technique as discussed herein above. For example, the doctor exposes just a small portion of the margin line for the preparation tooth at a time by using a tool to retract a small region of the gingiva around the preparation tooth, and generates one or more scan of that small portion of the margin line and surrounding surfaces while that small portion of the margin line is exposed. The doctor then moves the tool, exposes a new portion of the margin line by retracting a new region of the gingiva, and generates one or more additional scan of the newly exposed portion of the margin line. The doctor continues this process until scans are generated for all portions of the margin line.

At block 232, processing logic processes the second intraoral scan data using one or more second algorithms to generate a second 3D surface of a non-static dental site. In this example, the non-static dental site is the preparation tooth with the exposed margin line and gingiva around the preparation tooth. Since a different portion of the margin line is exposed and a different portion of the gingiva is retracted in each set of intraoral scans included in the second intraoral scan data, the preparation tooth is considered to be a non-static dental site. Accordingly, the first algorithms used to process the first intraoral scan data at block 219 may not generate an accurate depiction of the margin line due to the non-static nature of the gingiva and margin line received at block 230. Accordingly, the one or more second algorithms are used at block 232, which may be configured to operate on scan data of a non-static dental site. The one or more second algorithms may correspond, for example, to the second algorithms of partial retraction scanning module 118 described with reference to FIG. 1. In one embodiment, no blending algorithm is used to generate blended scans for the partial retraction intraoral scanning mode and/or moving tissue detection algorithm is used. Alternatively, blended scans may be generated for the partial retraction intraoral scanning mode and/or a moving tissue detection algorithm that has been configured so as not to classify changing gingiva as moving tissue is used.

In one embodiment, processing the second intraoral scan data (which may include a plurality of intraoral scans) using the one or more second algorithms includes determining a conflicting surface for a pair of intraoral scans from the second intraoral scan data. This may be performed as part of a merging algorithm. A first intraoral scan of the pair of intraoral scans may have a first distance from a probe of an intraoral scanner for the conflicting surface and a second intraoral scan of the pair of intraoral scans may have a second distance from the probe of the intraoral scanner for the conflicting surface. Processing logic then determines which of the distances is greater. For example, processing logic may determine that the first distance is greater than the second distance. Processing logic additionally determines a difference between the two distances, and determines whether the difference between the first distance and the second distance is greater than a difference threshold. Responsive to determining that the difference is greater than the difference threshold, processing logic discards a representation of the conflicting surface from the intraoral scan with the smaller distance (e.g., from the first intraoral scan in the above example). The second 3D surface of the non-static dental site (e.g., of the preparation tooth) may then be determined by combining data from the first intraoral scan and the second intraoral scan, wherein the discarded representation of the conflicting surface from the first intraoral scan is not used to determine the surface. If the difference is less than the difference threshold, then the data for the conflicting surface from the two intraoral scans may be averaged together.

In one embodiment, processing the second intraoral scan data using the one or more algorithms configured to determine a three-dimensional surface of a non-static dental site further comprises determining a conflicting surface for a pair of intraoral scans from the second intraoral scan data. This may be performed as part of a merging algorithm. Processing logic then determines a first mean curvature or Gaussian curvature for the conflicting surface from a first intraoral scan from the pair. Processing logic additionally determines a second mean curvature or Gaussian curvature for the conflicting surface from a second intraoral scan from the pair. Processing logic then determines which of the mean curvatures is greater (e.g., processing logic may determine that the second mean curvature is less than the first mean curvature). Processing logic may additionally determine a difference between the two mean or Gaussian curvatures, and determines whether the difference between the first mean or Gaussian curvature and the second mean or Gaussian curvature is greater than a difference threshold. Responsive to determining that the difference is greater than the difference threshold, processing logic discards a representation of the conflicting surface from the intraoral scan with the smaller mean or Gaussian curvature (e.g., from the first intraoral scan in the above example). The second 3D surface of the non-static dental site (e.g., of the preparation tooth) may then be determined by combining data from the first intraoral scan and the second intraoral scan, wherein the discarded representation of the conflicting surface from the first intraoral scan is not used to determine the surface. If the difference is less than the difference threshold, then the data for the conflicting surface from the two intraoral scans may be averaged together.

In some embodiments, both the distances and mean or Gaussian curvatures are determined for conflicting surfaces, and these values are used together to determine which scan data to discard. In one embodiment, conflicting surface data is averaged together if both the difference between distances is below a distance difference threshold and the difference between mean curvatures or Gaussian curvatures is below a curvature difference threshold. If either the distance difference is greater than the distance difference threshold or the mean or Gaussian curvature is greater than the curvature difference threshold, then the associated data from one of the two scans is discarded as described above.

In one embodiment, processing the second intraoral scan data using the one or more second algorithms includes inputting intraoral scans of the second intraoral scan data into a trained machine learning model that has been trained to identify excess gingiva. For example, a height map representing the surface of the non-static dental site may be input into a machine learning model that has been trained to identify portions of gingiva that overlie a margin line, wherein the machine learning model outputs an indication of the portions of the gingiva that overlie the margin line. This output may be in the form of a map or mask of the same resolution as the input height map, where each pixel of the map or mask includes an indication as to whether or not that pixel represents excess gingiva. Processing logic may then hide or remove, from the height map, data associated with the portions of the gingiva that overlie the margin line (i.e., those pixels that were identified as excess gingiva). In one embodiment, the machine learning model outputs a probability map comprising, for each pixel in the height map, a first probability that the pixel belongs to a first dental class and a second probability that the pixel belongs to a second dental class, wherein the first dental class represents portions of gingiva that overlie a margin line. Processing logic may then determine, based on the probability map, one or more pixels in the height map that are classified as portions of gingiva that overlie a margin line (i.e., excess gingiva).

At block 240, processing logic generates a virtual 3D model using the first 3D surface of the static dental site determined from the first intraoral scan data and the second 3D surface of the non-static dental site determined from the second intraoral scan data. In instances where the static dental site includes the non-static dental site (e.g., the static dental site is a dental arch and the non-static dental site is a preparation tooth on the dental arch), the portion of the 3D surface of the dental site that depicts the non-static dental site may be erased or omitted and replaced by the 3D surface of the non-static dental site.

Figure 2B:
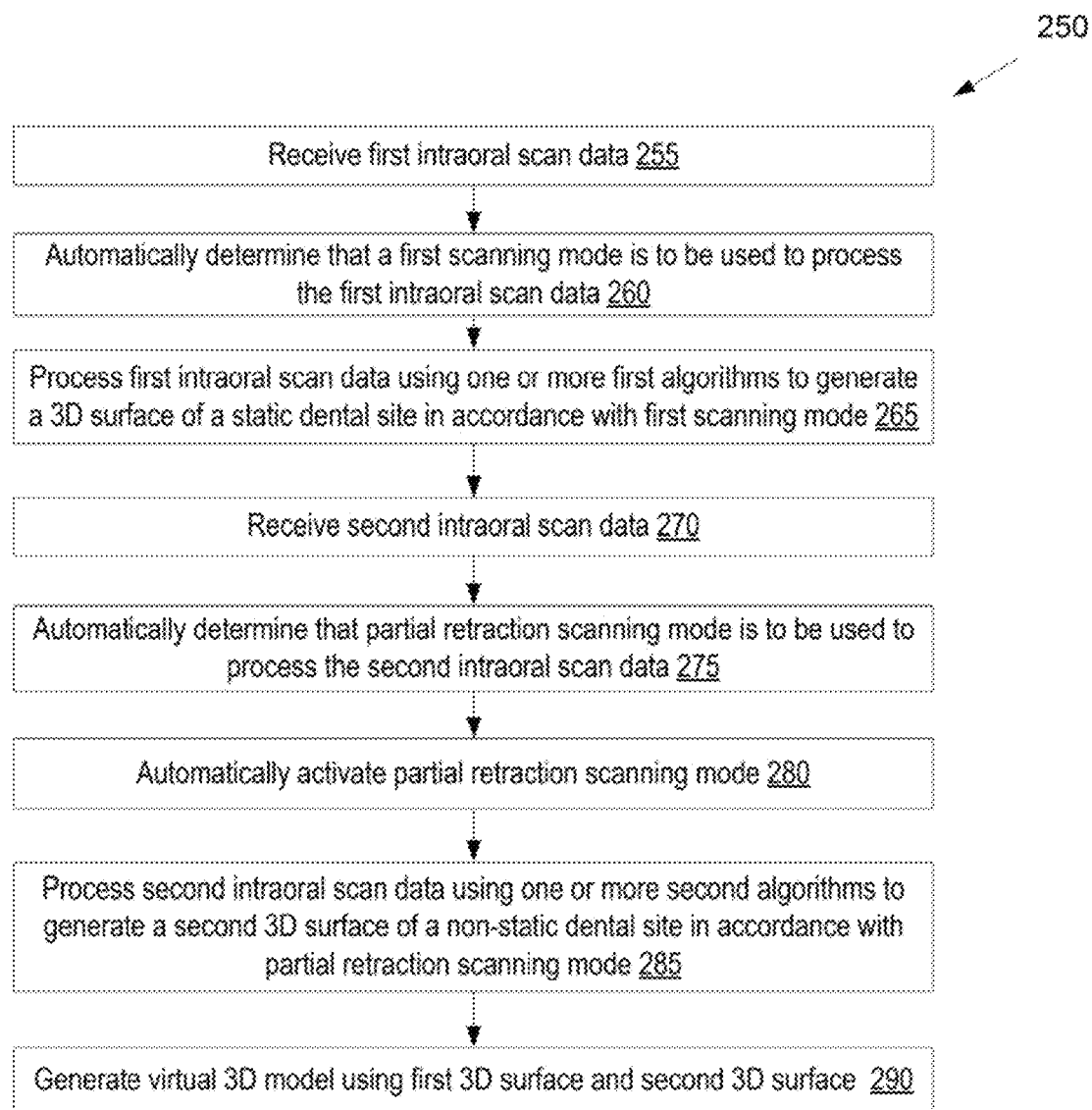
FIG. 2B illustrates a flow diagram for a method of using two different scanning modes for scanning a preparation tooth, in accordance with an embodiment.

FIG. 2B illustrates a flow diagram for a method 250 of using two different scanning modes for scanning a preparation tooth, in accordance with an embodiment. At block 255 of method 250, processing logic receives first intraoral scan data. At block 260, processing logic automatically determines that a first scanning mode is to be used to process the first intraoral scan data. For example, processing logic may determine based on analysis of the first intraoral scan data that it was generated using a standard scanning technique, and that a standard intraoral scanning mode is to be used to process the first intraoral scan data. For example, if there is less than a threshold difference between overlapping regions of sequentially generated scans, then it may be determined that the standard intraoral scanning mode should be used. At block 265, processing logic processes the first intraoral scan data using one or more first algorithms to generate a 3D surface of a static dental site (e.g., of a dental arch or a portion of a dental arch) in accordance with the first scanning mode.

At block 270, processing logic receives second intraoral scan data. At block 275, processing logic automatically determines that a second scanning mode (e.g., the partial retraction scanning mode) is to be used to process the second intraoral scan data. For example, processing logic may determine based on analysis of the second intraoral scan data that it was generated using a partial retraction scanning technique, and that a partial retraction intraoral scanning mode is to be used to process the second intraoral scan data. Such a determination may be made, for example, based on comparison of intraoral images (e.g., sequentially generated images) from the second intraoral scan data and determining that differences there between exceed a threshold. For example, height maps from the second intraoral scan data may be registered to each other, and conflicting surfaces may be determined there between. The differences may be compared to one or more thresholds, and if a threshold percentage of the differences exceed a difference threshold, then processing logic may determine that the second intraoral scanning mode is to be used. At block 280, processing logic may automatically activate the second scanning mode (e.g., the partial retraction scanning mode). At block 285, processing logic processes the second intraoral scan data using one or more second algorithms to generate a 3D surface of a non-static dental site (e.g., of a preparation tooth) in accordance with the second scanning mode (e.g., the partial retraction scanning mode). At block 290, processing logic generates a virtual 3D model using the first 3D surface and the second 3D surface.

Figure 3:
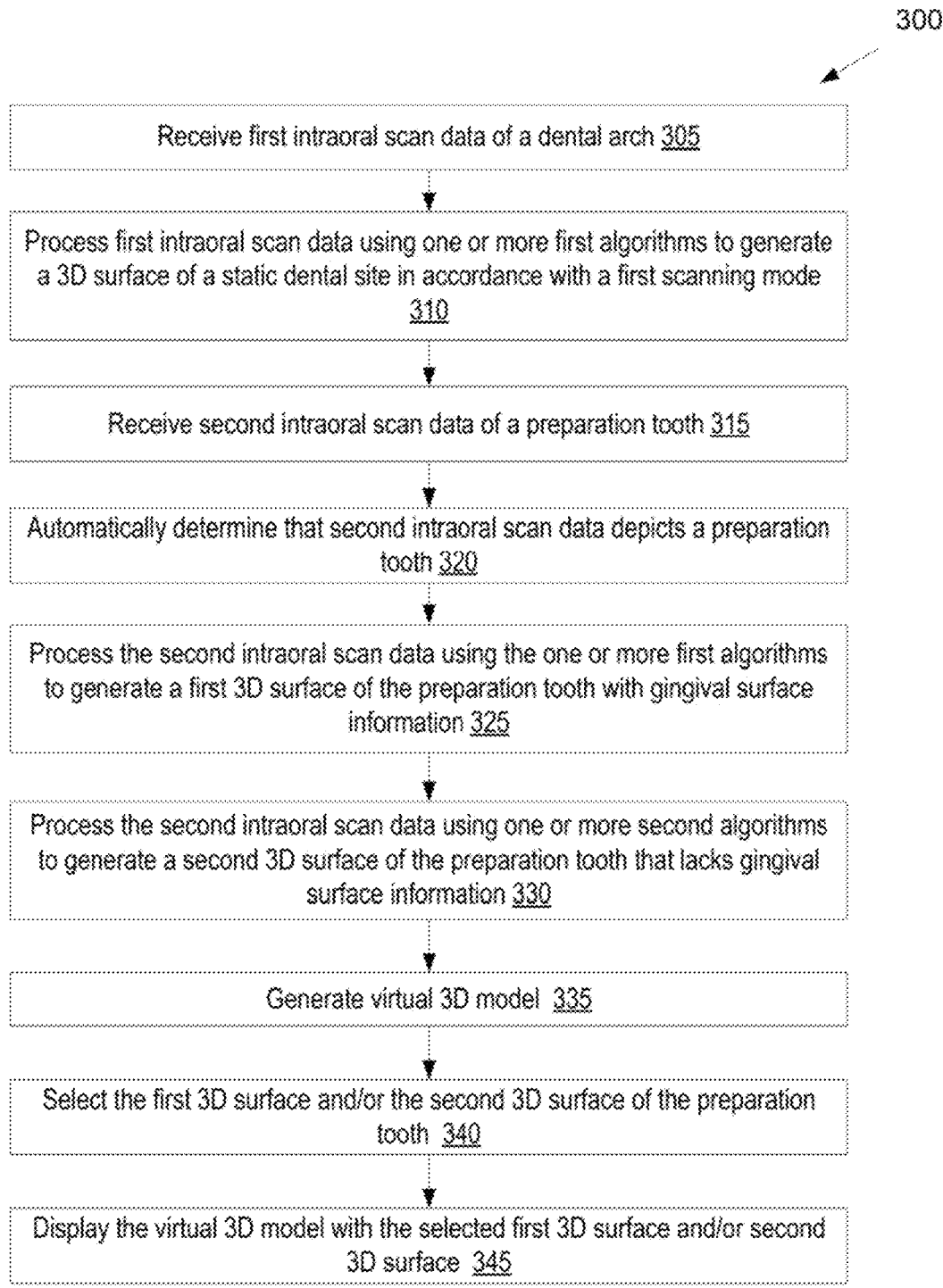
FIG. 3 illustrates a flow diagram for a method of processing intraoral scan data to generate a virtual 3D model of a preparation tooth, in accordance with an embodiment.

FIG. 3 illustrates a flow diagram for a method 300 of processing intraoral scan data to generate a virtual 3D model of a preparation tooth, in accordance with an embodiment. At block 305 of method 300, processing logic receives first intraoral scan data of a dental arch. At block 310, processing logic processes the first intraoral scan data using one or more first algorithms to generate a 3D surface of a static dental site (e.g., of a dental arch or a portion of a dental arch) in accordance with a first scanning mode (e.g., a standard scanning mode).

At block 315, processing logic receives second intraoral scan data. At block 320, processing logic automatically determines that the second intraoral scan data depicts a preparation tooth. Such a determination may be made based on processing of the second intraoral scan data using a machine learning model that has been trained to identify preparation teeth. Alternatively, one or more rule-based algorithms may be used to process the second intraoral scan data, and may determine that the second intraoral scan data depicts a preparation tooth based on the second intraoral scan data satisfying criteria of the one or more rule-based algorithms. For example, preparation teeth may have a shape that does not naturally occur in the mouth. A shape of a dental site represented in the second intraoral scan data may be analyzed using the rule-based algorithm to determine that it meets the criteria for a preparation tooth.

At block 325, processing logic processes the second intraoral scan data using the one or more first algorithms in accordance with the first scanning mode. The generated first 3D surface includes depictions of the preparation tooth and of a surrounding gingival surface that covers at least a portion of a margin line of the preparation tooth.

At block 330, processing logic also processes the second intraoral scan data using one or more second algorithms of a second intraoral scanning mode to generate a second 3D surface of the preparation tooth. The second 3D surface may include a depiction of the preparation tooth and optionally of surrounding gingiva, but the second 3D surface may not include a depiction of any excess gingiva that overlies a margin line of the preparation tooth.

At block 335, processing logic generates a virtual 3D model of the dental site. At block 340, the first 3D surface or the second 3D surface is selected for the preparation tooth. In one embodiment, a first option for using the first 3D surface and a second option for using the second 3D surface are presented to a user for selection. Each option may be accompanied by a version of a 3D model of the dental site, showing what the 3D model will look like if that option is selected. The user (i.e., the doctor) may then select the option that he or she prefers. Alternatively, processing logic may automatically determine which version of the virtual 3D model has the clearest depiction of the margin line, and may select that option. At block 345, processing logic displays the virtual 3D model with the selected first 3D surface or the selected second 3D surface.

Figure 4A:
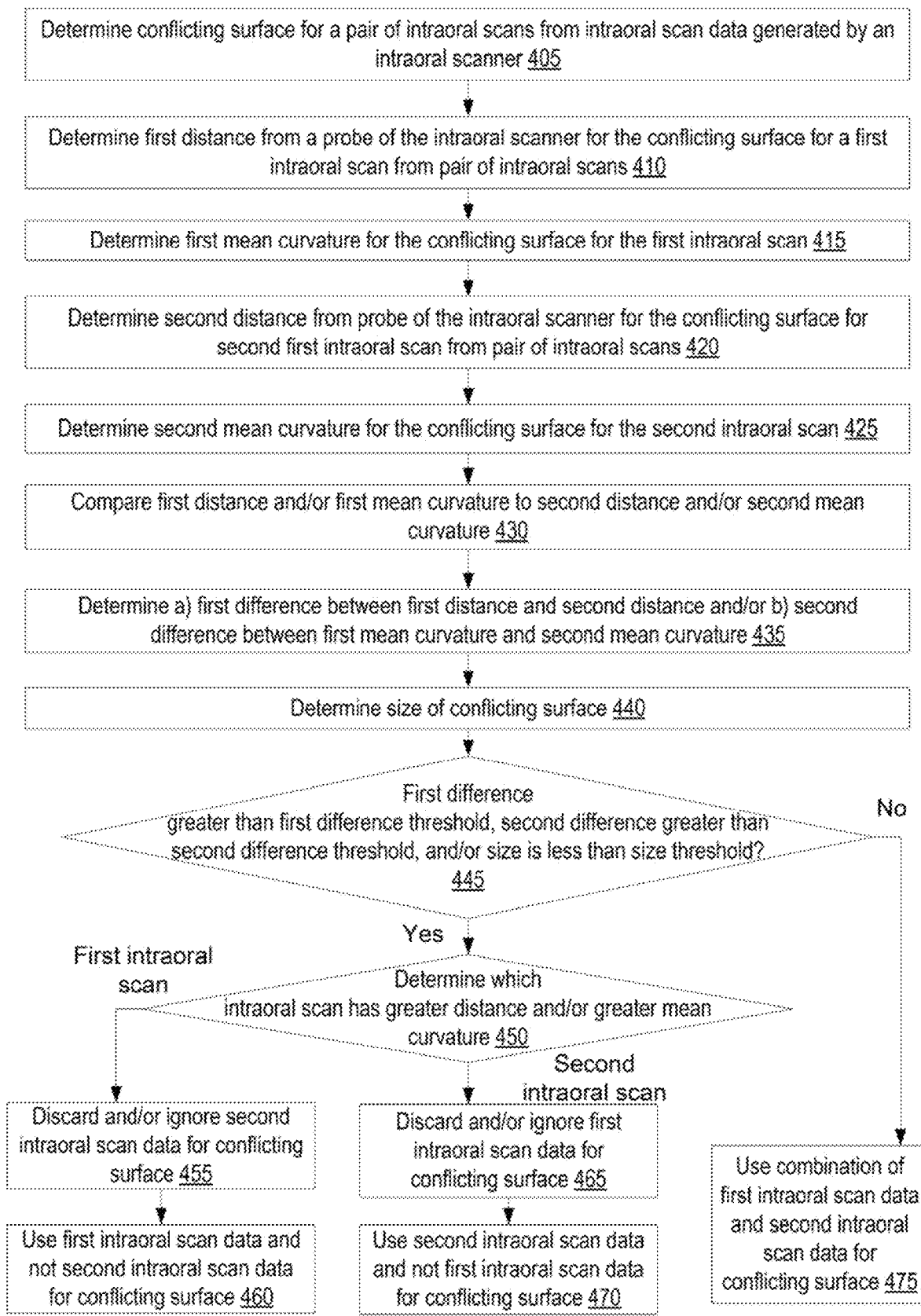
FIG. 4A illustrates a flow diagram for a method of resolving conflicting scan data of a dental site, in accordance with an embodiment.

FIG. 4A illustrates a flow diagram for a method 400 of resolving conflicting scan data of a dental site, in accordance with an embodiment. Method 400 may be performed by the one or more second algorithms of partial retraction scanning module 118 of FIG. 1 to select which scan data to keep and which scan data to discard for conflicting surfaces. In one embodiment, the partial retraction scanning module 118 performs method 400 as part of a stitching and/or merging algorithm used to generate a 3D surface from a plurality of intraoral scans. In one embodiment, processing logic determines that a partial retraction scan of a first preparation tooth will be performed or has been performed, wherein the partial retraction scan comprises an intraoral scan of a preparation tooth that has not been packed with a gingival retraction cord. Processing logic receives a plurality of intraoral scans generated by an intraoral scanner (before or after making the determination that the partial retraction scanning technique was performed), and processes the plurality of intraoral scans using a stitching or merging algorithm to stitch together the plurality of intraoral scans in accordance with a partial retraction intraoral scanning mode. In one embodiment, the stitching algorithm (also referred to as a merging algorithm) executes method 400.

At block 405 of method 400, processing logic determines a conflicting surface for a pair of intraoral scans from intraoral scan data generated by an intraoral scanner. At block 410, processing logic determines a first distance from a probe of the intraoral scanner (also referred to as a first depth and/or first height) for the conflicting surface for a first intraoral scan of the pair of intraoral scans. The first depth may be a combined depth value (e.g., an average depth or media depth) based on the depths of some or all pixels of the first intraoral scan that are included in the conflicting surface. At block 415, processing logic determines a first mean curvature (or a first Gaussian curvature) for the conflicting surface for the first intraoral scan. At block 420, processing logic determines a second distance from the probe of the intraoral scanner (also referred to as a second depth and/or second height) for the conflicting surface for a second intraoral scan of the pair of intraoral scans. The second depth may be a combined depth value (e.g., an average depth or media depth) based on the depths of some or all pixels of the second intraoral scan that are included in the conflicting surface. At block 425, processing logic determines a second mean curvature (or a second Gaussian curvature) for the conflicting surface for the second intraoral scan.

At block 430, processing logic compares the first distance and/or the first mean curvature (or first Gaussian curvature) to the second distance and/or the second mean curvature (or second Gaussian curvature). At block 435, processing logic determines a) a first difference between the first distance and the second distance and/or b) a second difference between the first mean curvature (or second Gaussian curvature) and the second mean curvature (or second Gaussian curvature). At block 440, processing logic determines a size of the conflicting surface.

At block 445, processing logic determines one or more of the following: a) whether the first difference is greater than a first difference threshold, b) whether the second difference is greater than a second difference threshold, c) whether the size of the conflicting surface is less than an upper size threshold. Processing logic may also determine whether the size is greater than a lower size threshold. If the first difference is less than the first difference threshold, the second difference is less than the second difference threshold, the size is less than the upper size threshold, and/or the size is greater than the lower size threshold, then the method proceeds to block 475. In one embodiment, the method proceeds to block 475 if the first difference is greater than the first difference threshold and the size of the conflicting surface is within a particular size range (e.g., smaller than an upper size threshold and/or larger than a lower size threshold). In one embodiment, the method proceeds to block 475 if the first difference is greater than the first difference threshold, the second difference is greater than the second difference threshold, and the size of the conflicting surface is within a particular size range. Otherwise, the method continues to block 450.

At block 475, processing logic uses a combination of the first intraoral scan data and the second intraoral scan data for the conflicting surface. This may include, for example, averaging the first intraoral scan data with the second intraoral scan data for the conflicting surface. The first and second intraoral scan data may be averaged with a weighted or non-weighted average. For example, the intraoral scan with the greater distance measurement (e.g., greater height measurement or lesser depth measurement) may be assigned a higher weight than the intraoral scan with the lesser distance measurement (e.g., lesser height measurement or greater depth measurement).

At block 450, processing logic determines which of the intraoral scans has a greater distance and/or a greater mean curvature (or greater Gaussian curvature) for the conflicting surface. If the first intraoral scan has a greater distance and/or a greater mean curvature than the second intraoral scan for the conflicting surface, then the method continues to block 455. If the second intraoral scan has a greater distance and/or a greater mean curvature than the first intraoral scan for the conflicting surface, then the method continues to block 465.

At block 455, processing logic discards and/or ignores the second intraoral scan data for the conflicting surface. At block 460, processing logic uses the first intraoral scan data and not the second intraoral scan data for the conflicting surface when generating a 3D surface for a virtual 3D model of the dental site that was scanned.

At block 465, processing logic discards and/or ignores the first intraoral scan data for the conflicting surface. At block 470, processing logic uses the second intraoral scan data and not the first intraoral scan data for the conflicting surface when generating the 3D surface for the virtual 3D model of the dental site that was scanned.

Figure 4B:
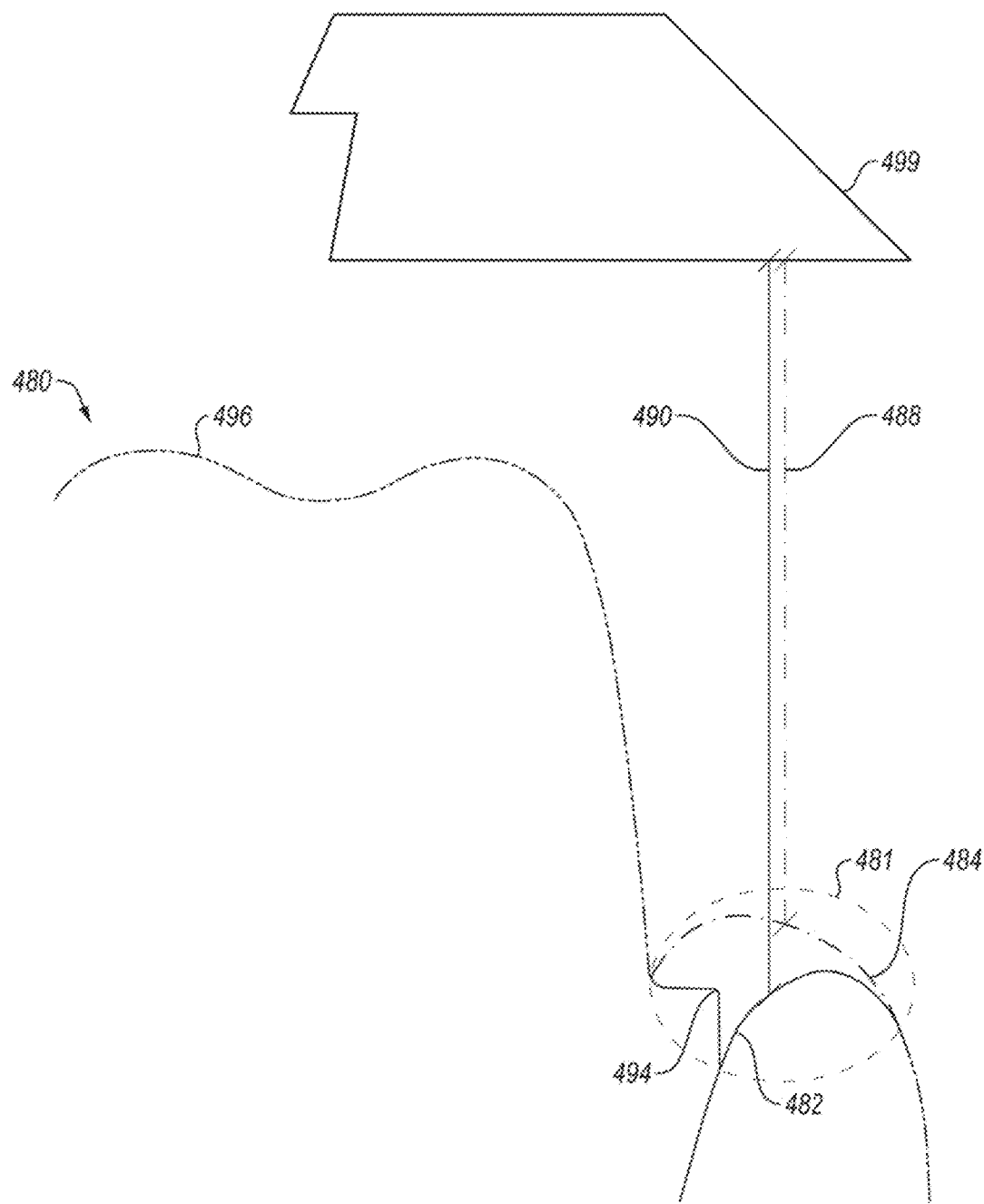
FIG. 4B illustrates resolution of conflicting scan data of a dental site, in accordance with an embodiment.

FIG. 4B illustrates resolution of conflicting scan data of a dental site that includes a preparation tooth and surrounding gingiva, in accordance with an embodiment. In FIG. 4B, a dental site 480 is scanned by an intraoral scanner. The conflicting scan data includes data of a first scan that was taken while a margin line 494 was exposed and data of a second scan that was taken while the margin line 494 was covered by gingiva. The first scan shows surfaces 482, 496, which includes exposed margin line 494. The second scan shows surfaces 496, 484, which includes gingiva that overlies the margin line. The margin line is not detected in the second scan. A conflicting surface 481 may be determined based on comparison between the two scans.

For the first scan, a first distance 490 from the probe is determined for the conflicting surface 481. The first distance may be an average distance from the probe for surface 482 in one embodiment. However, a first distance 490 for a particular point on surface 482 is illustrated for the purposes of clarity. For the second scan, a second distance 488 from the probe is determined for surface 484. The second distance may be an average distance of the second scan for the surface 484. However, a second distance 488 for a particular point is illustrated for the purposes of clarity. As described with reference to FIG. 4A, the first and second distances may be compared, and a difference between these distances may be computed. Processing logic may determine that the first difference is greater than a difference threshold, and that the first distance 490 is greater than the second distance 488. The second scan data for the conflicting surface 481 may then be discarded so that the 3D model that is generated depicts the margin line 494.

A first mean curvature may also be computed for the first surface 482 of the conflicting surface 481 and a second mean curvature may be computed for the second surface 484 of the conflicting surface 481. As shown, the first surface 482 would have a greater mean curvature than the second surface 484. The first and second mean curvatures may be compared, and the result of the comparison may be used as an additional data point to determine which of the scans should be used to depict the conflicting surface, as described with reference to FIG. 4A.

FIG. 5A illustrates a flow diagram for a partial retraction method 500 of scanning a preparation tooth, in accordance with an embodiment. At block 505 of method 500, processing logic receives a first intraoral scan of a preparation tooth after a gingival retraction tool has momentarily retracted a first portion of a gingiva surrounding the preparation tooth to partially expose a margin line. The first portion of the margin line is exposed in the first intraoral scan. At block 510, processing logic receives a second intraoral scan of the preparation tooth after receiving the first intraoral scan. In the second intraoral scan, the first portion of the margin line is obscured by the first portion of the gingiva. For example, the gingival retraction tool may have been moved to expose a different portion of the margin line, letting the gingiva collapse back over the first portion of the margin line when the second intraoral scan was generated.

At block 515, processing logic compares the first intraoral scan to the second intraoral scan. At block 520, processing logic identifies, between the first intraoral scan and the second intraoral scan, a conflicting surface at a region of the preparation tooth corresponding to the first portion of the margin line. At block 522, processing logic determines that the conflicting surface satisfies scan selection criteria. The scan selection criteria may include, for example, any of the criteria described with reference to FIGS. 4A-4B. For example, the scan selection criteria may include a first criterion that an average distance difference between the scans for the conflicting surface area be greater than a distance difference threshold. The scan selection criteria may further include a second criterion that the scan with the larger average distance be selected. The scan selection criteria may further include a third criterion that the scan with the larger mean curvature be selected. Other criteria may also be used.

At block 525, processing logic discards or marks data for the region of the preparation tooth associated with the conflicting surface from the second intraoral scan. At block 530, processing logic stitches together the first intraoral scan and the second intraoral scan to generate a virtual model of the preparation tooth. Data for the region of the preparation tooth from the first intraoral scan is used to generate the virtual model of the preparation tooth, and data for the region of the preparation tooth from the second intraoral scan is not used to generate the virtual model of the preparation tooth.

FIG. 5B illustrates another flow diagram for a partial retraction method 550 of scanning a preparation tooth, in accordance with an embodiment. In one embodiment, method 550 is performed after receiving an indication that a partial retraction scan will be performed, and activating a partial retraction intraoral scanning mode.

At block 555 of method 550, processing logic receives a first intraoral scan of a preparation tooth after a gingival retraction tool has momentarily retracted a first portion of a gingiva surrounding the preparation tooth to partially expose a margin line, wherein a first portion of the margin line is exposed in the first intraoral scan, and wherein a second portion of the margin line is obscured by the gingiva in the first intraoral scan. At block 560, processing logic receives a second intraoral scan of the preparation tooth after the gingival retraction tool has momentarily retracted a second portion of the gingiva surrounding the preparation tooth to partially expose the margin line, wherein the second portion of the margin line is exposed in the second intraoral scan, and wherein the first portion of the margin line is obscured by the gingiva in the second intraoral scan. At block 565, processing logic generates a virtual model of the preparation tooth using the first intraoral scan and the second intraoral scan, wherein the first intraoral scan is used to generate a first region of the virtual model representing the first portion of the margin line, and wherein the second intraoral scan is used to generate a second region of the virtual model representing the second portion of the margin line. In one embodiment, a third portion of the margin line is exposed in the first intraoral scan and in the second intraoral scan, and both the first intraoral scan and the second intraoral scan are used to generate a third region of the virtual model representing the third portion of the margin line.

Figure 5D:
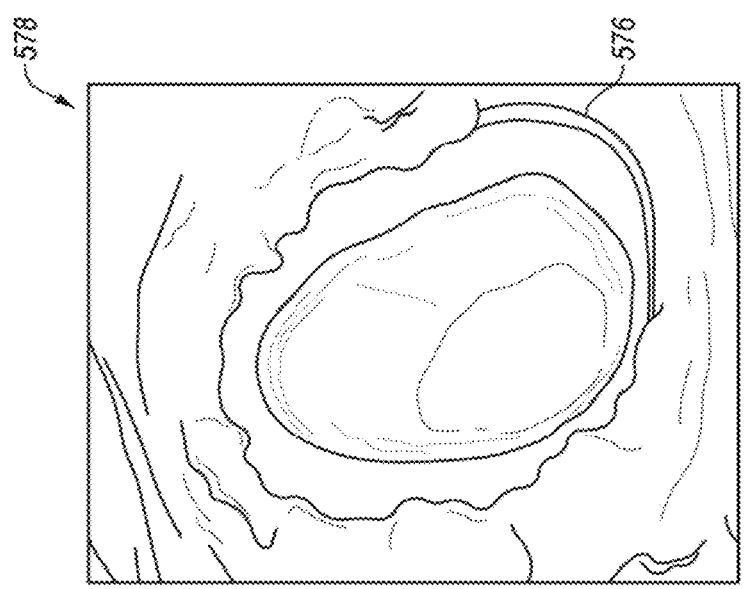
FIGS. 5C-G illustrates a partial retraction method of scanning a preparation tooth, in accordance with an embodiment.
Figure 5C:
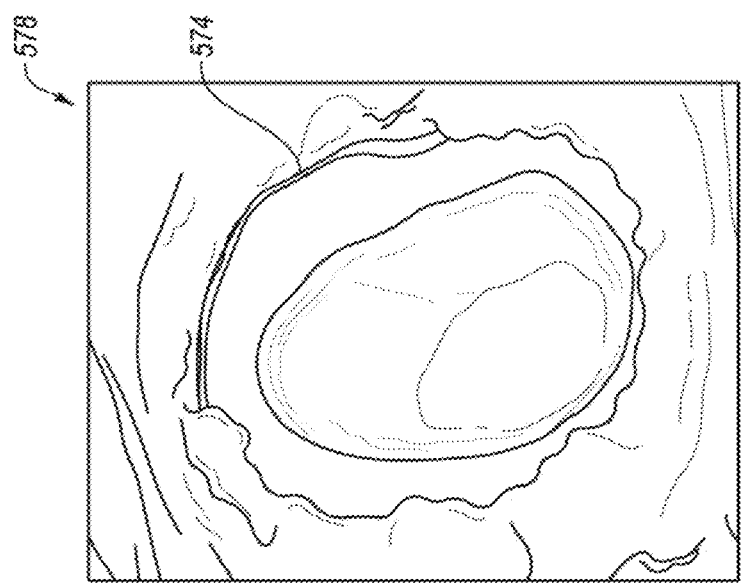
Figure 5G:
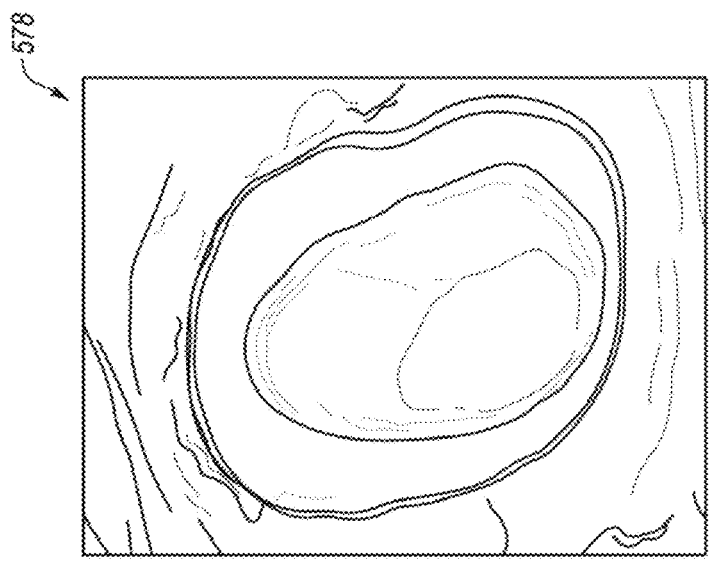
Figure 5F:
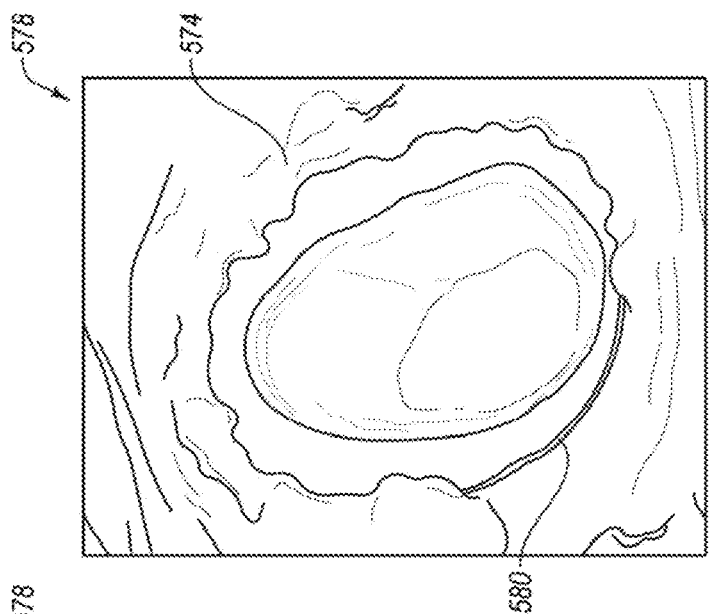
Figure 5E:
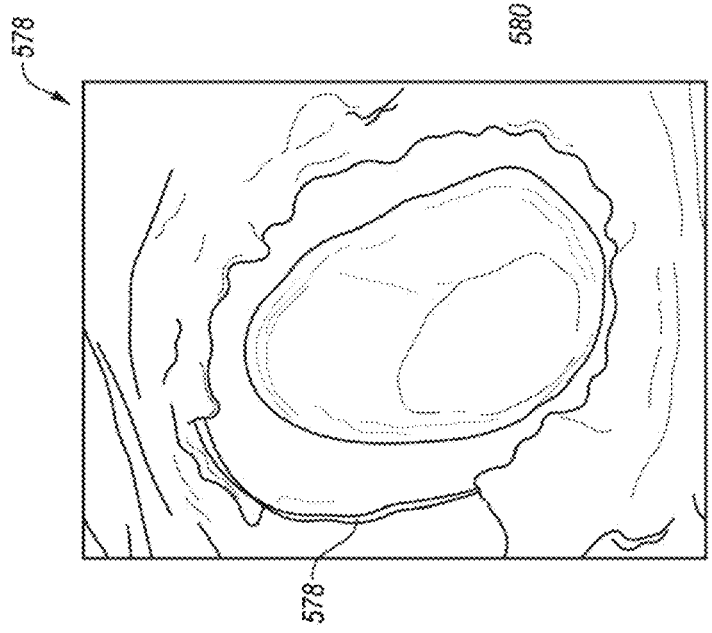

FIGS. 5C-G illustrate a partial retraction method of scanning a preparation tooth, in accordance with an embodiment. FIG. 5C illustrates a first view of a preparation tooth as depicted in first intraoral scan data 570 generated while a first region of a margin line was exposed. FIG. 5D illustrates a second view of the preparation tooth as depicted in second intraoral scan data 578 generated while a second region of the margin line was exposed. FIG. 5E illustrates a third view of the preparation tooth as depicted in third intraoral scan data 584 generated while a third region of the margin line was exposed. FIG. 5F illustrates a fourth view of the preparation tooth as depicted in fourth intraoral scan data 590 generated while a fourth region of the margin line was exposed. FIG. 5G illustrates a 3D model 595 of the preparation tooth generated using selected portions of first intraoral scan data 570, second intraoral scan data 578, third intraoral scan data 584 and fourth intraoral scan data 590. The selected portions are those respective portions showing the exposed margin line in each of the first intraoral scan data 570, second intraoral scan data 578, third intraoral scan data 584 and fourth intraoral scan data 590.

FIG. 6A illustrates a flow diagram for a method 600 of resolving an obscured margin line for a preparation tooth, in accordance with an embodiment. At block 605 of method 600, processing logic receives a first intraoral scan of a preparation tooth after a retraction cord that was packed around the preparation tooth was removed to expose a margin line. At block 610, processing logic generates a first surface for the preparation tooth using the first intraoral scan data and a first one or more algorithms (e.g., in accordance with a standard scanning mode). At block 615, processing logic determines whether, for a portion of the first surface depicting a portion of the preparation tooth, the margin line is obscured by gum tissue. At block 620 if the margin line is obscured by gum tissue, the method moves on to block 630. Otherwise the method continues to block 625 and the surface is accepted.

At block 630, processing logic generates a second surface for the portion of the preparation tooth in which the margin line was obscured by the gingiva using the first intraoral scan data and a second one or more algorithms (e.g., in accordance with a partial retraction scanning mode). At block 635, processing logic determines whether, for the second surface depicting the portion of the preparation tooth, the margin line is obscured by gum tissue. At block 640 if the margin line is obscured by gum tissue, the method moves on to block 650. Otherwise the method continues to block 645 and the portion of the first surface generated using the first one or more algorithms at block 610 is replaced with the second surface. In one embodiment, the operations of blocks 630-645 are omitted, and the method proceeds directly from block 620 to block 650 if the margin line is determined to be obscured at block 620.

At block 650, processing logic receives second intraoral scan data in which the margin line is exposed at the portion of the preparation tooth. The second intraoral scan data may be received after a gingival retraction tool has momentarily retracted a portion of a gingiva above the portion of the preparation tooth to expose the margin line at the portion of the preparation tooth. At block 655, processing logic generates a third surface for the portion of the preparation tooth using the second intraoral scan data and the second one or more algorithms. At block 660, processing logic replaces the portion of the first surface with the third surface.

Figure 6B:
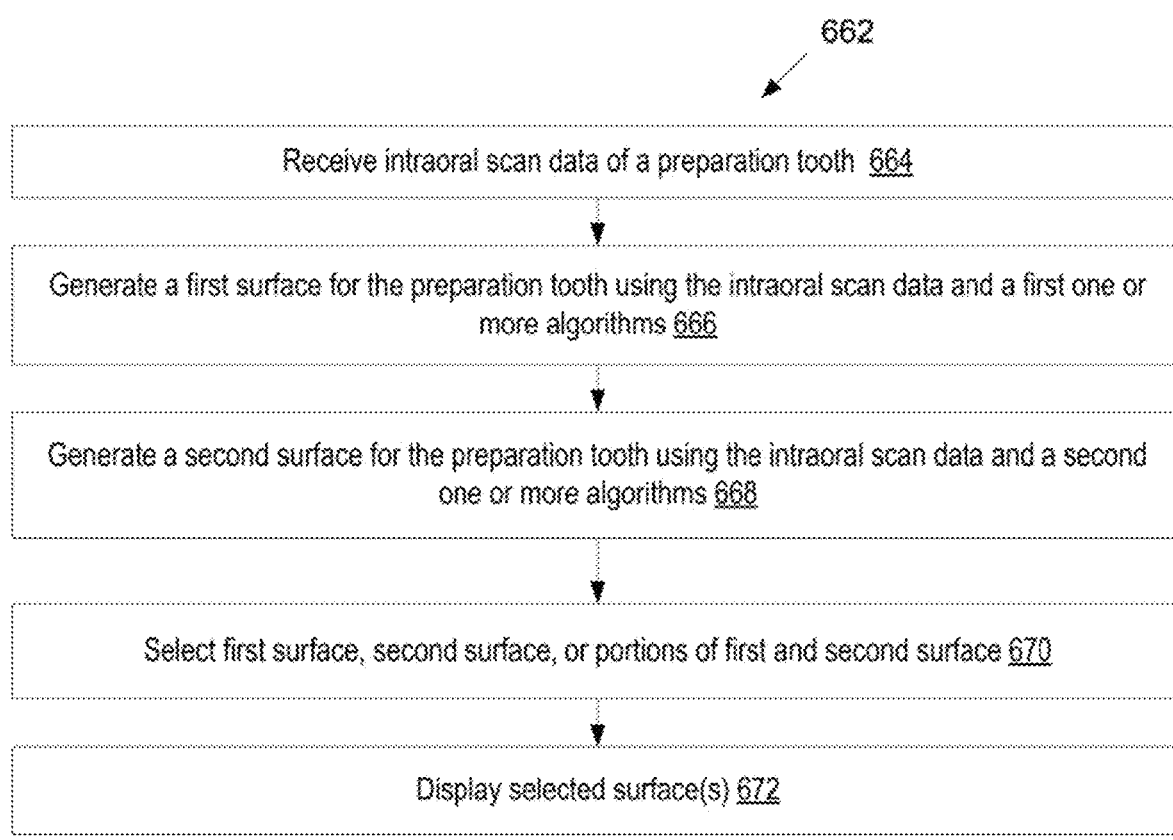
FIG. 6B illustrates a flow diagram for a method of generating a surface of a preparation tooth, in accordance with an embodiment.

FIG. 6B illustrates a flow diagram for a method 662 of generating a surface of a preparation tooth, in accordance with an embodiment. At block 664 of method 662, processing logic receives intraoral scan data of a preparation tooth. At block 666, processing logic generates a first surface of the preparation tooth using the intraoral scan data and a first one or more algorithms (e.g., of a standard intraoral scanning mode). In one embodiment, generating the second surface for the preparation tooth using the intraoral scan data and the second one or more algorithms includes determining a conflicting surface from the intraoral scan data, wherein a first intraoral scan of the intraoral scan data has a first distance from a probe of an intraoral scanner for the conflicting surface and a second intraoral scan of the intraoral scan data has a second distance from the probe of the intraoral scanner for the conflicting surface. Generating the second surface further includes averaging a representation of the conflicting surface from the first intraoral scan and a representation of the conflicting surface from the second intraoral scan.

At block 668, processing logic generates a second surface for the preparation tooth using the intraoral scan data and a second one or more algorithms (e.g., of a partial retraction scanning mode). In one embodiment, generating the first surface for the preparation tooth using the intraoral scan data and the first one or more algorithms includes determining a conflicting surface from the intraoral scan data, wherein a first intraoral scan of the intraoral scan data has a first distance from a probe of an intraoral scanner for the conflicting surface and a second intraoral scan of the intraoral scan data has a second distance from the probe for the conflicting surface. Processing logic then determines whether the first distance is greater than the second distance and/or determines whether a difference between the first distance and the second distance is greater than a difference threshold. Responsive to determining that the difference is greater than the difference threshold and that the first distance is greater than the second distance, processing logic discards a representation of the conflicting surface from the second intraoral scan, wherein the representation of the conflicting surface from the first intraoral scan is used for the conflicting surface in the first surface At block 670, processing logic (or a user) selects the first surface or the second surface. Alternatively, in some embodiments the processing logic and/or user may select some portions of the first surface and some portions of the second surface. At block 672, processing logic displays the selected surfaces (or selected portions of surfaces).

In some embodiments, a superimposition of the first and second surfaces is shown. A user may view the superimposition of the two surfaces in order to make an informed decision as to which surface to select.

Additional scan data of a dental arch comprising the preparation tooth may also be received. A third surface of the dental arch may be generated, where the third surface does not include the preparation tooth. A virtual 3D model of the dental arch may then be generated using the third surface and the selected first surface or second surface (or selected portions of the first and second surface).

FIG. 7A illustrates a flow diagram for a method 700 of generating a virtual 3D model of a preparation tooth using intraoral scan data of an intraoral scanner together with at least one of CBCT scan data, OCT scan data or ultrasound scan data, in accordance with an embodiment. At block 710 of method 700, processing logic receives a plurality of intraoral scans of a preparation tooth comprising a margin line that underlies a gingiva. At least a portion of the margin line is not shown in the plurality of intraoral scans. At block 715, processing logic receives at least one of a cone-beam computed tomography (CBCT) scan, an optical coherence tomography (OCT) scan, or an ultrasound scan of the preparation tooth, wherein the margin line is shown in at least one of the CBCT scan, the OCT scan or the ultrasound scan. At block 720, processing logic processes the CBCT scan, the OCT scan and/or the ultrasound scan to identify a) the preparation tooth, b) the gingiva and c) the margin line. Such processing may be performed using image processing techniques such as segmentation. Portions of the identified margin line that are based on CBCT, OCT or ultrasound data may be labeled with a confidence score, which may be expressed in terms of microns. In some instances, if a margin line or portion of a margin line has a low confidence score, then a doctor may manually correct the margin line, may rescan some areas of the margin line, or may rescan the entire margin line.

In some embodiments, a machine learning model is trained to perform pixel-level classification of input CBCT scans, OCT scans and/or ultrasound scans using the techniques described herein with reference to height maps and intraoral scans. The pixel-level classification be performed to classify each pixel in the input CBCT scan, OCT scan or ultrasound scan as one of a preparation tooth, gingiva or a margin line.

There are multiple different types of margin lines that may be generated when a doctor grinds down a tooth to generate a preparation tooth, having different axial reduction, different margin placement, different margin adaptation, different margin geometry and/or different margin designs. For example, margin placement may include supra-gingival margins and sub-gingival margins. The margin of the preparation tooth may have a knife or feather edge margin, a chisel edge margin, a shoulder margin, a beveled shoulder margin, a beveled margin, a sloped shoulder margin, or a chamfer margin, each having an associated margin line. Once the margin line for a particular type of margin is identified at some parts of the preparation tooth from the intraoral scan data (including how the margin is related to or connects to a remainder of the preparation tooth, this information can be used along with the data from the additional imaging modality to extrapolate where the margin line is for the rest of the preparation tooth. Additionally, a tooth outline can be automatically computed for preparation tooth from the additional scan data (e.g., from the CBCT scan). This can be used to roughly estimate the shape of the tooth under the gingiva.

CBCT scan data generally has a much lower resolution than intraoral scan data. This reduced resolution can make it difficult to extract useful information about the margin line. However, where there is some information about the margin line from the intraoral scan data, this information can be used to improve an estimate of a shape and location of the margin line as depicted in the CBCT scan. The combination of the high resolution data for some portions of the margin line from the intraoral scans and the low resolution data for all or a remainder of the margin line from the CBCT scan can provide a much higher accuracy of an estimation of a shape of the margin line than either piece of information on its own.

In some embodiments, the intraoral scan data and CBCT scan data are combined to generate a multivariate embedding that can be input into a machine learning model that has been trained to perform segmentation and identify a margin line using such combined intraoral scan and CBCT scan data.

At block 725, processing logic generates a virtual three-dimensional model of the preparation tooth using the plurality of intraoral scans and at least one of the CBCT scan, the OCT scan, or the ultrasound scan. At least one of the CBCT scan, the OBT scan or the ultrasound scan is used to depict the margin line (or portions thereof) in the virtual three-dimensional model.

FIG. 7B illustrates another flow diagram for a method 730 of generating a virtual 3D model of a preparation tooth using intraoral scan data of an intraoral scanner together with at least one of CBCT scan data, OCT scan data or ultrasound scan data, in accordance with an embodiment. In one embodiment, method 730 is performed at block 725 of method 700.

At block 732 of method 730, processing logic merges together data from the plurality of intraoral scans to form a preliminary virtual three-dimensional model of the preparation tooth, wherein the margin line is covered by the gingiva in the preliminary virtual three-dimensional model. At block 734, processing logic then merges data from the CBCT scan, the OCT scan or the ultrasound scan with the preliminary virtual three-dimensional model to generate a three-dimensional virtual model. This may include registering the CBCT scan, OCT scan or ultrasound scan with the virtual 3D model. Merging algorithms may then select whether to use data from just the intraoral scans, data from just the CBCT scan, OCT scan or ultrasound scan, or an averaging of data from both the intraoral scans and the other imaging modality to depict one or more regions of the virtual 3D model.

In one embodiment, at block 736 processing logic determines locations of the margin line from the CBCT scan, the OCT scan, or the ultrasound scan. At block 738, processing logic then removes a gingival surface that overlies the margin line from the preliminary virtual three-dimensional model. At block 740, processing logic additionally replaces the removed gingival surface with a surface of the preparation tooth as depicted in the CBCT scan or the OCT scan or the ultrasound scan.

Figure 7C:
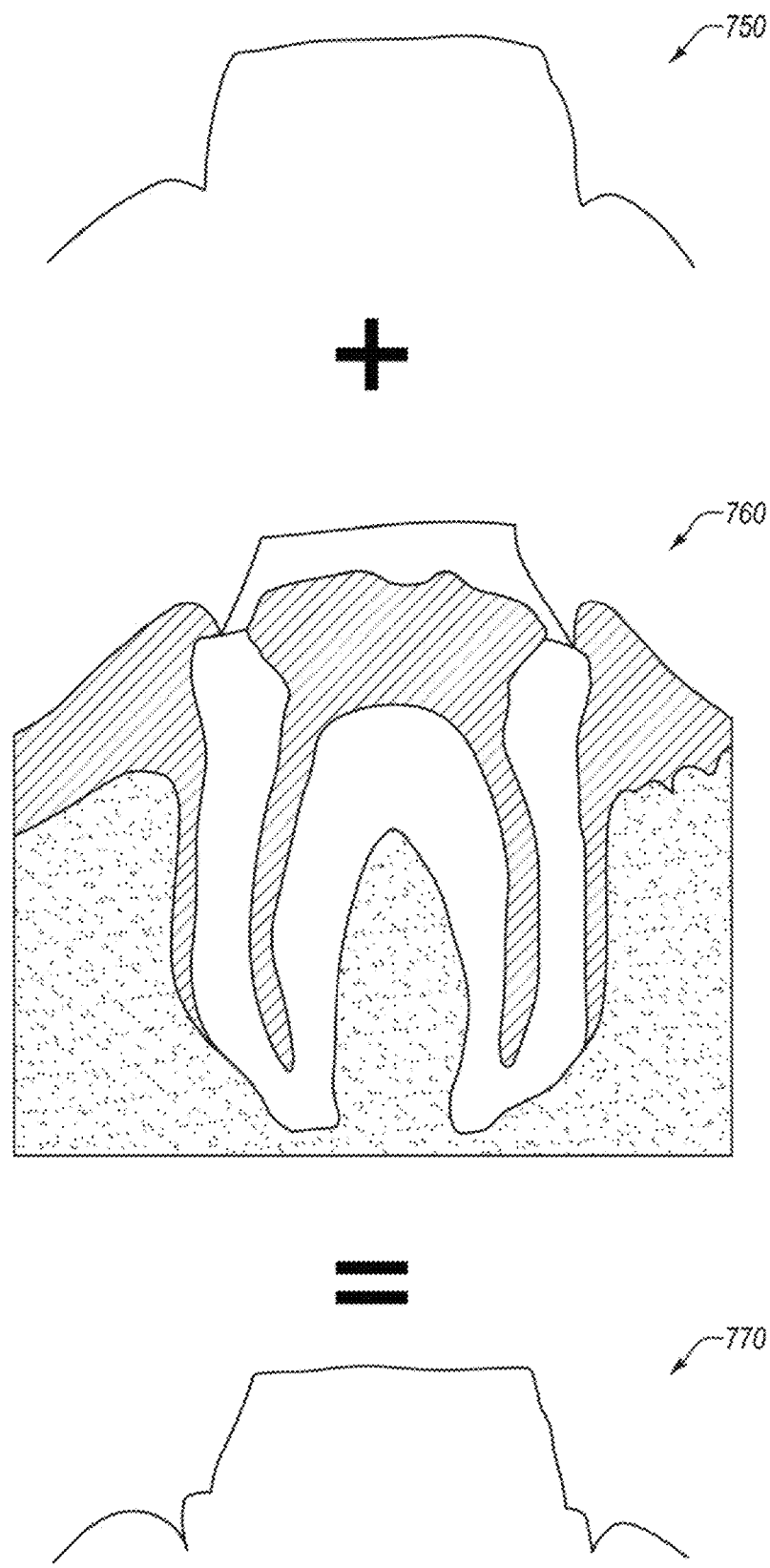
FIG. 7C illustrates merging of intraoral scan data of an intraoral scanner with at least one of CBCT scan data, OCT scan data or ultrasound scan data, in accordance with an embodiment.

FIG. 7C illustrates merging of intraoral scan data 750 of an intraoral scanner with additional scan data 760 generated using a different imaging modality (e.g., CBCT scan data, OCT scan data or ultrasound scan data) to form a merged 3D surface 770, in accordance with an embodiment. As shown, the margin line is covered by gingiva in the intraoral scan data 750. The margin line is also covered by the gingiva in the additional scan data 760, but the imaging modality used to generate the additional scan data 760 depicts objects under the gingiva as well as the surface of the gingiva. Accordingly, the additional scan data 760 may be used to determine the shape and location of the margin line, and this information may be used to remove the overlying gingiva, resulting in the merged 3D surface 770.

Figure 8:
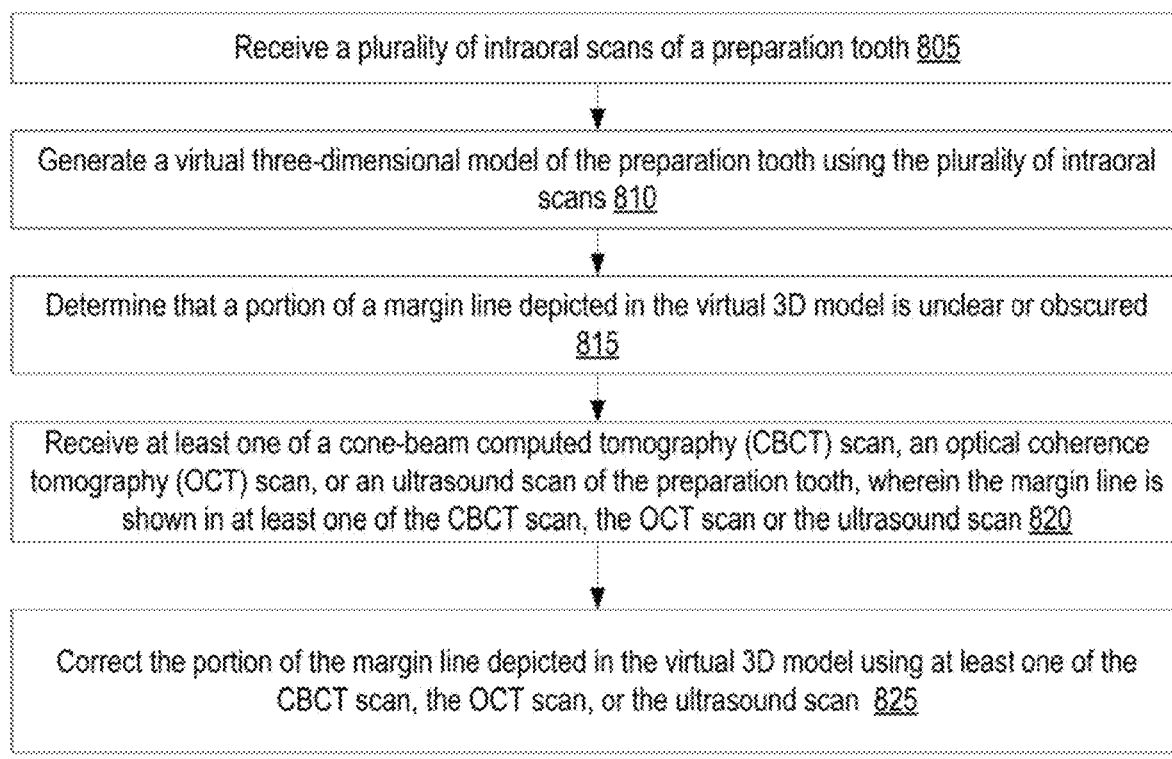
FIG. 8 illustrates a flow diagram for a method of resolving an obscured margin line for a preparation tooth using at least one of CBCT scan data, OCT scan data or ultrasound scan data, in accordance with an embodiment.

FIG. 8 illustrates a flow diagram for a method 800 of resolving an obscured margin line for a preparation tooth using at least one of CBCT scan data, OCT scan data or ultrasound scan data, in accordance with an embodiment. At block 805 of method 800, processing logic receives a plurality of intraoral scans of a preparation tooth. At block 810, processing logic generates a virtual 3D model of the preparation tooth using the intraoral scans. At block 815, processing logic determines that a portion of the margin line depicted in the virtual 3D model is unclear or obscured. At block 820, processing logic receives at least one of a cone-beam computed tomography (CBCT) scan, an optical coherence tomography (OCT) scan, or an ultrasound scan of the preparation tooth, wherein the margin line is shown in at least one of the CBCT scan, the OCT scan or the ultrasound scan. At block 800, processing logic then corrects the portion of the margin line depicted in the virtual 3D model using data from at least one of the cone-beam computed tomography (CBCT) scan, the optical coherence tomography (OCT) scan, or the ultrasound scan. In some instances, multiple types of additional scans are received, and a combination of CBCT scan data and OCT scan data, a combination of CBCT scan data and ultrasound scan data, a combination of OCT scan data and ultrasound scan data, or a combination of CBCT scan data, OCT scan data and ultrasound scan data is used to enhance the virtual 3D model of the preparation tooth.

Figure 9:
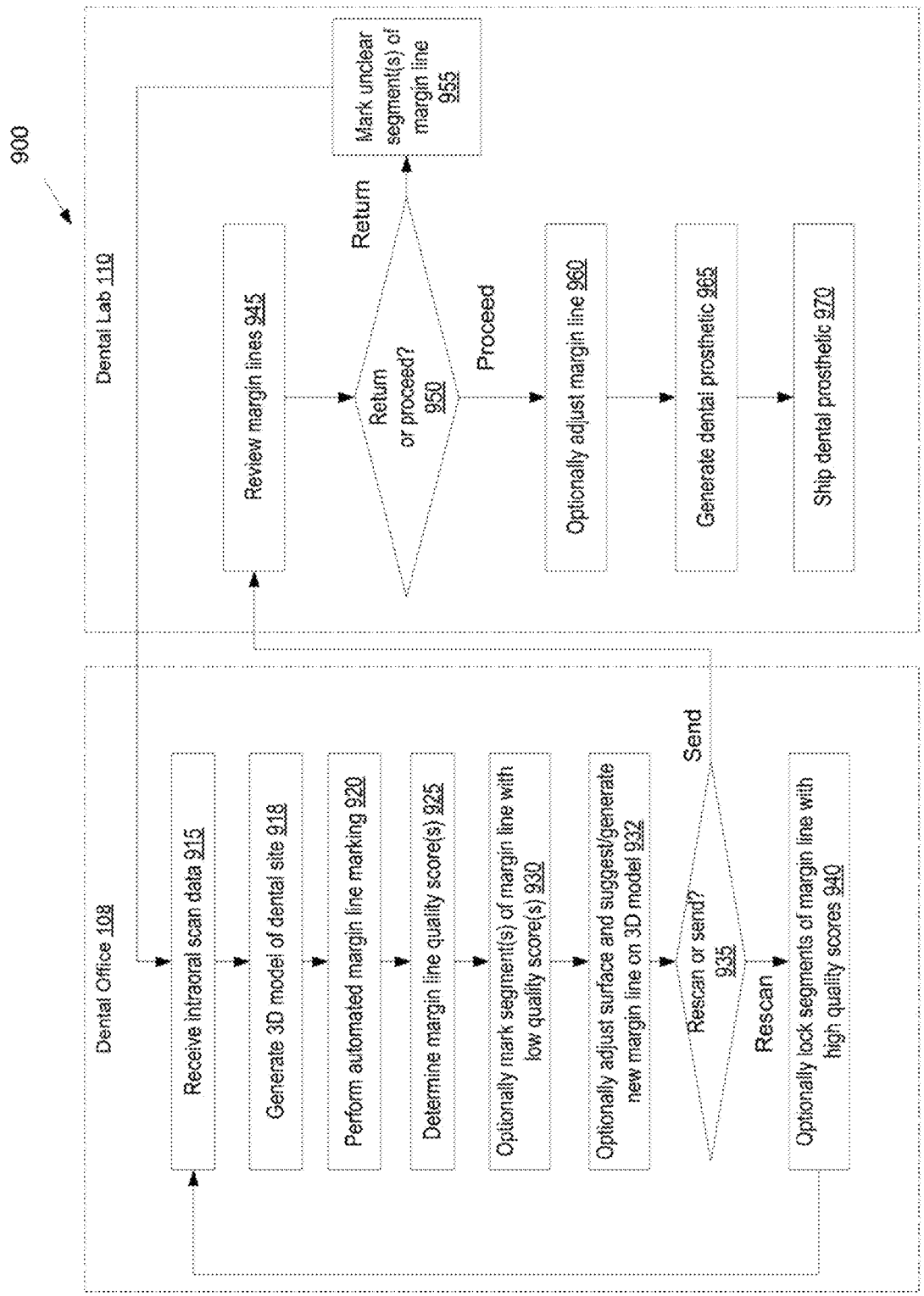
FIG. 9 illustrates an example workflow for generating an accurate virtual 3D model of a dental site and manufacturing a dental prosthetic from the virtual 3D model, in accordance with embodiments of the present disclosure.

FIG. 9 illustrates an example workflow of a method 900 for generating an accurate virtual 3D model of a dental site and manufacturing a dental prosthetic from the virtual 3D model, in accordance with embodiments of the present disclosure. Operations of the workflow may be performed at a dental office 105 or at a dental lab 110. Those operations performed at the dental office 105 may be performed during a single patient visit or over the course of multiple patient visits. The operations listed under dental office 105 may be performed, for example, by intraoral scan application 115. The operations listed under dental lab 110 may be performed, for example, by dental modeling application 120. Intraoral scan application 115 and/or dental modeling application 120 may incorporate dental modeling logic 2550 of FIG. 25 in embodiments.

Method 900 may begin at block 915, at which processing logic executing on a computing device associated with dental office 105 receives intraoral scan data (or other scan data such as CBCT scan data, OCT scan data and/or ultrasound scan data). The intraoral scan data may have been generated by intraoral scanner 150 during an intraoral scan process. The intraoral scan data may have been generated in accordance with a standard preparation scanning procedure or in accordance with a partial retraction scanning procedure, as described above. At block 918, processing logic generates a virtual 3D model of one or more dental site based on the intraoral scan data, as discussed herein above. The virtual 3D model may be of an entire dental arch or of a portion of a dental arch (e.g., a portion including a preparation tooth and adjoining teeth).

At block 920, processing logic performs automated margin line marking on the 3D model. In one embodiment, automated margin line marking is performed by first generating appropriate data inputs from the 3D model (e.g., one or more images or height maps of the 3D model). These inputs include any information produced during scanning that is useful for margin line detection. Inputs may include image data, such as 2D height maps that provide depth values at each pixel location, and/or color images that are actual or estimated colors for a given 2D model projection. 3D inputs may also be used and include Cartesian location and connectivity between vertices (i.e. mesh). Each image may be a 2D or 3D image generated by projecting a portion of the 3D model that represents a particular tooth onto a 2D surface. Different images may be generated by projecting the 3D model onto different 2D surfaces. In one embodiment, one or more generated images may include a height map that provides a depth value for each pixel of the image. Alternatively, or additionally, intraoral images that were used to generate the 3D model may be used. The generated images and/or the received intraoral images may be processed by a machine learning model that has been trained to identify margin lines on preparation teeth. The machine learning model may output a probability map that indicates, for each pixel of the image or 3D data input into the machine learning model, a probability that the pixel or surface represents a margin line. In the case of images, the probability map may then be projected back onto the 3D model to assign probability values to points on the 3D model. A cost function may then be applied to find the margin line using the probability values assigned to the points on the 3D model. Other techniques may also be used to compute the margin line based on the assigned probability values. In one embodiment, one or more of operations 1515-1525 of method 1500 depicted in FIG. 15 and/or operations 1630-1640 of method 1600 depicted in FIG. 16 are performed at block 920.

At block 925, processing logic computes one or more margin line quality scores. Each margin line quality score may be based on the cost value for the margin line (or a segment of the margin line) as computed using the cost function. In one embodiment, a margin line quality score is determined for the entirety of the margin line. In one embodiment, multiple additional margin line quality scores are computed, where each margin line quality score is for a particular segment of the margin line.

At block 930, processing logic may mark segments of the margin line on the 3D model having low quality scores. For example, the margin line quality scores for one or more margin line segments may be compared to a quality threshold. Any scores that are representative of costs that exceed a maximum cost may fail to satisfy the quality threshold. Those segments that fail to satisfy the quality threshold may be marked with a marking that distinguishes them from a remainder of the margin line. For example, low quality margin line segments may be highlighted on the 3D model. In one embodiment, one or more of operations 1645-1665 of method 1600 of FIG. 16 are performed at block 930.

In some embodiments, processing logic may additionally or alternatively determine a clarity value and/or quality value for surfaces that do not include or are not associated with a margin line. Processing logic may mark such surfaces (or portions of surfaces) that have low quality values on the 3D model. For example, the surface quality scores for one or more surface portions may be compared to a quality threshold. Any surfaces (or surface portions) having surface quality scores that are below the quality threshold may be marked or highlighted.

At block 932, processing logic may optionally adjust a surface of at least a portion of the 3D model of the dental site and/or may suggest and/or generate a segment of the margin line. In one embodiment, processing logic inputs the image into a machine learning model that has been trained to generate modified versions of input images, where the modified versions have corrected surfaces. In an example, the machine learning model may be trained to adjust the surface of a tooth in an image of the tooth and to fabricate a segment of the margin line in a region where the segment of the margin line is not shown. The modified image may be used to adjust the 3D model of the dental site. For example, processing logic may automatically select a region of a 3D model that depicts an unclear segment of the margin line. Areas in the 3D model outside of the selected region may be locked so that those regions will not be modified. The modified image may then be registered with the 3D model, and a first version of the selected region of the 3D model may be replaced with data from the modified image to generate a second version of the selected region without affecting the locked areas of the 3D model. Alternatively, the modified 3D image may be projected onto the 3D model without first locking any portion of the 3D model, and a portion of the original surface of the 3D model may be replaced with a new surface using data from the modified image.

In some embodiments, a lock that is applied to lock one or more regions (e.g., regions other than a selected region) is a one-way lock. For the one-way lock, the locked areas are not affected by the data from the modified image if adjusting the regions using the data from the modified image would result in a degraded representation of those regions. However, if use of the data from the modified image would improve the representation of those regions, then the data from the modified image may be used to update those regions. In one embodiment, the data from the modified image includes one or more scores associated with the region or regions. The scores may indicate a confidence and/or quality of the modified image at those regions. If the score is above a threshold, then processing logic may determine that the data from the modified image would improve a quality of the representation of those regions. In one embodiment each of the regions is scored, and the current score of a region is used as the threshold.

In some embodiments, the operations of block 930 are performed, and the operations of block 932 are skipped. In other embodiments, the operations of block 932 are performed and the operations of block 930 are skipped. In still other embodiments, the operations of both block 930 and block 932 are performed.

At block 935, a doctor may provide feedback indicating that the 3D model is acceptable or that the 3D model should be updated. If the doctor indicates that the 3D model is acceptable, then the 3D model is sent to the dental lab 110 for review, and the method continues to block 945. If the doctor indicates that the 3D model is not acceptable, then the method continues to block 940.

At block 940, the doctor may use a user interface to indicate one or more regions of the 3D model that are to be rescanned. For example, the user interface may include an eraser function that enables the doctor to draw or circle a portion of the 3D model. An area inside of the drawn region or circle may be erased, and a remainder of the 3D model may be locked. Locked regions of the 3D model may not be modified by new intraoral scan data. Alternatively, a one-way lock may be applied, and the locked regions may be modified under certain conditions. Alternatively, processing logic may automatically select regions depicting margin line segments with low quality scores for erasure, and may automatically lock a remainder of the 3D model. Processing logic may then graphically indicate to the doctor where to position the intraoral scanner 150 to generate replacement image data. The method may then return to block 915, and new intraoral image data depicting the region that was erased may be received. The new intraoral image data may be generated using a standard scanning procedure or a partial retraction scanning procedure.

At block 918, the 3D model may be updated based on the new image data. In one embodiment, the unlocked portion of the 3D model is updated based on the new image data, but the locked regions are not updated.

In one embodiment, one or more regions are locked using a one-way lock. For the one-way lock, the locked areas are not affected by the new image data if adjusting the regions using the new image data would result in a degraded representation of those regions. However, if use of the new image data would improve the representation of those regions, then the new image data may be used to update those regions. In one embodiment, processing logic processes the new image data (e.g., using a trained machine learning model) to determine a quality score for the new image data. In some embodiments, multiple quality scores are determined for the new image data, where each quality score may be associated with a different region of a dental site. Additionally, quality scores may be determined for one or more regions of the 3D model. If a score for a region from the new image data is higher than the score for that same region from the 3D model, then the image data may be used to update that region of the 3D model. If the score for a region of the new image data is less than or equal to the score for that same region from the 3D model, then the new image data may not be used to update that region of the 3D model.

The operations of blocks 920-935 may then be repeated based on the updated 3D model.

At block 945, a lab technician may review the margin lines in the 3D model (e.g., using a dental modeling application 120). Alternatively, or additionally, processing logic (e.g., processing logic of a dental modeling application 120) may process the 3D model to automatically determine and/or grade the margin line. In one embodiment, reviewing the margin lines at block 945 includes performing operations 920-930. At block 950, processing logic determines whether to proceed with using the 3D model to manufacture a dental prosthetic or to return the 3D model to the dental office 105. If the margin line meets a minimum quality threshold, then the method proceeds to block 960. If the margin line does not meet the minimum quality threshold, then the method continues to block 955, and the 3D model is returned to the dental office 105 to enable the doctor to generate further intraoral scans of the dental site. At block 955, a lab technician may manually mark unclear segments of the margin line. Alternatively, unclear segments may be automatically marked by processing logic at block 955, or may have already been marked at block 945. A message is then sent to the doctor asking for additional intraoral images to be generated. The message may provide a copy of the 3D model showing regions that should be reimaged.

Figure 20:
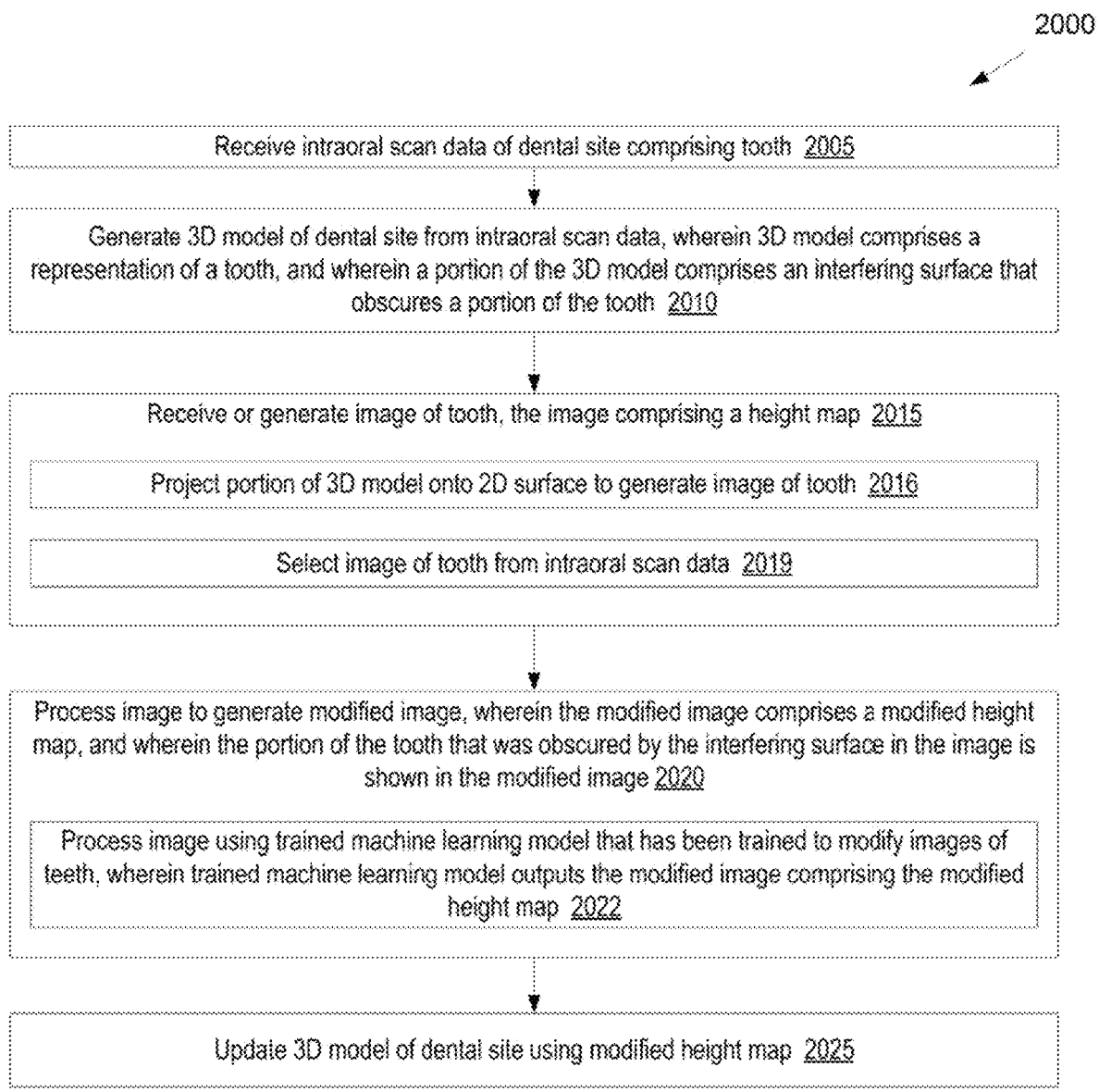
FIG. 20 illustrates a flow diagram for a method of correcting a representation of a tooth in a 3D model of a dental site, in accordance with an embodiment.

At block 960, the margin line may automatically be adjusted. In some instances, at block 950 processing logic may determine that the margin line has insufficient quality, but for some reason the doctor may be unable to collect new images of the dental site. In such instances, processing logic may proceed to block 960 even if the margin line has an unacceptable level of quality. In such instances, the margin line may be automatically adjusted at block 960. Alternatively, the margin line may be manually adjusted using, for example, CAD tools. In one embodiment, the margin line is adjusted by generating images of the 3D model (e.g., by projecting the 3D model onto 2D surfaces) and processing the images using a trained machine learning model that has been trained to correct margin lines in images of preparation teeth. In one embodiment, one or more operations of method 2000 of FIG. 20 are performed at block 960.

At block 965, processing logic generates a dental prosthetic using the virtual 3D model of the dental site. In one embodiment, the virtual 3D model is input into a rapid prototyping machine (e.g., a 3D printer), and a physical model of the dental site(s) (e.g., of a preparation tooth and adjacent teeth) is produced. The physical 3D model may then be used to generate the dental prosthetic. Alternatively, a virtual 3D model of the dental prosthetic may be generated from the virtual 3D model of the dental site(s), and the virtual 3D model of the dental prosthetic may be used to directly manufacture the dental prosthetic using 3D printing. At block 970, the dental prosthetic may then be shipped to the dental office 105.

Figure 10:
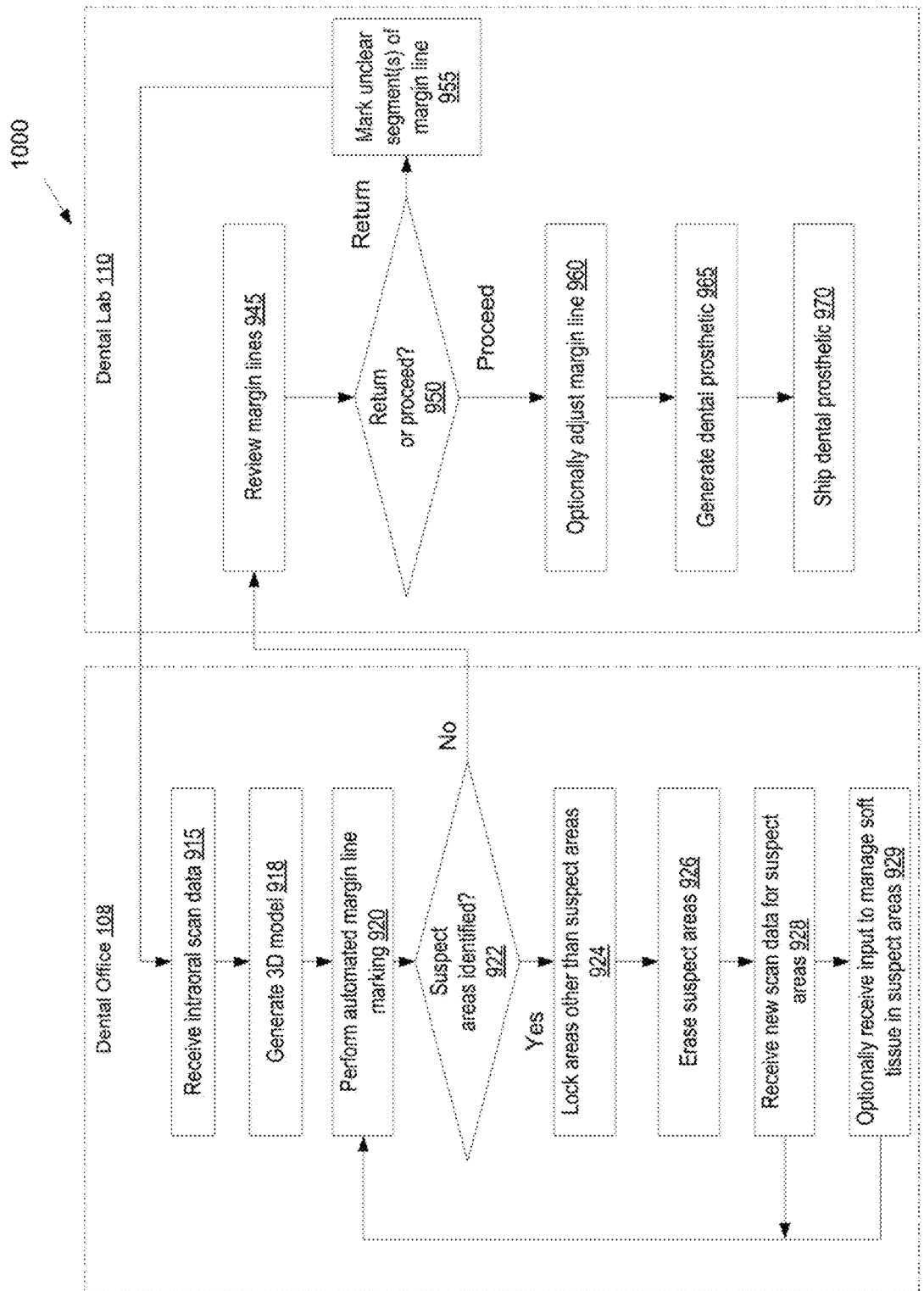
FIG. 10 illustrates another example workflow for generating an accurate virtual 3D model of a dental site and manufacturing a dental prosthetic from the virtual 3D model, in accordance with embodiments of the present disclosure.

FIG. 10 illustrates another example workflow of a method 1000 for generating an accurate virtual 3D model of a dental site and manufacturing a dental prosthetic from the virtual 3D model, in accordance with embodiments of the present disclosure. Operations of the workflow may be performed at a dental office 105 or at a dental lab 110. Those operations performed at the dental office 105 may be performed during a single patient visit or over the course of multiple patient visits. The operations listed under dental office 105 may be performed, for example, by intraoral scan application 115. The operations listed under dental lab 110 may be performed, for example, by dental modeling application 120. Intraoral scan application 115 and/or dental modeling application 120 may incorporate dental modeling logic 2550 of FIG. 25 in embodiments.

Method 1000 may begin at block 915, at which processing logic executing on a computing device associated with dental office 105 receives intraoral scan data. The intraoral scan data may have been generated in accordance with a standard (e.g., full retraction) scanning procedure or in accordance with a partial retraction scanning procedure, as described above. At block 918 a 3D model of at least a portion of a dental arch (e.g., of one or more dental sites) is generated using the intraoral scan data. At block 920, processing logic performs automated margin line marking on the 3D model, as discussed elsewhere herein. At block 922, processing logic determines whether any suspect areas of the 3D model are identified. A suspect area may be identified, for example, by identifying margin line segments with cost values that exceed a cost threshold or by identifying margin line segments with quality values that fall below a quality threshold, where the quality values may be based on the cost values. For example, processing logic may compute one or more margin line quality scores. Each margin line quality score may be based on the cost value for the margin line (or a segment of the margin line) as computed using a cost function, and the margin line quality scores may be compared to a quality threshold to determine if suspect areas are identified. If suspect areas are identified, the method proceeds to block 924. If no suspect areas are identified, the method proceeds to block 945.

At block 924, processing logic automatically locks areas of the 3D model other than the suspect areas. This may ensure that the locked areas, which represent accurate depictions of regions of a dental site, will not be modified. In some embodiments, a one-way lock is used to lock the areas of the 3D model other than the suspect areas, as described above. At block 926, the suspect areas may then be erased using an eraser tool.

A doctor may then be instructed to generate one or more new intraoral images depicting the suspect area that has been erased in the 3D model. Following such instruction, the doctor may perform an additional intraoral scan, and processing logic may receive new scan data including one or more new intraoral images depicting the suspect area at block 928. The additional intraoral scan may be performed using a standard scanning procedure or a partial retraction scanning procedure. The method may then return to block 920 and update the 3D model using the received new scan data.

Alternatively, or additionally, in some instances, scan data used to generate the 3D model includes blended intraoral images, where each blended intraoral image is based on a combination of multiple distinct intraoral images that may have been generated sequentially. In such instances, processing logic may access one or more image files of blended images, and may determine which blended images were used to generate the portion of the 3D model that represented the suspect area. Processing logic may then review the distinct images that were used to generate the one or more determined blended images. Processing logic may analyze these distinct images to identify one or more of the distinct images that provide a superior representation of the suspect area, and may select one or more of the identified distinct images. The method may then return to block 920 and update the 3D model using the selected one or more distinct intraoral images.

Additionally, or alternatively to the operations of block 928 or the alternative operations described above, at block 929 processing logic may receive input from a doctor manually manipulating the 3D surface of the 3D model at the suspect area. For example, the doctor may manually draw a surface, draw a margin line, etc. The doctor may also manage soft tissue, such as by manually removing a representation of a portion of soft tissue from the 3D model. This may cause one or more new images of the dental site to be generated from the 3D model, which may be input into a machine learning model trained to identify margin lines. An output of the machine learning model may then be used to update the 3D model at block 920.

At block 945, a lab technician may review the margin lines in the 3D model (e.g., using a dental modeling application 120. Alternatively, or additionally, processing logic (e.g., processing logic of a dental modeling application 120) may process the 3D model to automatically determine and/or grade the margin line. At block 950, processing logic determines whether to proceed with using the 3D model to manufacture a dental prosthetic or to return the 3D model to the dental office 105. If the margin line meets a minimum quality threshold, then the method proceeds to block 960. If the margin line does not meet the minimum quality threshold, then the method continues to block 955, and the 3D model is returned to the dental office 105 to enable the doctor to generate further intraoral scans of the dental site. At block 955, a lab technician may manually mark unclear segments of the margin line. Alternatively, unclear segments may be automatically marked by processing logic at block 955, or may have already been marked at block 945. A message is then sent to the doctor asking for additional intraoral images to be generated. The message may provide a copy of the 3D model showing regions that should be reimaged.

At block 960, the margin line may automatically be adjusted. In some instances, at block 950 processing logic may determine that the margin line has insufficient quality, but for some reason the doctor may be unable to collect new images of the dental site. In such instances, processing logic may proceed to block 960 even if the margin line has an unacceptable level of quality. In such instances, the margin line may be automatically adjusted at block 960. Alternatively, the margin line may be manually adjusted using, for example, CAD tools. In one embodiment, the margin line is adjusted by generating images of the 3D model (e.g., by projecting the 3D model onto 2D surfaces) and processing the images using a trained machine learning model that has been trained to correct margin lines in images of preparation teeth. In one embodiment, one or more operations of method 2000 of FIG. 20 are performed at block 960.

At block 965, processing logic generates a dental prosthetic using the virtual 3D model of the dental site. In one embodiment, the virtual 3D model is input into a rapid prototyping machine (e.g., a 3D printer), and a physical model of the dental site(s) (e.g., of a preparation tooth and adjacent teeth). The physical 3D model may then be used to generate the dental prosthetic. Alternatively, a virtual 3D model of the dental prosthetic may be generated from the virtual 3D model of the dental site(s), and the virtual 3D model of the dental prosthetic may be used to directly manufacture the dental prosthetic using 3D printing. At block 970, the dental prosthetic may then be shipped to the dental office 105.

Figure 11:
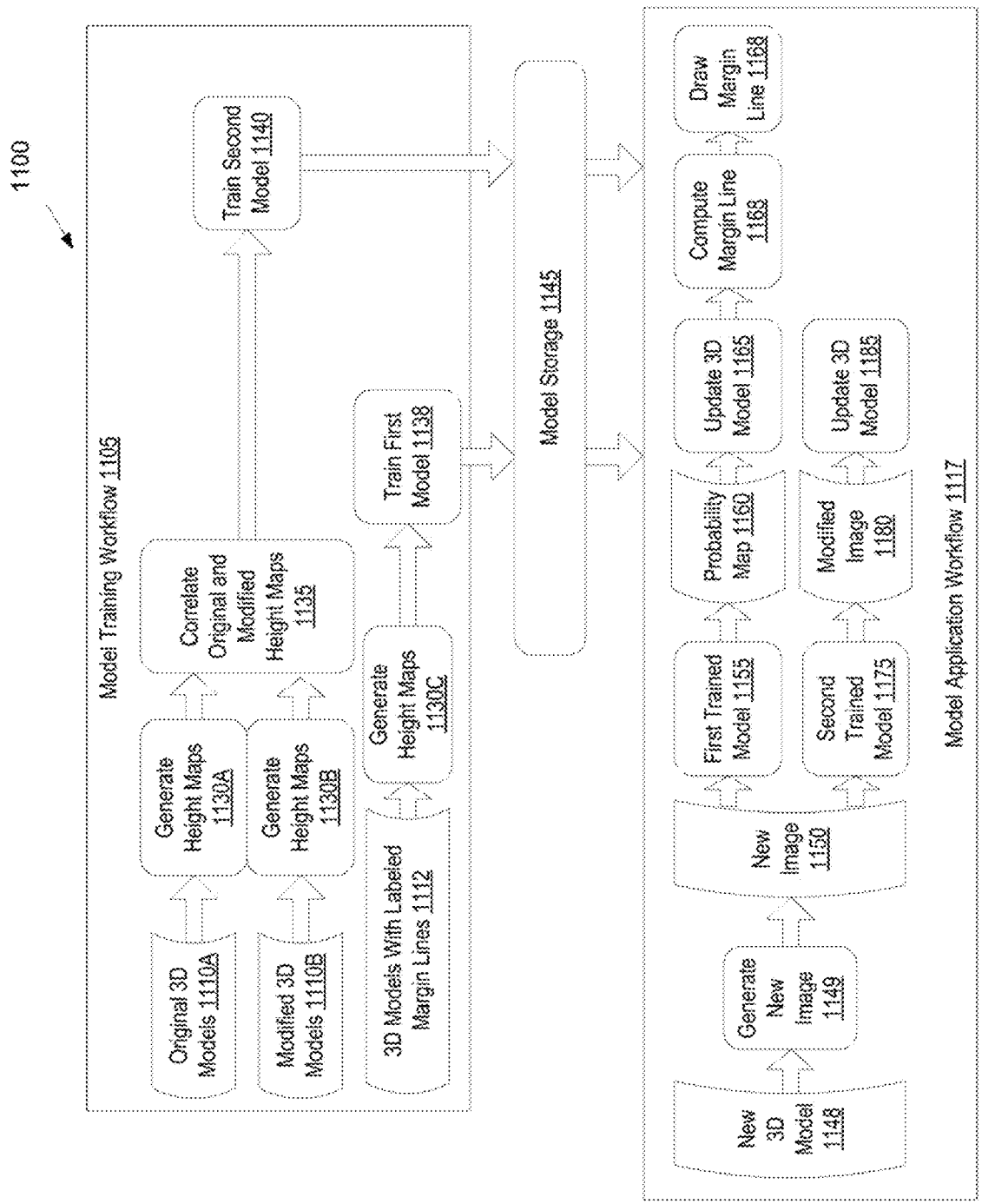
FIG. 11 illustrates workflows for training machine learning models and applying the trained machine learning models to images, in accordance with embodiments of the present disclosure.

FIG. 11 illustrates workflows for training machine learning models and applying the trained machine learning models to images, in accordance with embodiments of the present disclosure. The illustrated workflows include a model training workflow 1105 and a model application workflow 1117. The model training workflow 1105 is to train one or more machine learning models (e.g., deep learning models) to perform one or more image processing and/or labeling tasks for an image containing teeth. The model application workflow 1117 is to apply the one or more trained machine learning models to label one or more properties and/or areas in images of teeth and/or to modify images of teeth.

One type of machine learning model that may be used is an artificial neural network, such as a deep neural network. Artificial neural networks generally include a feature representation component with a classifier or regression layers that map features to a desired output space. A convolutional neural network (CNN), for example, hosts multiple layers of convolutional filters. Pooling is performed, and non-linearities may be addressed, at lower layers, on top of which a multi-layer perceptron is commonly appended, mapping top layer features extracted by the convolutional layers to decisions (e.g. classification outputs). Deep learning is a class of machine learning algorithms that use a cascade of multiple layers of nonlinear processing units for feature extraction and transformation. Each successive layer uses the output from the previous layer as input. Deep neural networks may learn in a supervised (e.g., classification) and/or unsupervised (e.g., pattern analysis) manner. Deep neural networks include a hierarchy of layers, where the different layers learn different levels of representations that correspond to different levels of abstraction. In deep learning, each level learns to transform its input data into a slightly more abstract and composite representation. In an image recognition application, for example, the raw input may be a matrix of pixels; the first representational layer may abstract the pixels and encode edges; the second layer may compose and encode arrangements of edges; the third layer may encode higher level shapes (e.g., teeth, lips, gums, etc.); and the fourth layer may recognize that the image contains a face or define a bounding box around teeth in the image. Notably, a deep learning process can learn which features to optimally place in which level on its own. The "deep" in "deep learning" refers to the number of layers through which the data is transformed. More precisely, deep learning systems have a substantial credit assignment path (CAP) depth. The CAP is the chain of transformations from input to output. CAPs describe potentially causal connections between input and output. For a feedforward neural network, the depth of the CAPs may be that of the network and may be the number of hidden layers plus one. For recurrent neural networks, in which a signal may propagate through a layer more than once, the CAP depth is potentially unlimited.

In one embodiment, a class of machine learning model called a MobileNet is used. A MobileNet is an efficient machine learning model based on a streamlined architecture that uses depth-wise separable convolutions to build light weight deep neural networks. MobileNets may be convolutional neural networks (CNNs) that may perform convolutions in both the spatial and channel domains. A MobileNet may include a stack of separable convolution modules that are composed of depthwise convolution and pointwise convolution (cony 1×1). The separable convolution independently performs convolution in the spatial and channel domains. This factorization of convolution may significantly reduce computational cost from $HWNK^2M$ to $HWNK^2$ (depthwise) plus HWNM (cony 1×1), $HWN(K^2+M)$ in total, where N denotes the number of input channels, $K^2$ denotes the size of convolutional kernel, M denotes the number of output channels, and H×W denotes the spatial size of the output feature map. This may reduce a bottleneck of computational cost to cony 1×1.

Training of a neural network may be achieved in a supervised learning manner, which involves feeding a training dataset consisting of labeled inputs through the network, observing its outputs, defining an error (by measuring the difference between the outputs and the label values), and using techniques such as deep gradient descent and backpropagation to tune the weights of the network across all its layers and nodes such that the error is minimized. In many applications, repeating this process across the many labeled inputs in the training dataset yields a network that can produce correct output when presented with inputs that are different than the ones present in the training dataset. In high-dimensional settings, such as large images, this generalization is achieved when a sufficiently large and diverse training dataset is made available.

The model training workflow 1105 and the model application workflow 1117 may be performed by processing logic executed by a processor of a computing device. These workflows 1105, 1117 may be implemented, for example, by one or more machine learning modules implemented in an intraoral scanning application, a tooth modeling application and/or tooth modeling logic 2550 executing on a processing device 2502 of computing device 2500 shown in FIG. 25. Additionally FIGS. 12-22 below describe example operations and/or methods associated with training a machine learning model or applying a trained machine learning model to an input image.

For the model training workflow 1105, a training dataset containing hundreds, thousands, tens of thousands, hundreds of thousands or more images should be used to form a training dataset. In embodiments, up to millions of cases of patient dentition that underwent a prosthodontic procedure may be available for forming a training dataset, where each case may include information on different activities that were performed for the case and points in time at which the different activities were performed. Each case may include, for example, data showing an initial 3D model of one or more dental sites generated from an intraoral scan, data showing any modifications made to the 3D model by lab technicians and/or a margin line drawn on the 3D model by lab technicians, data showing whether the doctor accepted the modified 3D model, data showing whether the modified 3D model resulted in a successful dental prosthetic, and so on. This data may be processed to generate a training dataset for training of one or more machine learning models. The machine learning models may be trained, for example, to automate the one or more processes that are manually performed by lab technicians, such as processes of marking margin lines on 3D models of teeth and/or processes of adjusting surfaces of 3D models of teeth. Such trained machine learning models can reduce the standard turnaround time of about 24 hours for processing 3D models generated at a dental office to a few minutes to a few hours.

In one embodiment, a first machine learning model 1155 is trained to mark margin lines in 2D images of preparation teeth. A set of many (e.g., thousands to millions) 3D models of preparation teeth with labeled margin lines 1112 may be collected. For each 3D model with a labeled margin line, a set of images (e.g., height maps) may be generated at block 1130C. Each image may be generated by projecting the 3D model (or a portion of the 3D model) onto a 2D surface. Different images of a 3D model may be generated by projecting the 3D model onto different 2D surfaces in some embodiments. For example, a first image of a 3D model may be generated by projecting the 3D model onto a 2D surface that is in a top down point of view, a second image may be generated by projecting the 3D model onto a 2D surface that is in a first side point of view (e.g., a buccal point of view), a third image may be generated by projecting the 3D model onto a 2D surface that is in a second side point of view (e.g., a lingual point of view), and so on. Each image may include a height map that includes a depth value associated with each pixel of the image. For each image, a probability map or mask may be generated based on the labeled margin line in the 3D model and the 2D surface onto which the 3D model was projected. The probability map or mask may have a size that is equal to a pixel size of the generated image. Each point or pixel in the probability map or mask may include a probability value that indicates a probability that the point represents the margin line. Points that do not represent the margin line may have a value of 0 (0%) and points that do represent the margin line may have a value of 1 (100%), for example.

At block 1138, a first machine learning model is trained using the pairs of images generated from the 3D models with the labeled margin lines. The first machine learning model (e.g., first deep learning model) may be trained to determine a margin line in an image of a preparation tooth. In particular, the first machine learning model may be trained to generate a probability map, where each point in the probability map corresponds to a pixel of an input image and indicates a probability that the pixel represents a margin line of a preparation tooth.

Figure 12:
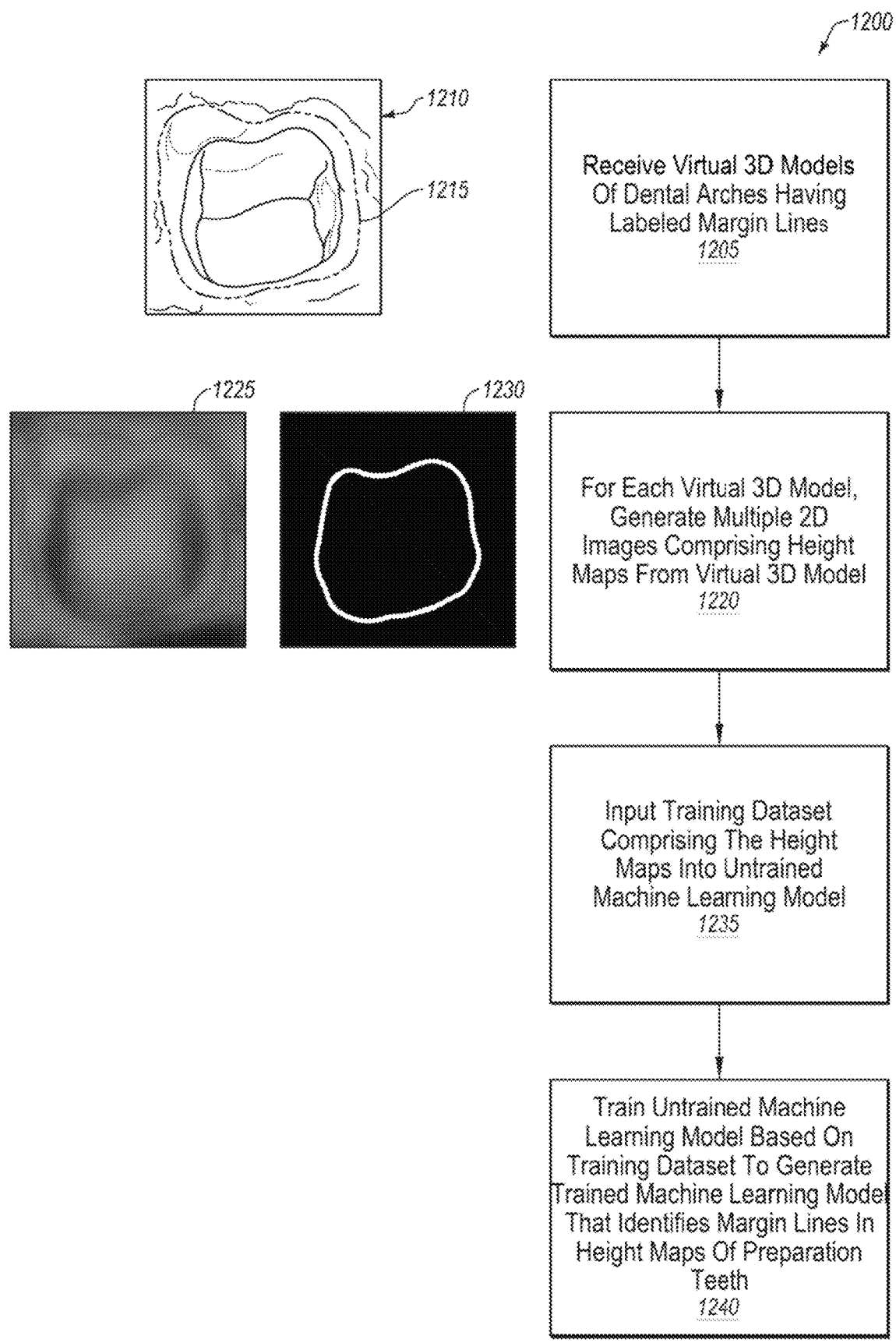
FIG. 12 illustrates a flow diagram for a method of training a machine learning model to determine margin lines in images of preparation teeth, in accordance with an embodiment.

FIG. 12 illustrates a flow diagram for a method 1200 of training a machine learning model to determine margin lines in images of preparation teeth, in accordance with an embodiment. At block 1205 of method 1200, processing logic receives virtual 3D models of dental arches having labeled margin lines. An example 3D model 1210 is shown with a labeled margin line 1215.

At block 1220, for each virtual 3D model processing logic generates one or multiple images comprising height maps from the virtual 3D model. Each image may be generated by projecting the 3D model onto a 2D surface, as described above. In one embodiment, about 10-150 greyscale height maps are generated for each case or patient. Each image may include an associated mask or probability map that indicates which pixels in the image represent the margin line. An example image 1225 and associated mask or probability map 1230 are shown. In one embodiment, each virtual 3D model includes a label of a specific tooth number and/or a specific indication.

At block 1235, processing logic inputs the training dataset comprising the height maps into the untrained machine learning model. At block 1240, processing logic trains the untrained machine learning model based on the training dataset to generate a trained machine learning model that identifies margin lines in height maps of preparation teeth. Training may be performed by inputting the images into the machine learning model one at a time. For each input image, the machine learning model generates a probability map indicating, for each pixel of the image, a probability that the pixel represents the height map. Processing logic may then compare the generated probability map to the known probability map or mask, and back propagation may be performed to update weights of nodes in the machine learning model. This process may be performed repeatedly using a large portion of the training dataset, with each iteration slightly refining the accuracy of the machine learning model. Once the machine learning model is trained, a reserved portion of the training dataset may be used to test the model.

In one embodiment, the machine learning model is additionally trained to identify teeth, gums and/or excess material. In one embodiment, the machine learning model is further trained to determine one or more specific tooth numbers and/or to identify a specific indication (or indications) for an input image. Accordingly, a single machine learning model may be trained to identify and/or correct margin lines and also to identify teeth generally, identify different specific tooth numbers, identify gums and/or identify specific indications (e.g., caries, cracks, etc.). In an alternative embodiment, a separate machine learning model is trained for each specific tooth number and for each specific indication. Accordingly, the tooth number and/or indication (e.g., a particular dental prosthetic to be used) may be indicated (e.g., may be input by a user), and an appropriate machine learning model may be selected based on the specific tooth number and/or the specific indication.

In one embodiment, the machine learning model (or a different machine learning model) is additionally or alternatively trained to determine model orientation, path of insertion for a restoration or bridge, and/or positioning of a 3D model within a CAM template. The machine learning model may be trained to process images (e.g., height maps) of teeth, and to output data (e.g., a vector, matrix, etc.) that contains additional information such as the model orientation, path of insertion and/or positioning of the 3D model within a CAM template, and so on. For example, the machine learning model may output a vector identifying a path of insertion and/or may output a matrix representing model orientation.

In an embodiment, the machine learning model may be trained to output an identification of a margin line as well as separate information indicating one or more of the above (e.g., path of insertion, model orientation, teeth identification, gum identification, excess material identification, etc.). In one embodiment, the machine learning model (or a different machine learning model) is trained to perform one or more of: identify teeth represented in height maps, identify gums represented in height maps, identify excess material (e.g., material that is not gums or teeth) in height maps, and/or identify margin line in height maps. In some instances, the margin line identified by such a machine learning model that is trained to identify teeth, gums, excess material and margin line may have increased accuracy sine the machine learning model may learn what the tooth/gum boundaries and what artifacts to ignore.

For embodiments in which the machine learning model is trained to output path of insertion, training data may include height maps that include a target path of insertion. For embodiments in which the machine learning model is trained to output a model orientation, training data may include height maps that include a labeled model orientation. For embodiments in which the machine learning model is trained to output a tooth identification, training data may include height maps that include a labeled teeth. For embodiments in which the machine learning model is trained to output a gum identification, training data may include height maps that include a labeled gums. For embodiments in which the machine learning model is trained to output an identification of excess material, training data may include height maps that include a labeled excess material. For embodiments in which the machine learning model is trained to output multiple pieces of information (e.g., identification of margin line, path of insertion, tooth number identification, gum identification, excess material identification and/or model orientation), the training data may include height maps with targets/labels identifying the types of information that the model is to output.

In one embodiment, the machine learning model is trained to determine a confidence score for each pixel indicating a confidence that the pixel represents a margin line. The confidence scores may be used to determine quality values for segments of the margin line in some embodiments.

Returning to FIG. 11, in one embodiment, a second machine learning model 1175 is trained to modify images (e.g., height maps) in a manner that may correct one or more features of an illustrated tooth and/or that generates a margin line. A set of many (e.g., thousands to millions) original 3D models of teeth may be collected at block 1110A. A corresponding set of many modified 3D models of teeth may also be collected at block 1110B. Additionally, 3D models as they were approved by a doctor and/or dental laboratory may be collected. Each modified 3D model may correspond to a particular original 3D model, and may have been generated by a lab technician manually adjusting a surface of the 3D model (e.g., to add or clarify a margin line in the original 3D model). For each original 3D model one or more height maps are generated. Additionally, for each corresponding modified 3D model one or more height maps are generated. Each height map generated for an original 3D model is generated by projecting the 3D model onto a 2D surface, and each height map generated for a corresponding modified 3D model is generated by projecting the modified 3D model onto the same 2D surface onto which the original 3D model was projected. Accordingly, pairs of height maps may be generated, where a height map from the original 3D model is an input for the second machine learning model and a corresponding height map from the corresponding modified 3D model is a target for the second machine learning model associated with the height map of the original 3D model. At block 1135, the original height maps and corresponding modified height maps may be correlated to generate a training dataset.

At block 1140, a second machine learning model is trained using the training dataset of original and modified height maps (or original and modified images comprising height maps). The second machine learning model (e.g., second deep learning model) may be trained to adjust the surfaces of teeth (e.g., to adjust the surfaces of preparation teeth and/or add a margin line to portion of preparation teeth). The first machine learning model 1155 may identify an existing margin line that already exists in the height map, while the second machine learning model 1175 may change the shape of the surface represented in the height map to add a margin line where a margin line was not previously represented.

Figure 13:
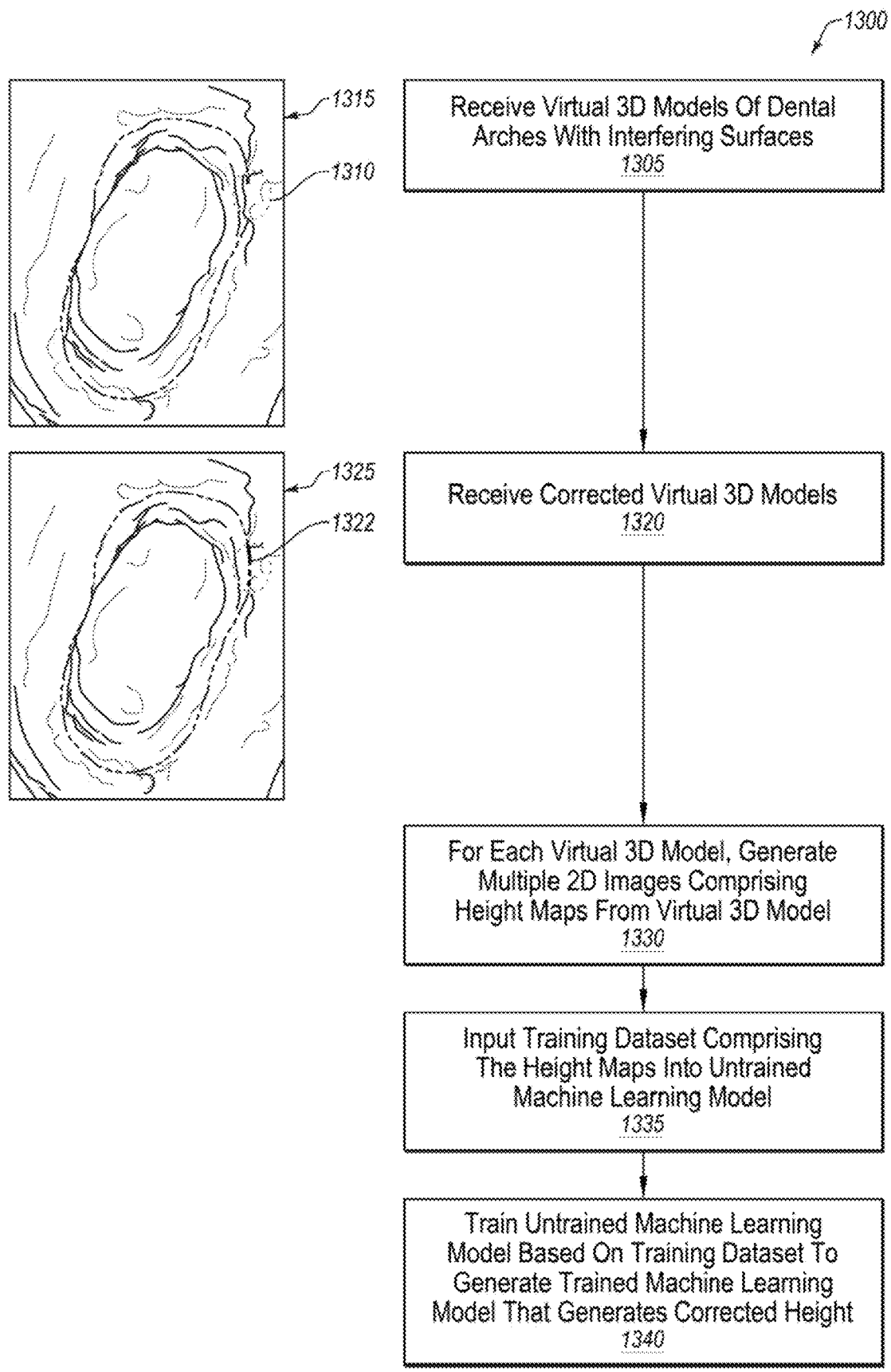
FIG. 13 illustrates a flow diagram for a method of training a machine learning model to correct images of teeth, in accordance with an embodiment.

FIG. 13 illustrates a flow diagram for a method 1300 of training a machine learning model to correct images of teeth, in accordance with an embodiment. At block 1305 of method 1300, processing logic receives original virtual 3D models of dental arches with interfering surfaces (e.g., surfaces that need correction). An example 3D model 1315 is shown with an interfering surface 1310 that obscures a segment of the margin line. At block 1320, processing logic receives associated corrected virtual 3D models in which the interfering surfaces have been removed. An example corrected 3D model 1325 is shown with a fabricated segment of margin line 1322 where the interfering surface 1310 had been located. The corrected 3D models may include additional information that may indicate what actions were taken by a dental lab to correct the 3D model. Examples of such actions include model cleanup of periphery soft tissues, removal of artifacts (e.g., caused by blood, saliva, obstructing objects such as cotton rolls or retraction cord, etc.), and so on. Additionally, model orientation, path of insertion for a restoration or bridge, positioning of the 3D model within a computer aided manufacturing (CAM) template, and/or other information may be included in the corrected 3D models.

At block 1330, for each virtual 3D model processing logic generates one or multiple images comprising height maps from the virtual 3D model. Each image may be generated by projecting the 3D model onto a 2D surface, as described above. Pairs of images (e.g., height maps) are generated for each original virtual 3D model, where a first image is generated from an original 3D model and a second image is generated from a corresponding corrected 3D model. In one embodiment, about 10-150 greyscale height maps are generated for each virtual 3D model. In one embodiment, about 100 greyscale height maps are generated for each virtual 3D model.

At block 1335, processing logic inputs the training dataset comprising the height maps into the untrained machine learning model. At block 1340, processing logic trains the untrained machine learning model based on the training dataset to generate a trained machine learning model that generates corrected or modified height maps with altered surfaces of teeth and/or that include added margin lines. Training may be performed by inputting the images generated from original 3D models into the machine learning model one at a time. For each input image, the machine learning model generates a modified height map. Processing logic may then compare the generated modified height map to the known corrected height map that was generated from the corrected 3D model corresponding to the original 3D model, and back propagation may be performed to update weights of nodes in the machine learning model. This process may be performed repeatedly using a large portion of the training dataset, with each iteration slightly refining the accuracy of the machine learning model. Once the machine learning model is trained, a reserved portion of the training dataset may be used to test the model.

In one embodiment, the machine learning model (or a different machine learning model) is further trained to determine quality scores for surfaces and/or portions of surfaces. For example, a training dataset may include labeled images and/or 3D models with high quality surfaces and labeled images and/or 3D models with low quality surfaces. Such a training dataset may be used to train the machine learning model to determine a surface quality for different surfaces and/or portions of surfaces represented in images. Once such a machine learning model is trained, an image generated by projecting a 3D model onto a 2D surface may be applied to the machine learning model in the manner discussed elsewhere herein, and the machine learning model may output a mask that identifies, for different surface portions (e.g., for each pixel of the input image), a surface quality value. These surface quality values may then be projected onto the 3D model from which the image was generated (e.g., as a texture). The surfaces of the 3D model may then be marked or highlighted according to their surface quality values. For example, surfaces with low surface quality values may be marked or highlighted.

In one embodiment, the machine learning model is additionally trained to identify teeth, gums and/or excess material. In one embodiment, the machine learning model is further trained to determine one or more specific tooth numbers and/or to identify a specific indication (or indications) for an input image. Accordingly, a single machine learning model may be trained to identify and/or correct margin lines and also to identify teeth generally, identify different specific tooth numbers, identify gums and/or identify specific indications (e.g., caries, cracks, etc.). In an alternative embodiment, a separate machine learning model is trained for each specific tooth number and for each specific indication. Accordingly, the tooth number and/or indication (e.g., a particular dental prosthetic to be used) may be indicated (e.g., may be input by a user), and an appropriate machine learning model may be selected based on the specific tooth number and/or the specific indication.

In one embodiment, the machine learning model (or a different machine learning model) is additionally or alternatively trained to determine model orientation, path of insertion for a restoration or bridge, and/or positioning of a 3D model within a CAM template. The machine learning model may be trained to process images (e.g., height maps) of teeth, and to output data (e.g., a vector, matrix, etc.) that contains additional information such as the model orientation, path of insertion and/or positioning of the 3D model within a CAM template, and so on. For example, the machine learning model may output a vector identifying a path of insertion and/or may output a matrix representing model orientation.

In an embodiment, the machine learning model may be trained to output a modified height map with a cleaned up margin line (or other modified surface), optionally with an identification of a margin line, as well as separate information indicating one or more of the above (e.g., path of insertion, model orientation, teeth identification, gum identification, excess material identification, etc.). In one embodiment, the machine learning model (or a different machine learning model) is trained to perform one or more of: output a modified height map with a cleaned up surface and/or a cleaned up margin line, identify teeth represented in height maps, identify gums represented in height maps, identify excess material (e.g., material that is not gums or teeth) in height maps, and/or identify margin line in height maps.

For embodiments in which the machine learning model is trained to output path of insertion, training data may include height maps that include a target path of insertion. For embodiments in which the machine learning model is trained to output a model orientation, training data may include height maps that include a labeled model orientation. For embodiments in which the machine learning model is trained to output a tooth identification, training data may include height maps that include a labeled teeth. For embodiments in which the machine learning model is trained to output a gum identification, training data may include height maps that include a labeled gums. For embodiments in which the machine learning model is trained to output an identification of excess material, training data may include height maps that include a labeled excess material. For embodiments in which the machine learning model is trained to output multiple pieces of information (e.g., identification of margin line, modified height map, path of insertion, tooth number identification, gum identification, excess material identification and/or model orientation), the training data may include height maps with targets/labels identifying the types of information that the model is to output.

Referring back to FIG. 11, The first and/or second trained models 1155, 1175 may be trained using embeddings comprising greyscale images that include height maps (also referred to simply as height maps). An embedding may be an input for a machine learning model that has been projected into a more convenient representation space. In some embodiments, the embeddings include the greyscale image and a time stamp. Scans may change over time, and the time stamp may provide additional data that is usable to further identify a margin line and/or adjust a surface of a tooth. In some embodiments, different portions of the 3D model may be generated from blended images, each of which may have an associated time stamp. An image generated from the 3D model may include one or more time stamps of the blended images used to generate the portion of the 3D model represented in the projected image. Time stamps may be associated with particular pixels. For example, a first set of pixels may include a first time stamp from a first blended image and a second set of pixels may include a second time stamp from a second blended image.

Embodiments have been described with reference to generated images that are generated by projecting a 3D model onto a 2D surface. Alternatively, or additionally, a new image may be a blended image generated from intraoral scan data. In such an instance, the blended image may include a time stamp.

In some embodiments, the embeddings include the greyscale image and an associated color image. The color image may be generated from the 3D model by projecting the 3D model onto the same 2D surface onto which the 3D model is projected to generate the height map. The color data may improve an accuracy of identifying a margin line and/or improve an accuracy of modifying an image/height map.

In some embodiments, generic first and second trained models may be generated that are agnostic to doctor and dental lab. In other embodiments, first and second trained models may be trained using embeddings that include height maps as well as identification of a doctor and/or a dental lab. The information on doctor and/or lab may be input when new images are input into the trained machine learning models to improve an accuracy of the models. Alternatively, separate models may be generated for particular doctors, for particular dental labs, and/or for specific combinations of doctors and dental labs. Such models may then be updated continuously or periodically as new data is received for the particular doctors and/or dental labs. Customized machine learning models may provide increased accuracy. In some embodiments, a generic model is used initially (e.g., for a new doctor, new lab or new doctor/lab combination). As new data is received for the new doctor, new lab, or new doctor/lab combination, the new data may be used to refine the model for the particular doctor and/or dental lab, thereby providing a customized experience.

In some embodiments, the trained machine learning model may be continually trained (e.g., via reinforcement learning). For example, a trained machine learning model may be used to process images generated from 3D models, and the output of the machine learning model may be used to update the 3D model. The updated 3D model generated based on the output of the machine learning model may be accepted or rejected by a doctor or a dental lab. If the updated 3D model is rejected, then the doctor or dental lab may manually correct the 3D model. In such an instance, the manually corrected 3D model may be projected onto the same plane used for the image and modified image. The projected image of the manually corrected 3D model may then be used as a target. The original image and/or the modified image may be used to further train the machine learning model, with the projected image of the manually corrected 3D model as the target, to further refine the machine learning model.

Figure 14:
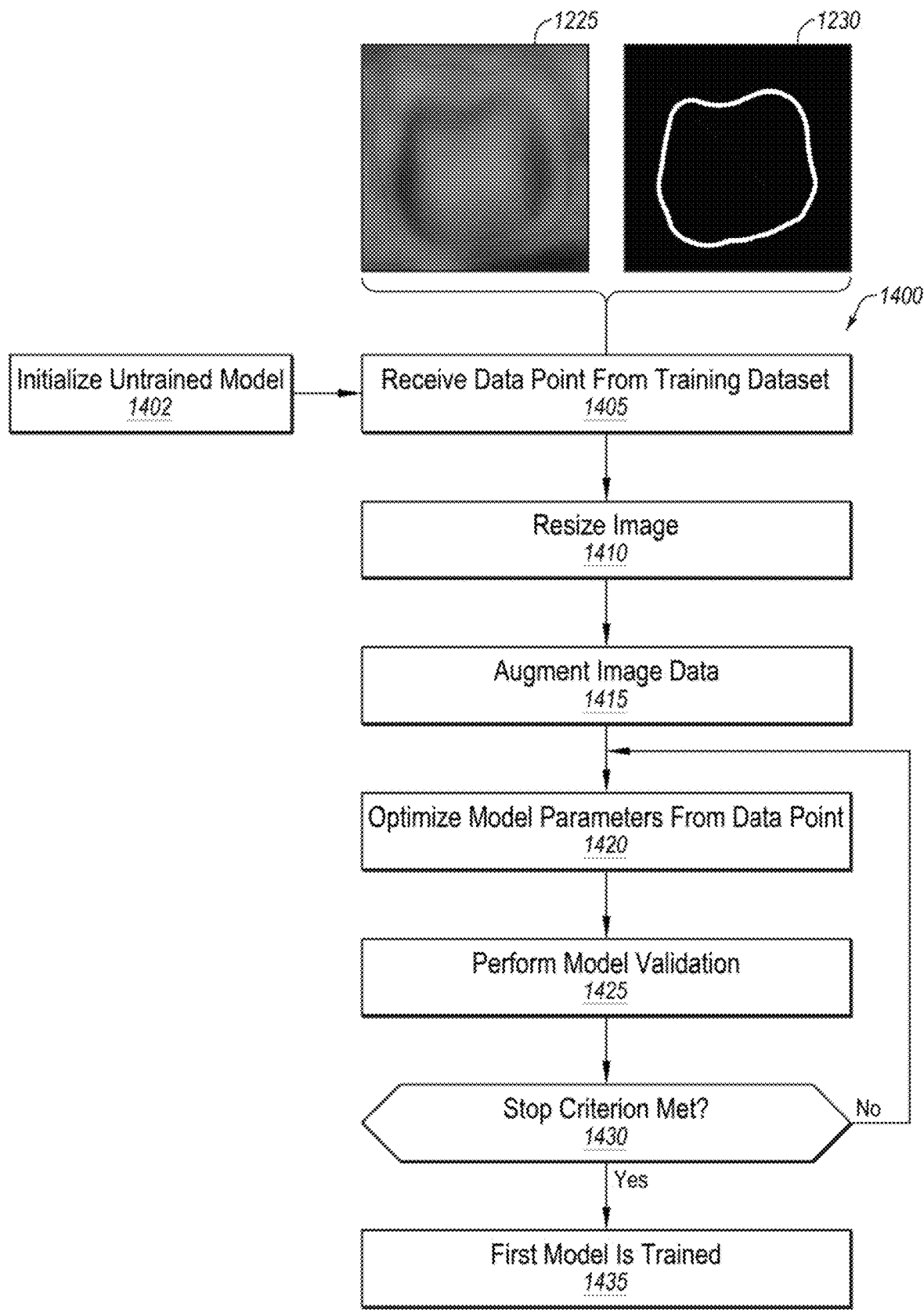
FIG. 14 illustrates a flow diagram for a method of training a machine learning model using image data, in accordance with an embodiment.

FIG. 14 illustrates a flow diagram for a method 1400 of training a machine learning model using image data, in accordance with an embodiment. Method 1400 may be performed to train the first machine learning model 1155 and/or second machine learning model 1175, and may be performed in conjunction with method 1200 and/or method 1300 in embodiments.

At block 1402 of method 1400, an untrained machine learning model is initialized. The machine learning model that is initialized may be a deep learning model such as an artificial neural network. One type of artificial neural network that may be initialized and then trained is a MobileNet. In one embodiment, the MobileNet is initialized with an inception module. Initialization of the artificial neural network may include selecting starting parameters for the neural network. The solution to a non-convex optimization algorithm depends at least in part on the initial parameters, and so the initialization parameters should be chosen appropriately. In one embodiment, parameters are initialized using Gaussian or uniform distributions with arbitrary set variances.

At block 1405, the untrained machine learning model receives a first data point from a training dataset. The first data point may be, for example, image/height map 1225 along with mask 1230 that shows a margin line. Method 1400 is shown with an example height map 1225 and mask 1230 used to train a machine learning model to identify margin lines. However, method 1400 may also be performed to train a machine learning model to modify height maps/images of teeth to correct those images and/or add margin lines to those images.

At block 1410, the mask and/or the image may be resized. For example, the machine learning model may be usable for images having certain pixel size ranges, and the image may be resized if it falls outside of those pixel size ranges. Training images may come in different sizes. However, many deep learning algorithms only accept image having a fixed size. Therefore, images in the training dataset (and their accompanying masks) may be resized so that they have the fixed size. The images may be resized, for example, using methods such as nearest-neighbor interpolation or box sampling. At block 1415, the image data may then be augmented. Training of large-scale neural networks generally uses tens of thousands of images, which are not easy to acquire in many real-world applications. Data augmentation can be used to artificially increase the effective sample size. Common techniques include random rotation, shifts, shear, flips and so on to existing images to increase the sample size.

At block 1420, processing logic optimizes parameters of the machine learning model from the data point. The machine learning model applies a classification or label to the image based on its current parameter values. An artificial neural network includes an input layer that consists of values in a data point (e.g., intensity values and/or height values of pixels in the image 1225). The next layer is called a hidden layer, and nodes at the hidden layer each receive one or more of the input values. Each node contains parameters (e.g., weights) to apply to the input values. Each node therefore essentially inputs the input values into a multivariate function (e.g., a non-linear mathematical transformation) to produce an output value. A next layer may be another hidden layer or an output layer. In either case, the nodes at the next layer receive the output values from the nodes at the previous layer, and each node applies weights to those values and then generates its own output value. This may be performed at each layer. A final layer is the output layer, where there is one node for each class. For the artificial neural network being trained, there may be a first class (no margin line) and a second class (margin line). Moreover, that class is determined for each pixel in the image. For each pixel in the image, the final layer applies a probability that the pixel of the image belongs to the first class (no margin line) and a probability that the pixel of the image belongs to the second class (margin line).

Processing logic compares the classification, label or other output of the machine learning model (e.g., a modified image) to the provided classification(s), label(s) or other target (in this case mask 1230) to determine one or more classification error. An error term or delta may be determined for each node in the artificial neural network. Based on this error, the artificial neural network adjusts one or more of its parameters for one or more of its nodes (the weights for one or more inputs of a node). Parameters may be updated in a back propagation manner, such that nodes at a highest layer are updated first, followed by nodes at a next layer, and so on. An artificial neural network contains multiple layers of "neurons", where each layer receives as input values from neurons at a previous layer. The parameters for each neuron include weights associated with the values that are received from each of the neurons at a previous layer. Accordingly, adjusting the parameters may include adjusting the weights assigned to each of the inputs for one or more neurons at one or more layers in the artificial neural network.

Once the model parameters have been optimized, model validation may be performed at block 1425 to determine whether the model has improved and to determine a current accuracy of the deep learning model. At block 1430, processing logic determines whether a stopping criterion has been met. A stopping criterion may be a target level of accuracy, a target number of processed images from the training dataset, a target amount of change to parameters over one or more previous data points, a combination thereof and/or other criteria. In one embodiment, the stopping criteria is met when at least a minimum number of data points have been processed and at least a threshold accuracy is achieved. The threshold accuracy may be, for example, 70%, 80% or 90% accuracy. In one embodiment, the stopping criteria is met if accuracy of the machine learning model has stopped improving. If the stopping criteria is not met, the method may return to block 1420 to further optimize the model based on another data point from the training dataset. Alternatively, the method may return to block 1405 in an embodiment. If the stopping criteria has been met, the method continues to block 1435 and a machine learning model is trained. As noted herein, the machine learning model may be an artificial neural network (or other deep learning model) such as a MobileNet. However, other types of machine learning models may also be used.

A first machine learning model that may be trained may output, for an input image (e.g., an input image comprising a height map or an input height map), a probability map that has a same resolution as the input image (e.g., the same number of horizontal and vertical pixels). The probability map may be a binary mask that includes a first value for a pixel if the pixel represents a margin line and a second value for the pixel if the pixel does not represent a margin line. Alternatively, the probability map may include numerical values ranging from 0 to 1, where each pixel is assigned a numerical value that represents a probability from 0% to 100% that the pixel represents a margin line. Accordingly, the trained machine learning model makes a pixel level decision for each pixel in an input image as to whether that pixel represents a margin line and/or as to a probability that the pixel represents a margin line.

A second machine learning model that may be trained may output, for an input image (e.g., an input image comprising a height map or an input height map), a modified output image that has a same resolution as the input image. The modified output image may be similar to the input image, but may have an adjusted surface in which a depiction of an obscuring object such as blood, saliva, soft tissue (e.g., gums), retraction cord, etc. has been removed and a depiction of an underlying tooth surface (e.g., including a margin line) is added. Accordingly, the trained machine learning model makes a pixel level decision for each pixel in an input image as to whether that pixel should be adjusted and/or how the pixel should be adjusted to correct the input image.

Returning again to FIG. 11, once the first machine learning model is trained, that trained machine learning model is stored in model storage 1145. Similarly, once the second machine learning model is trained, that trained machine learning model is stored in model storage 1145. Model storage 1145 may include storage of one or more machine learning models in a permanent storage, such as a storage server, which may include solid state storage devices, hard disk drives, tape back drives, and so on.

The model application workflow 1117 begins with receipt and/or generation of a new 3D model 1148 of one or more dental site (e.g., of a preparation tooth and/or adjacent teeth). In one embodiment, the new 3D model is generated from intraoral scan data generated by a doctor. For example, the doctor may perform an intraoral scan of a patient using scanner 150, and a 3D model may be generated from the intraoral scan. In one embodiment, individual intraoral images generated during the intraoral scan are processed using a third machine learning model during image capture. The third machine learning model may identify and remove soft tissues in intraoral images. These modified intraoral images may then be used to generate the 3D model. It may be easier for processing logic to detect margin lines from 3D models generated using such modified intraoral images.

At block 1149, a new image (e.g., a new height map) 1150 is generated by projecting the 3D model (or a portion thereof) onto a 2D surface. The new image 1150 is then input into first trained model 1155, which may have been trained as set forth above. The first trained machine learning model 1155 determines a margin line in the new image 1150 and outputs a probability map, where each point in the probability map corresponds to a pixel in the new image and indicates a probability that the pixel represents a margin line. At block 1165, the probability map 1160 is projected onto the 3D model to update the 3D model. In one embodiment, the probability information from the probability map is projected onto the 3D model as a texture. The updated 3D model may then include, for one or more points, vertexes or voxels of the 3D model (e.g., vertexes on a 3D mesh that represents the surface of the 3D model), a probability that the point, vertex or voxel represents a margin line. At block 1168, processing logic may then compute the margin line based on the probability values associated with the points on the surface of the 3D model. The margin line may be computed by using a cost function that finds a contour that includes a connected collection of points that together have a minimum cost. Computation of the margin line is described in greater detail with reference to FIG. 16. The margin line may then be drawn on the 3D model. In some embodiments, different cost values are computed for different segments of the margin line. The different cost values may be compared to a maximum cost, and if any cost value exceeds the maximum cost, an associated margin line segment may be highlighted in the 3D model. Highlighted segments of the margin line represent segments that are unclear, inaccurate, and/or otherwise unacceptable.

The new image 1150 may additionally or alternatively be input into second trained model 1175, which may have been trained as set forth above. In one embodiment, the new image 1150 is input into the second trained model 1175 if one or more areas of the new 3D model are identified as unclear, inaccurate, or otherwise unacceptable. In one embodiment, the new image 1150 is input into the second trained model if one or more segments of margin line have been identified as unacceptable. Alternatively, the updated 3D model 1165 may be used to generate a different new image, which may be input into the second trained model 1175.

The second trained machine learning model 1175 generates a modified image (e.g., modified height map) 1180. At block 1185, the modified image 1180 is used to update the 3D model. In one embodiment, data from the modified image 1180 is used to overwrite portions of the 3D model, changing a shape of a surface of the 3D model. In addition to the modified image, a probability map may also be generated for the modified image, where the probability map indicates the probability that pixels of the modified image represent a margin line. The probability map may be used to determine probabilities of points on the surface of the 3D model representing the margin line, and ultimately to draw the margin line on the 3D model. All segments of the margin line in the updated 3D model should be clear and have acceptable levels of accuracy. Accordingly, a margin line may be computed and then drawn on the 3D model.

In one embodiment, a new image is generated from the updated 3D model, and the new image is processed by the first trained model to update a marking of the margin line on the 3D model (e.g., the operations of blocks 1155-1169 may be repeated using the new image generated from the updated 3D model.

Figure 15:
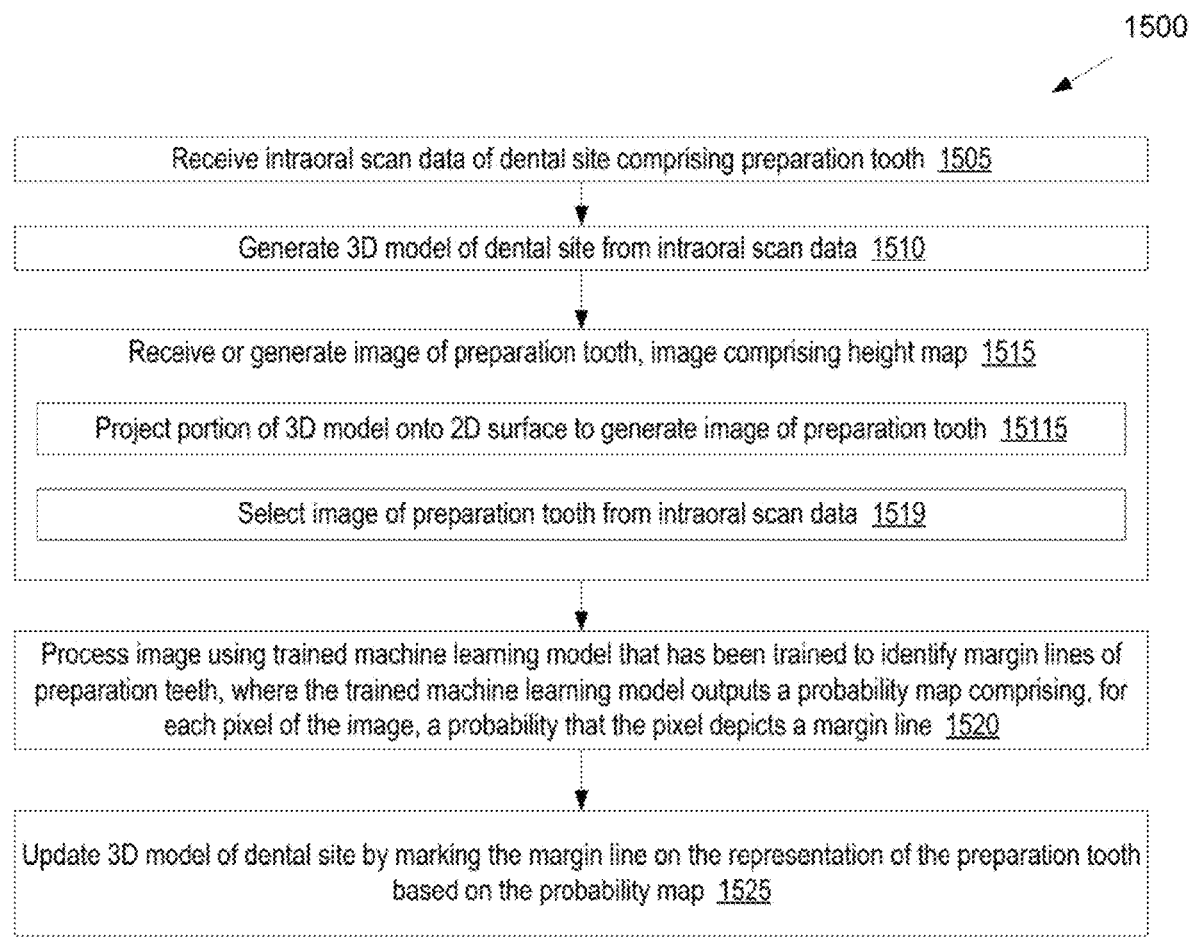
FIG. 15 illustrates a flow diagram for a method of identifying a margin line in a 3D model of a dental site, in accordance with an embodiment.
Figure 16:
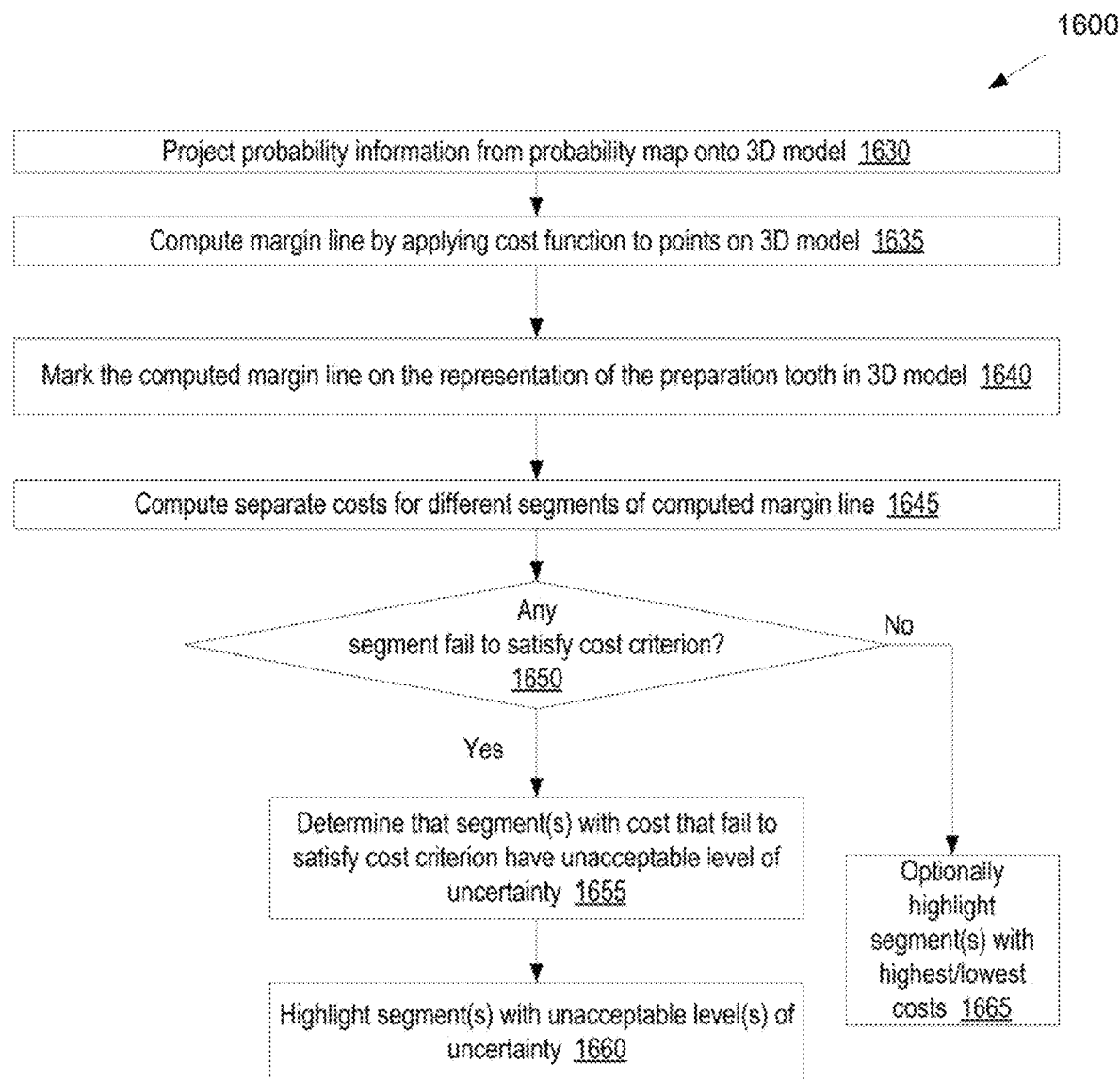
FIG. 16 illustrates a further flow diagram for a method of identifying a margin line in a 3D model of a dental site, in accordance with an embodiment.

FIG. 15 illustrates a flow diagram for a method 1500 of identifying a margin line in a 3D model of a dental site, in accordance with an embodiment. At block 1505 of method 1500, processing logic receives intraoral scan data of a dental site comprising a preparation tooth. At block 1510, processing logic generates a 3D model of the dental site from the intraoral scan data.

At block 1515, processing logic receives or generates an image of the preparation tooth, where the image comprises a height map of the preparation tooth. For example, a greyscale height map may be received or generated. In one embodiment, at block 1518 processing logic projects the 3D model onto a 2D surface to generate the image of the preparation tooth. In one embodiment, at block 1519 processing logic selects an intraoral image from the intraoral scan data. In one embodiment, the intraoral image is a blended image contrasted from combining together multiple different distinct intraoral images.

At block 1520, processing logic processes the image using a trained machine learning model that has been trained to identify margin lines of preparation teeth. The trained machine learning model may output a probability map comprising, for each pixel of the image, a probability that the pixel represents a margin line. In one embodiment, the trained machine learning model corresponds to the first trained model 1155 of FIG. 11. In one embodiment, multiple different machine learning models have been trained, where each machine learning model was trained for a specific tooth number and/or for a specific indication. An appropriate machine learning model may be selected based on the specific tooth number and/or the specific indication, and the image (e.g., height map) is input into the selected machine learning model.

At block 1525, processing logic updates a 3D model of a dental site by marking the margin line on the representation of the preparation tooth based on the probability map. In one embodiment, method 1600 is performed to mark the margin line on the 3D model.

The operations of blocks 1515-1525 may be performed for many (e.g., up to about a hundred or more) images generated from a single 3D model of a dental site. The data from the multiple images in the aggregate may provide an accurate representation of the margin line in embodiments.

FIG. 16 illustrates a further flow diagram for a method 1600 of identifying a margin line in a 3D model of a dental site, in accordance with an embodiment. At block 1630 of method 1600, processing logic projects probability information from a probability map (e.g., that was output by a machine learning model) onto the 3D model. The probability map may be associated with a height map that was generated from the 3D model. The height map may be used to determine, for each pixel in the height map, a corresponding point on the 3D model. The probability of the associated pixel may then be assigned to the determined corresponding point on the 3D model as a texture.

At block 1635, processing logic computes a margin line by applying a cost function to the points on the 3D model. In one embodiment, processing logic generates a matrix that identifies, for each point (e.g., edge, vertex, voxel, etc. on a surface of the 3D model), a probability that the point represents a margin line. For example, entries in the matrix that have nt chance of representing the margin line have an assigned 0% probability.

Processing logic uses the cost function to create a closest contour going through points with high probabilities of representing the margin line. In one embodiment, a total cost of the contour that is drawn for the margin line is the sum of all edges (e.g., vertexes) included in the margin line, adjusted by weights associated with each of the vertexes. Each weight for a vertex may be a function of the probability assigned to that vertex. The cost for that vertex being included in the margin line may be approximately 1/(A+P), where A is a small constant and P is the probability of the vertex representing the margin line. The smaller the probability for a vertex, the larger the cost of that vertex being included in the margin line. Costs may also be computed for segments of the margin line based on a sum of the costs of the vertexes included those segments. When probability is close to 100%, then cost is approximately 1 adjusted by length.

In one embodiment, a path finding operation or algorithm is applied to the 3D model using values from the matrix as a cost basis. Any pathfinding algorithm may be used. Some examples of possible path finding algorithms to use include dynamic programming, Dijkstra's algorithm, A* search algorithm, an incremental heuristic search algorithm, and so on. A pathfinding algorithm may apply a cost function to determine a path of the margin line.

A pathfinding algorithm that uses probability of representing the margin line in the matrix as a cost basis may search for a path with a maximal cost or a path with a minimal cost. The cost function described above searches for minimum cost using a function that is based on an inverse of probability. Alternatively, a cost function may be used that is based directly on probability, where the maximum cost is searched for. If a pathfinding algorithm is run to maximize cost, then a path between vertexes will be determined that results in a maximum aggregate of probability values. The probability scores of the vertexes may be input into the pathfinding algorithm to find the path that has the maximal cost for the probability score. The path finding algorithm may be used to define a contour that represents the margin line.

At block 1640, processing logic marks the computed margin line on the representation of the preparation tooth in the 3D model. At block 1645, processing logic computes separate costs for different segments of the margin line as described above. For example, processing logic may determine multiple segments of the margin line, each segment including a collection of connected or adjacent vertexes. For each segment, processing logic may use the cost function to compute a cost for the segment. Cost values may be computed for overlapping and/or non-overlapping segments. Alternatively, such separate costs may have been computed at block 1635.

At block 1650, processing logic determines whether any of the segments has a cost value/score that fails to satisfy a cost criterion. For example, processing logic may determine whether any of the segments has a cost that exceeds a cost threshold (if the cost function optimizes for minimal cost). Alternatively, processing logic may determine whether any segment has a cost value/score that is below a cost threshold (if the cost function optimizes for maximal cost). If all segments meet the cost criterion, the method continues to block 1665. If any segment fails to satisfy the cost criterion, the method continues to block 1655.

At block 1665, processing logic optionally highlights segments of the margin line that satisfied the cost criterion, but that came close to failing the cost criterion. For example, processing logic may highlight the segments with the highest costs.

At block 1655, processing logic determines that one or more segments of the margin line that failed the cost criterion has an unacceptable level of uncertainty or clarity. At block 1660, processing logic highlights those segments of the margin line with unacceptable levels of uncertainty or clarity.

Figure 17:
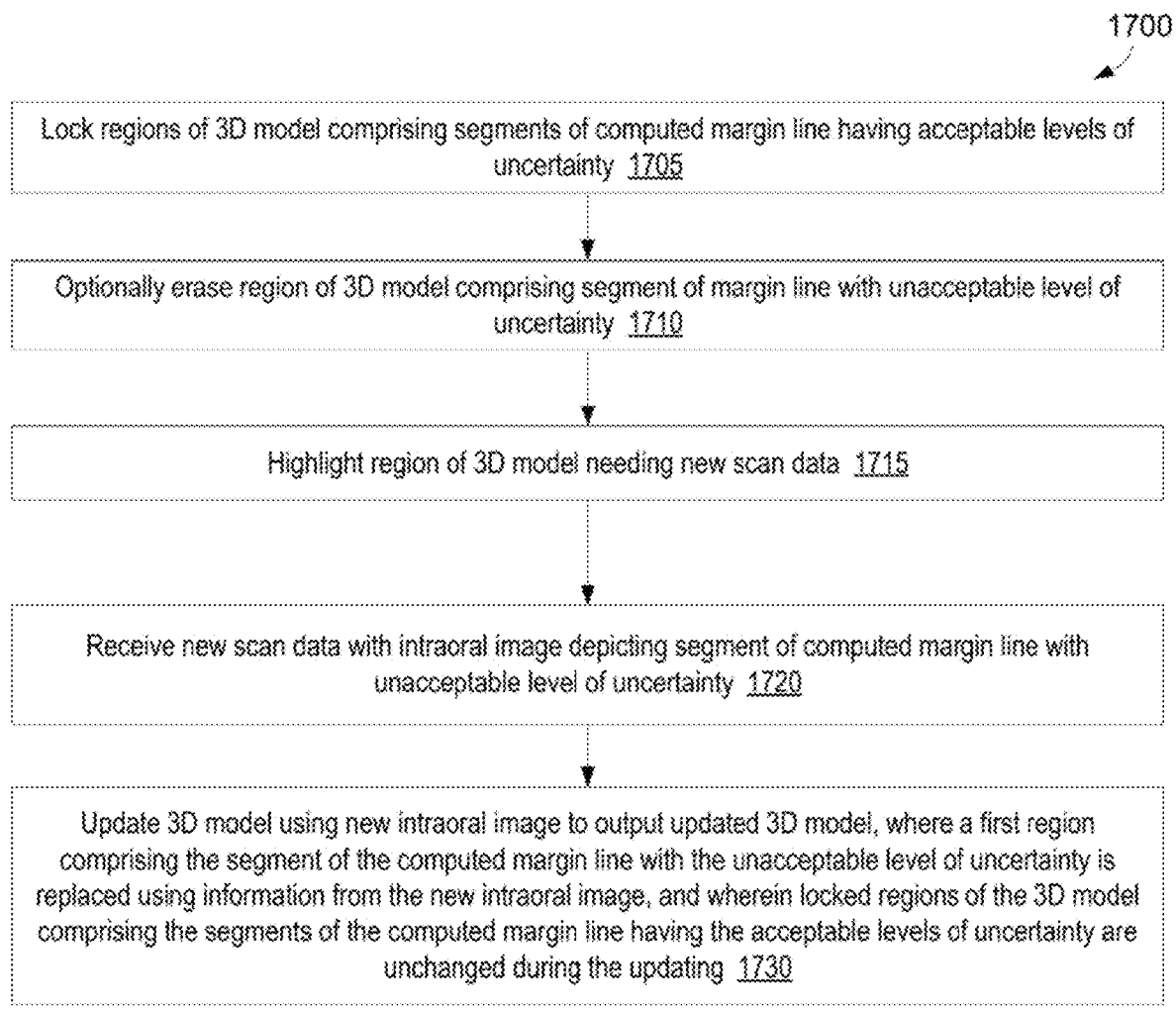
FIG. 17 illustrates a flow diagram for a method of updating a 3D model of a dental site, in accordance with an embodiment.

FIG. 17 illustrates a flow diagram for a method 1700 of updating a 3D model of a dental site, in accordance with an embodiment. Method 1700 may be performed, for example, after execution of method 1500 and/or method 1600 in some embodiments.

At block 1705 of method 1700, processing logic automatically locks one or more regions of the 3D model of the dental site(s) comprising segments of a computed margin line having acceptable levels of uncertainty (e.g., areas depicting segments of the margin line that satisfied a margin line cost criterion). At block 1710, processing logic optionally automatically erases a region of the 3D model comprising a segment of the margin line with an unacceptable level of uncertainty (e.g., that had a cost that failed to satisfy a cost criterion).

At block 1715, processing logic may highlight a region of the 3D model that needs new scan data (e.g., the area that was erased). Processing logic may additionally notify a doctor to generate one or more intraoral scans of the portion of a preparation tooth associated with the region of the 3D model that was erased.

At block 1720, processing logic receives new scan data that includes at least one intraoral image depicting the segment of the computed margin line with the unacceptable level of uncertainty. At block 1730, processing logic updates the 3D model using the new intraoral image to output an updated 3D model. A first region of the 3D model previously comprising the segment of the computed margin line with the unacceptable level of uncertainty is replaced using information from the new intraoral image (or images). Locked regions of the 3D model comprising segments of the computed margin line having acceptable levels of uncertainty are unchanged during the updating.

Figure 18:
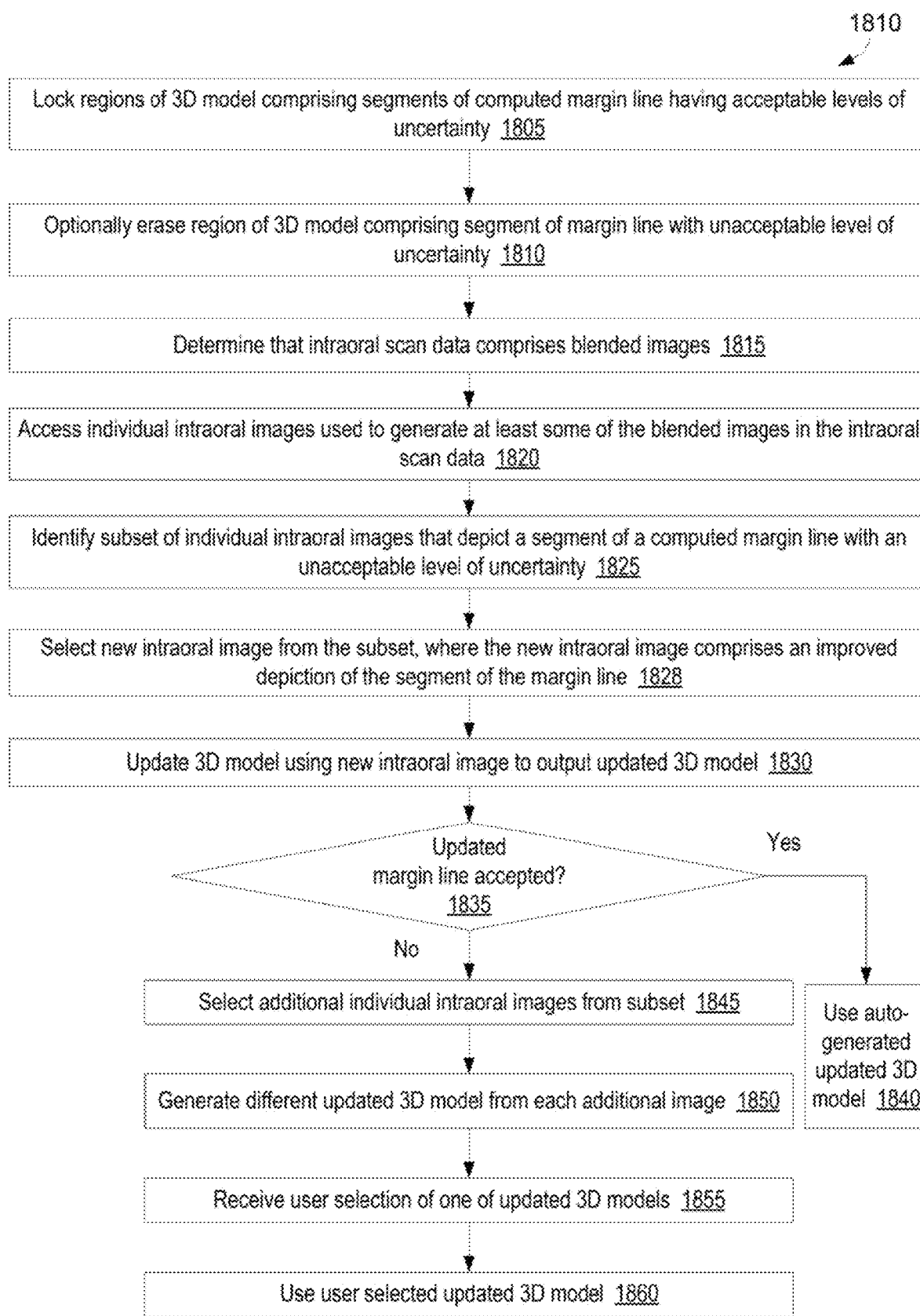
FIG. 18 illustrates another flow diagram for a method of updating a 3D model of a dental site, in accordance with an embodiment.

FIG. 18 illustrates another flow diagram for a method 1800 of updating a 3D model of a dental site, in accordance with an embodiment. Method 1800 may be performed, for example, after execution of method 800 and/or method 1600 in some embodiments.

At block 1805 of method 1800, processing logic automatically locks one or more regions of the 3D model of the dental site(s) comprising segments of a computed margin line having acceptable levels of uncertainty (e.g., areas depicting segments of the margin line that satisfied a margin line cost criterion). At block 1805, processing logic optionally automatically erases a region of the 3D model comprising a segment of the margin line with an unacceptable level of uncertainty (e.g., that had a cost that failed to satisfy a cost criterion).

At block 1815, processing logic determines that the intraoral scan data used to generate the 3D model comprises blended intraoral images, where each blended intraoral image is an image that is based on a combination of multiple other distinct intraoral images. At block 1820, processing logic accesses individual intraoral images used to generate at least some of the blended images in the intraoral scan data. At block 1825, processing logic identifies a subset of the individual intraoral images that depict a segment of a computed margin line with an unacceptable level of uncertainty.

At block 1828, processing logic selects a new intraoral image from the subset, where the new intraoral image comprises an improved depiction of the segment of the margin line. For example, some of the distinct intraoral images in a particular blended image used to generate the 3D model may have included a collapsed gum that obscures the margin line. However, one or more other distinct intraoral images used to generate the blended image may show the gum in a non-collapsed position. The intraoral image in which the gum is not collapsed may be selected. In one embodiment, images are assessed by processing the images using the first trained model 1155 of FIG. 11 or another trained machine learning model that identifies margin lines.

In one embodiment, the intraoral images are assessed by processing the intraoral images using a trained machine learning model that has been trained to identify for a given intraoral image a quality of the margin line depicted in the intraoral image. The machine learning model may have been trained using a training dataset that includes first labeled intraoral images with unacceptable margin lines and second labeled intraoral images with acceptable margin lines. In one embodiment, the trained machine learning model, on processing an intraoral image of a preparation tooth, outputs an indication that the image comprises an acceptable margin line or an unacceptable margin line. In one embodiment, the trained machine learning model, on processing an intraoral image of a preparation tooth, outputs a quality score for the margin line.

Each individual intraoral image may have an associated time stamp, which may indicate when that intraoral image was generated in relation to other intraoral images that may be analyzed. In one embodiment, embeddings input into the machine learning model include an intraoral image as well as an associated time stamp. In one embodiment, a recurrent neural network (RNN) is used for the machine learning model. Intraoral images may be input into the machine learning model in ascending order based on time stamp, and the machine learning model may assess quality of margin lines based in part on changes between intraoral images. For example, the machine learning model may be able to identify that a margin line quality is getting worse over time (e.g., because a gum is collapsing after a retraction material has been removed, because a patient is bleeding over time, etc.). Accordingly, the machine learning model may detect a deterioration of the surface (e.g., of a margin line). Additionally, the machine learning model may identify when a doctor wiped blood away, or performed some other action that caused subsequent images to be improvements over prior images.

At block 1830, processing logic updates the 3D model using the new intraoral image that was selected from the subset of intraoral images used to generate the blended intraoral image depicting the region with the unacceptable margin line segment.

At block 1835, processing logic determines whether the 3D model with the updated margin line is accepted. The updated 3D model may be presented to a doctor, who may review and either accept or reject the 3D model (and/or the margin line or a specific segment of the margin line for the 3D model). If the 3D model is accepted, the method proceeds to block 1840 and the auto-generated updated 3D model is used. If the 3D model is not accepted, the method continues to block 1845.

At block 1845, processing logic selects one or more additional individual intraoral images from the subset. At block 1850, processing logic generates a different updated 3D model from each of the additional individual intraoral images that were selected. A user may then scroll through different options for the updated 3D model, where each option is based on use of a different individual intraoral image. At block 1855, processing logic receives a user selection of one of the updated 3D models. At block 1860, processing logic uses the selected updated 3D model (e.g., to send to a dental lab).

Figure 19:
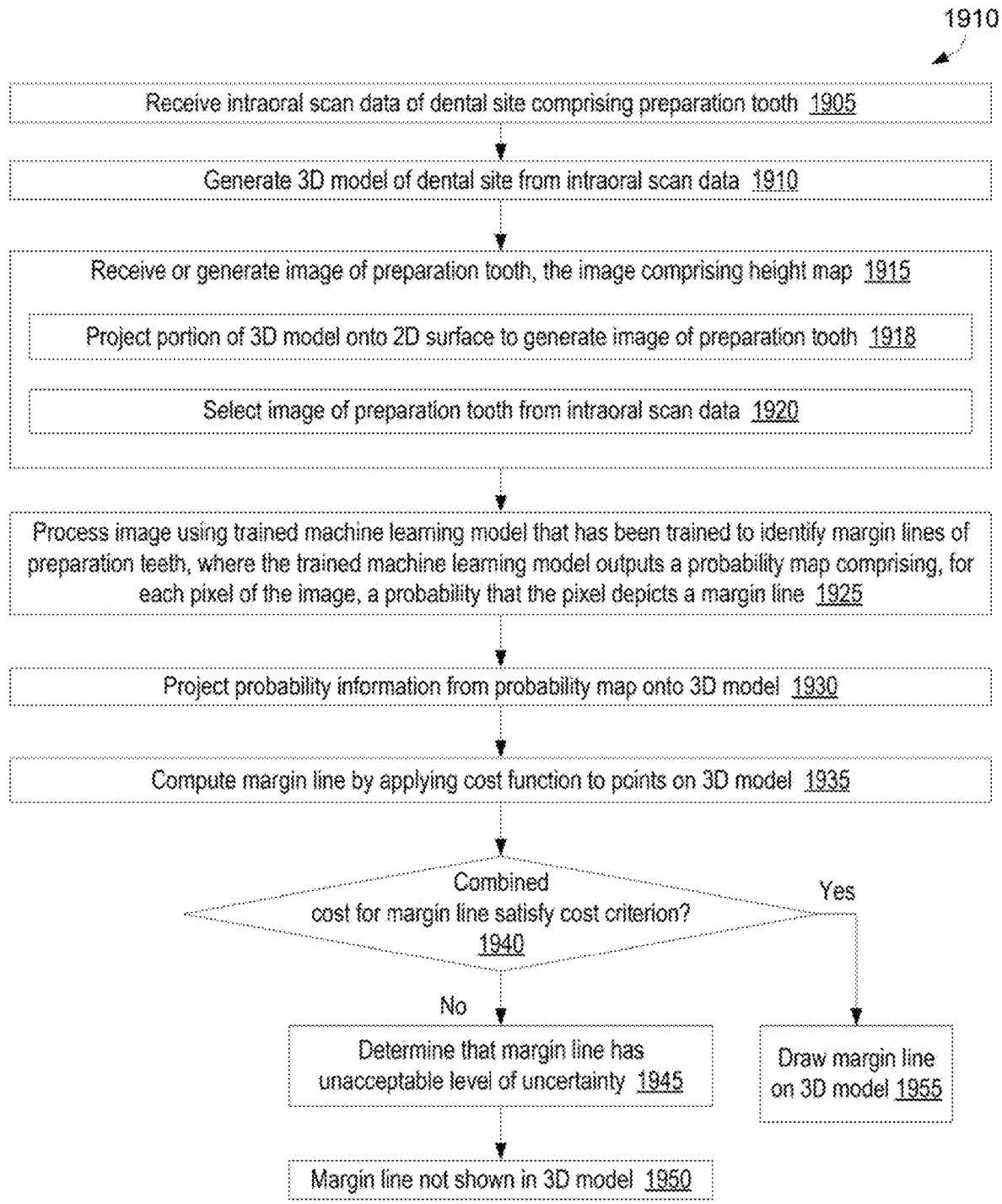
FIG. 19 illustrates another flow diagram for a method of identifying a margin line in a 3D model of a dental site, in accordance with an embodiment.

FIG. 19 illustrates another flow diagram for a method 1900 of identifying a margin line in a 3D model of a dental site, in accordance with an embodiment. At block 1905 of method 1900, processing logic receives intraoral scan data of a dental site comprising a preparation tooth. At block 1910, processing logic generates a 3D model of the dental site from the intraoral scan data.

At block 1915, processing logic receives or generates an image of the preparation tooth, where the image comprises a height map of the preparation tooth. For example, a greyscale height map may be received or generated. In one embodiment, at block 1918 processing logic projects the 3D model onto a 2D surface to generate the image of the preparation tooth. In one embodiment, at block 1920 processing logic selects an intraoral image from the intraoral scan data. In one embodiment, the intraoral image is a blended image contrasted from combining together multiple different distinct intraoral images.

At block 1925, processing logic processes the image using a trained machine learning model that has been trained to identify margin lines of preparation teeth. The trained machine learning model may output a probability map comprising, for each pixel of the image, a probability that the pixel represents a margin line. In one embodiment, the trained machine learning model corresponds to the first trained model 1155 of FIG. 11.

At block 1930, processing logic projects the probability information from the probability map onto the 3D model. At block 1935, processing logic computes a margin line by applying a cost function to the points of the 3D model. At block 1940, processing logic determines whether the combined cost of the margin line satisfies a cost criterion (e.g., exceeds a cost threshold if a minimum cost is targeted or falls below a cost threshold if a maximal cost is targeted). If the combined cost satisfies the cost criterion, the method proceeds to block 1955 and the margin line is drawn on the 3D model. If the combined cost fails to satisfy the cost criterion, the method continues to block 1945.

At block 1945, processing logic determines that the margin line has an acceptable level of uncertainty. At block 1950, the margin line is not shown in the 3D model.

FIG. 20 illustrates a flow diagram 2000 for a method of correcting a representation of a tooth in a 3D model of a dental site, in accordance with an embodiment. At block 2005 of method 2000, processing logic receives intraoral scan data of a dental site comprising a tooth. The tooth may or may not be a preparation tooth. At block 2010, processing logic generates a 3D model of the dental site from the intraoral scan data. The 3D model comprises a representation of the tooth, and further comprises a representation of an interfering surface that obscures a portion of the tooth. The interfering surface may be or include blood, saliva, soft tissue (e.g., gums), retraction material, and so on.

At block 2015, processing logic receives or generates an image of the preparation tooth, where the image comprises a height map of the preparation tooth. For example, a greyscale height map may be received or generated. In one embodiment, at block 2018 processing logic projects the 3D model onto a 2D surface to generate the image of the preparation tooth. In one embodiment, at block 2019 processing logic selects an intraoral image from the intraoral scan data. In one embodiment, the intraoral image is a blended image contrasted from combining together multiple different distinct intraoral images.

At block 2020, processing logic processes the image to generate a modified image that comprises a modified height map. A portion of the tooth that was obscured by the interfering surface in the image is shown in the modified image. Thus, the representation of the interfering surface may be removed in the modified image.

In one embodiment, at block 2022 the modified height map is generated using a trained machine learning model that has been trained to generate modified height maps of teeth from input height maps. The image may be input into the trained machine learning model, which may output the modified height map. The trained machine learning model may also output a probability map comprising, for each pixel of the image, a probability that the pixel represents a margin line in some embodiments. In one embodiment, the trained machine learning model corresponds to the second trained model 1175 of FIG. 11. In one embodiment, multiple different machine learning models have been trained, where each machine learning model was trained for a specific tooth number and/or for a specific indication. An appropriate machine learning model may be selected based on the specific tooth number and/or the specific indication, and the image (e.g., height map) is input into the selected machine learning model.

At block 2025, processing logic updates a 3D model of the dental site using the modified height map. The 3D model may be updated by replacing a portion of an original surface of the 3D model with an updated surface that is based on the modified height map.

The operations of blocks 815-825 may be performed for many (e.g., up to about a hundred or more) images generated from a single 3D model of a dental site. The data from the multiple images in the aggregate may provide an accurate representation of the margin line in in embodiments.

In some embodiments, the updated 3D model and/or the modified image (e.g., modified height map) may be further processed to determine if the modifications to the 3D model and/or image are acceptable. In one embodiment, blended images were used to generate the 3D model. In such an embodiment, processing logic may access distinct images that were used to generate a blended image associated with the segment of the margin line. The modified image may then be compared to the distinct images, and a distinct image that is closest to the modified image may be selected. The selected image may then be used to update the 3D model rather than the modified image. Alternatively, the selected image may be used to further update the 3D model after the modified image has been used to update the 3D model.

In some embodiments, each distinct image is processed using the machine learning model that generates a probability map for a margin line. In one embodiment, the machine learning model takes as an input an embedding comprising a height map of a tooth and a time stamp. Alternatively, the machine learning model may take as an input an embedding comprising a greyscale height map or an embedding comprising a greyscale height map plus a 2D color image without height information. A cost function may then be applied to the each image to compute a margin line in the image. For each distinct image, the margin line computed from the image may be compared to a margin line identified in the modified image. The distinct image with the margin line that most closely matches the margin line in the modified image may be selected. The selected image may then be used to update the 3D model rather than the modified image. Alternatively, the selected image may be used to further update the 3D model after the modified image has been used to update the 3D model.

In some embodiments, multiple different updated versions of the 3D model are generated, where each version is generated using a different selected image. The different updated versions of the 3D model may be presented to a doctor, who may scroll through the versions and select a version that most closely reflects an actual margin line of a preparation tooth of a patient.

Figure 21:
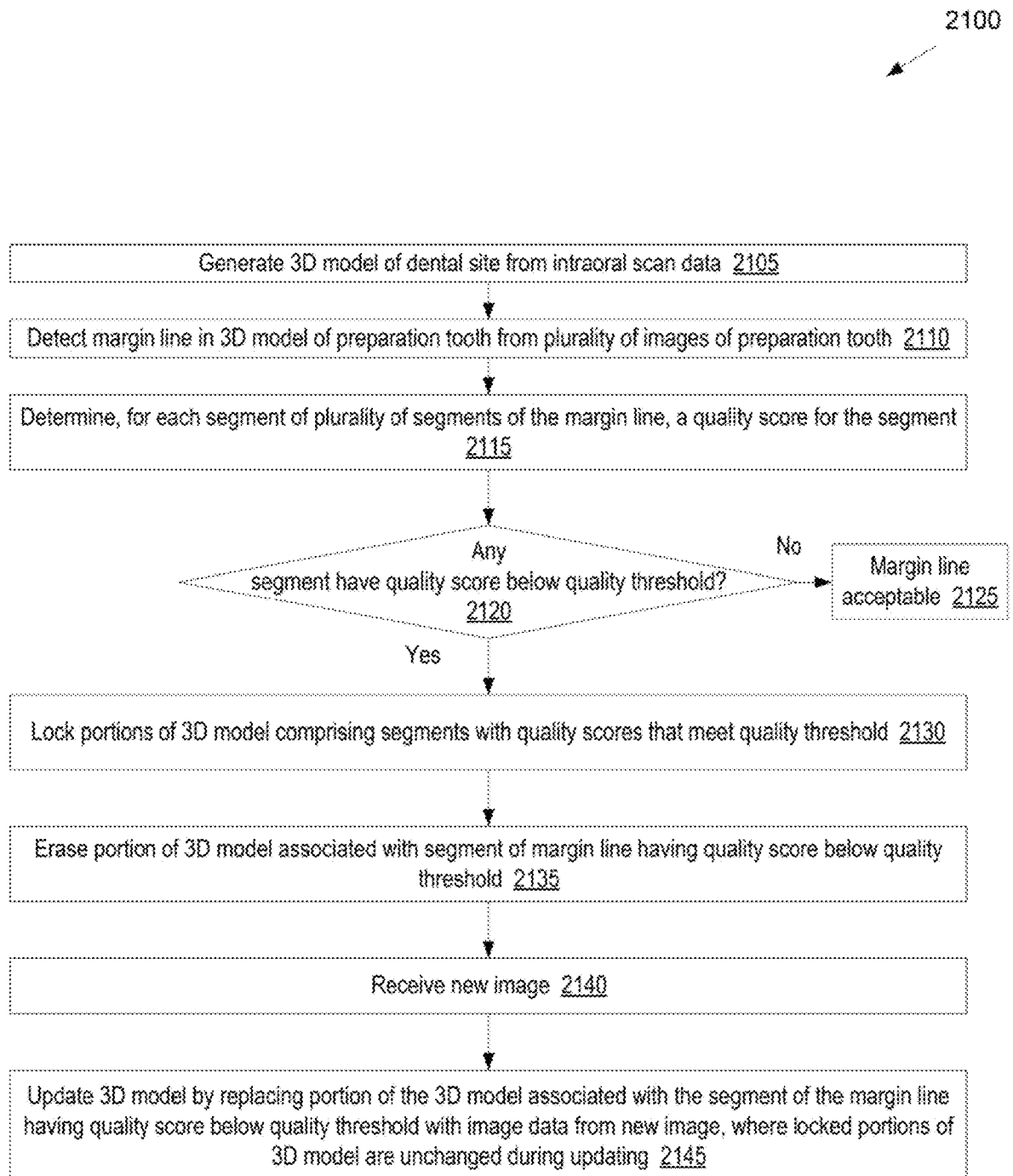
FIG. 21 illustrates a flow diagram for a method of correcting a representation of a margin line of a preparation tooth in a 3D model of a dental site, in accordance with an embodiment.

FIG. 21 illustrates a flow diagram for a method 2100 of correcting a representation of a margin line of a preparation tooth in a 3D model of a dental site, in accordance with an embodiment. At block 2105 of method 2100, processing logic generates a 3D model of a dental site from intraoral scan data. At block 2110, processing logic detects a margin line in the 3D model of the preparation tooth from one or more images of the preparation tooth. In one embodiment, between 10 and 150 greyscale height maps are generated by projecting the 3D model onto multiple different 2D surfaces. At block 2115, processing logic determines, for each segment of a plurality of segments of the margin line, a quality score for the segment.

At block 2120, processing logic determines whether any segment of the margin line has a quality score that is below a quality threshold. A margin line segment may have a quality score that is below the quality threshold, for example, if the margin line segment has a cost that fails to satisfy a cost criterion. For example, a quality score may be computed from a cost computed for the margin line segment. Alternatively, the cost may be used as the quality score. If any quality score is below the quality threshold, the method continues to block 2130. If all of the quality scores meet or exceed the quality threshold, the method continues to block 2125 and the margin line is identified as acceptable.

At block 2130, processing logic may lock one or more portion of the 3D model comprising segments of the margin line with quality scores that meet the quality threshold. At block 2135, processing logic may erase a portion of the 3D model associated with the segment of the margin line having the quality score that is below the quality threshold.

At block 2140, a new image is received. The new image may be an intraoral image that was generated by an intraoral scanner responsive to a notice that the segment of the margin line had a quality score below the quality threshold. Alternatively, the new image may be a previously generated image that is selected to provide an improved depiction of the section of the margin line. For example, blended images may have been used to generate the 3D model, where each blended image is generated from multiple distinct images. The new image may be one such distinct image selected from the available distinct images as described above with regards to selecting distinct images used to create blended images. Alternatively, the new image may be generated automatically by projecting a portion of the 3D model onto a surface to create a height map, and then inputting the height map into a trained machine learning model that has been trained to modify intraoral images (e.g., second trained model 1175 of FIG. 11).

At block 2145, processing logic updates the 3D model by replacing the portion of the 3D model associated with the segment of the margin line having the quality score that is below the quality threshold with image data from the new image. The locked portions of the 3D model may be unchanged by the updating.

Figure 22:
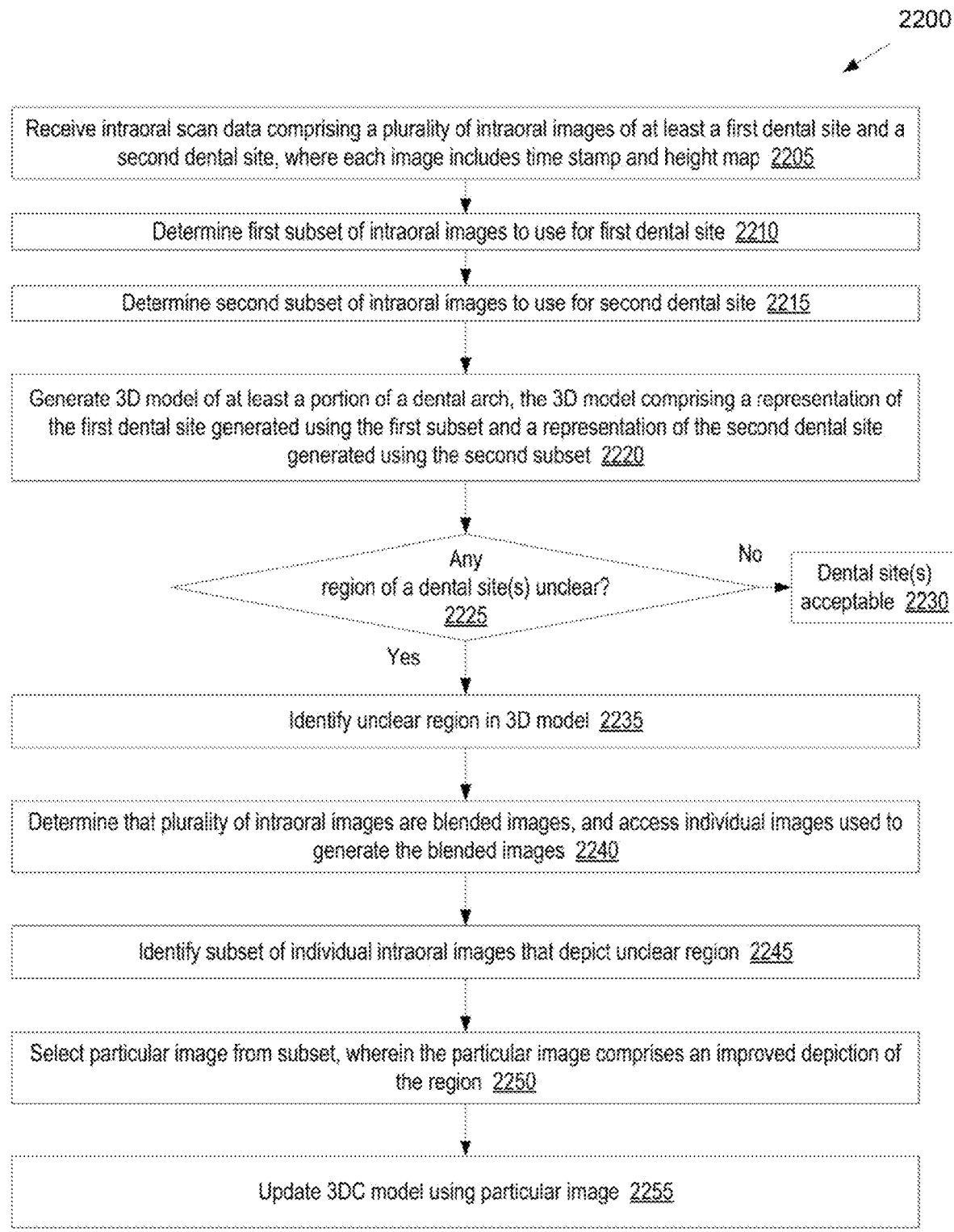
FIG. 22 illustrates a flow diagram for a method of generating a 3D model of multiple dental sites, in accordance with an embodiment.

FIG. 22 illustrates a flow diagram for a method 2200 of generating a 3D model of multiple dental sites, in accordance with an embodiment. At block 2205 of method 2200, processing logic receives intraoral scan data comprising a plurality of intraoral images of at least a first dental site (e.g., a first tooth) and a second dental site (e.g., an adjacent second tooth). Each of the intraoral images may include a time stamp and a height map. In one embodiment, each of the intraoral images is a blended image that is based on blending together multiple distinct intraoral images.

At block 2210, processing logic determines a first subset of the intraoral images to use for generating a portion of a first 3D model that depicts the first dental site. The first subset may be determined based at least in part on a) time stamps of intraoral images in the first subset and b) geometrical data of the intraoral images in the first subset. At block 2215, processing logic determines a second subset of the intraoral images to use for generating a second portion of the 3D model that depicts the second dental site. The second subset may be determined based at least in part on a) time stamps of intraoral images in the second subset and b) geometrical data of the intraoral images in the second subset.

The first subset and second subset may be generated by inputting the plurality of intraoral images into a trained machine learning model that has been trained to grade intraoral images for use in generating 3D models of dental sites. In one embodiment, an embedding is generated for each intraoral image, the embedding comprising the intraoral image (or data from the intraoral image) and the time stamp associated with the intraoral image. The embeddings may be input into the machine learning model. For each intraoral image, the machine learning model may output a first score associated with the first dental site and a second score associated with the second dental site. Alternatively, separate trained machine learning models may be used for each tooth number. Accordingly, the images may be input into a first machine learning model, which outputs first scores for those images, and the images may be input into a second machine learning model that outputs second scores for those images. The first subset may then be determined by selecting those images having a first score that exceeds a quality threshold. The second subset may be determined by selecting those images having a second score that exceeds the quality threshold. In one embodiment, the machine learning model is an RNN. In such an embodiment, the intraoral images may be input into the machine learning model in ascending chronological order.

At block 2225, processing logic determiners whether any region of the dental sites are unclear (e.g., based on one or more of the aforementioned techniques for identifying and/or grading the margin line). If no regions of the dental sites are unclear, the method proceeds to block 2230 and the 3D model is deemed acceptable. If any region of the dental site is identified as being unclear, the method continues to block 2235.

At block 2235, processing logic identifies the unclear region of a dental site. The unclear region may be identified as set forth in the techniques described above. At block 2240, processing logic determines that the plurality of intraoral images are blended images, and accesses individual images used to generate at least some of the blended images.

At block 2245, processing logic identifies a subset of the plurality of individual intraoral images that depict the region that is unclear. At block 2250, processing logic selects a particular image from the subset of the plurality of individual intraoral images, wherein the particular image comprises an improved depiction of the region. The selection may be performed as described above with reference to previous methods. At block 2255, processing logic updates the three-dimensional model using the particular image.

In one embodiment, processing logic generates a plurality of different versions of the updated three-dimensional model, wherein each of the plurality of different versions is based on a different individual intraoral image from the subset of the plurality of individual intraoral images. The different versions may then be presented to a doctor. For example, the doctor may scroll or swipe through the different options until a suitable option is displayed. Processing logic may then receive a user selection of a particular version of the updated three-dimensional model, and may use that version of the updated 3D model.

Figure 23:
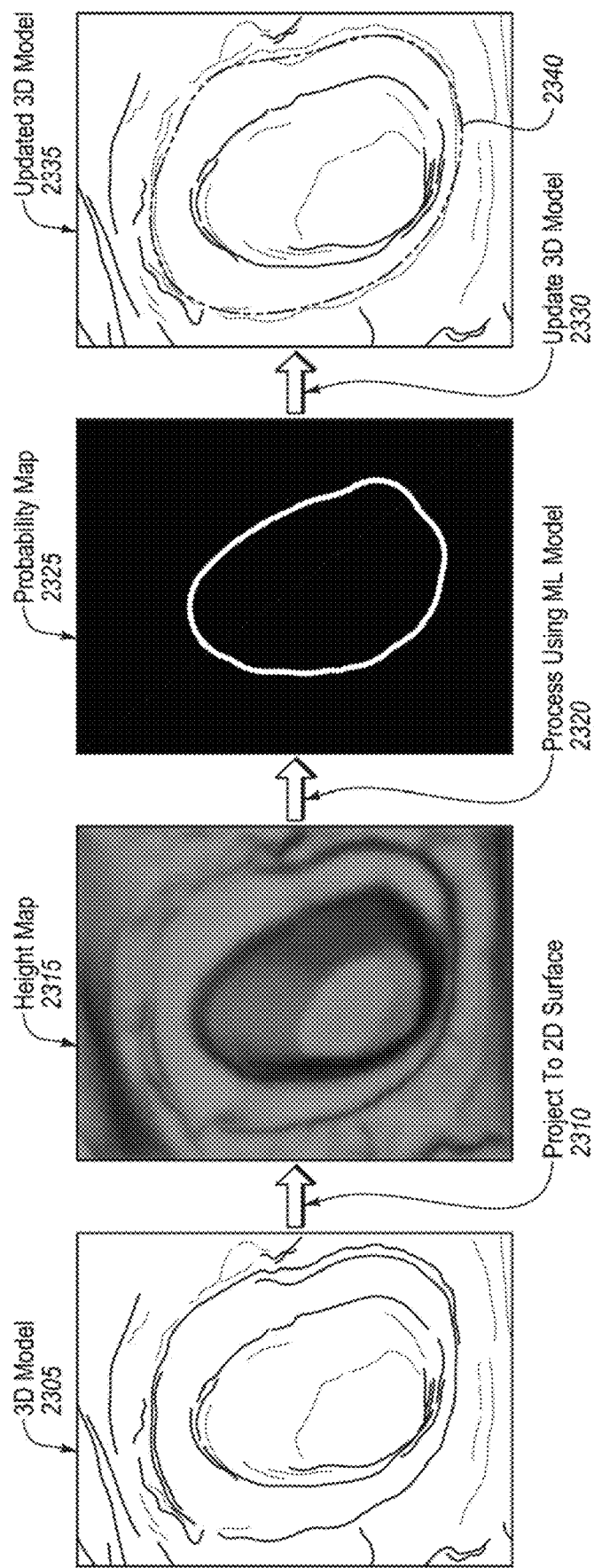
FIG. 23 illustrates an example of marking of a margin line in a 3D model of a preparation tooth, in accordance with an embodiment.

FIG. 23 illustrates marking of a margin line in a 3D model of a preparation tooth, in accordance with an embodiment. As shown, a 3D model of a dental site 2305 is projected 2310 onto a 2D surface to form a height map 2315, where the height map is a greyscale image that comprises a depth or height value for each pixel. The height map 2315 is then processed 2320 using a machine learning model that has been trained to identify margin lines in height maps. The ML model outputs a probability map 2325, where each pixel in the probability map corresponds to a pixel in the height map 2315 and represents a probability that the pixel in the height map 2315 represents a margin line. In one embodiment, the probability map 2325 is a mask. The probability map 2325 is then projected back onto the 3D model 2305 using the height data from the height map 2315. The probability information may be expressed as a texture on the 3D model. The probability information may then be used to draw the margin line 2340 in the 3D model 2305, resulting in updated 3D model 2335.

Figure 24A:
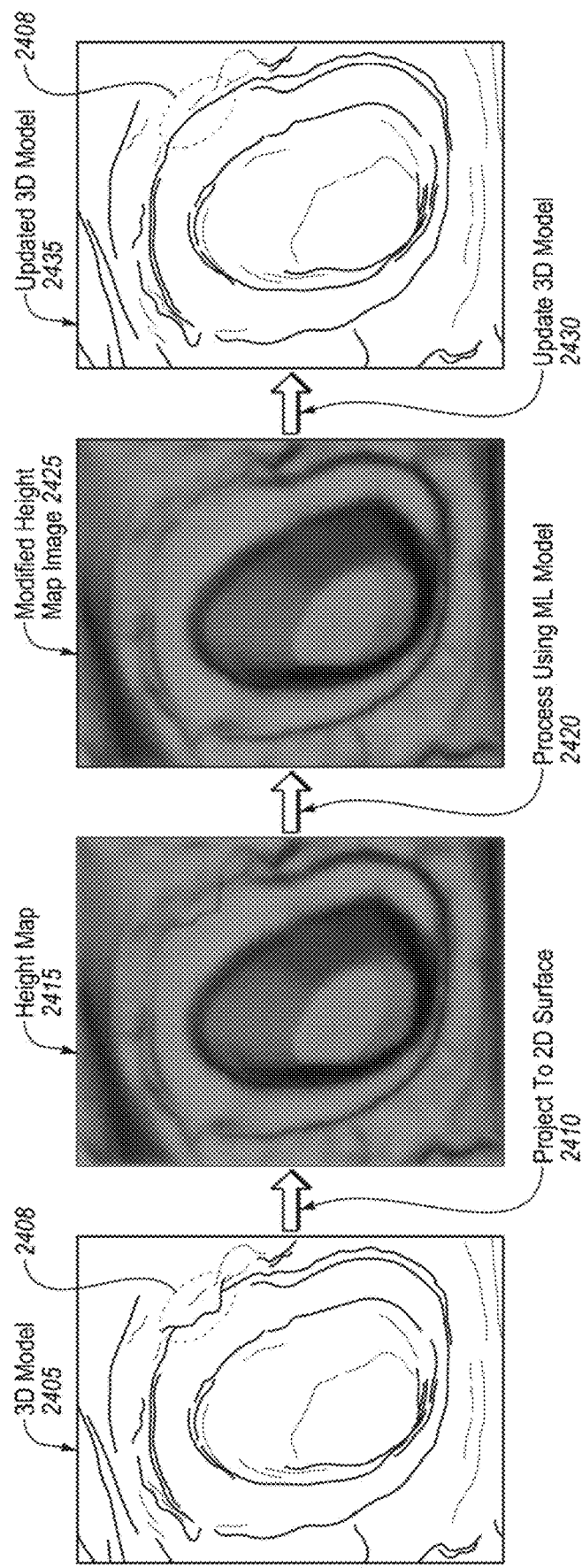
FIG. 24A illustrates a first example of automated correction of a 3D model of a tooth, in accordance with an embodiment.

FIG. 24A illustrates a first example of automated correction of a 3D model of a tooth, in accordance with an embodiment. As shown, a 3D model of a dental site 2405 is projected 2410 onto a 2D surface to form a height map 2415. In the 3D model of the dental site 2405, a region 2408 has soft tissue covering a portion of a margin line. The height map 2415 is the processed 2420 using a machine learning model that has been trained to modify images of preparation teeth in a manner that clarifies and/or improves a margin line in the images. The ML model outputs a modified height map 2425 that may have a same number of pixels as the height map 2415. The modified height map 2435 includes a cleaned up surface and/or margin line. The modified height map 2435 is then projected back onto the 3D model 2405, and data from the modified image 2435 is used to overwrite a portion of the 3D model. As shown, the region 2408 in the updated 3D model 2435 has a cleaned up margin line. In some embodiments, in addition to the modified height map, the machine learning model also outputs a probability map, where each pixel in the probability map indicates a probability of the pixel representing a margin line. In one embodiment, the probability map is a binary mask, where each pixel either has a value of 1 (100% probability) or a value of 0 (0% probability). In one embodiment, the modified height map includes a labeled margin line. For example, pixels in the modified height map that represent a margin line may include a particular flag or value. The updated 3D model 2435 may therefore include a drawn margin line determined from the probability map or other margin line indicators output by the machine learning model.

Figure 24B:
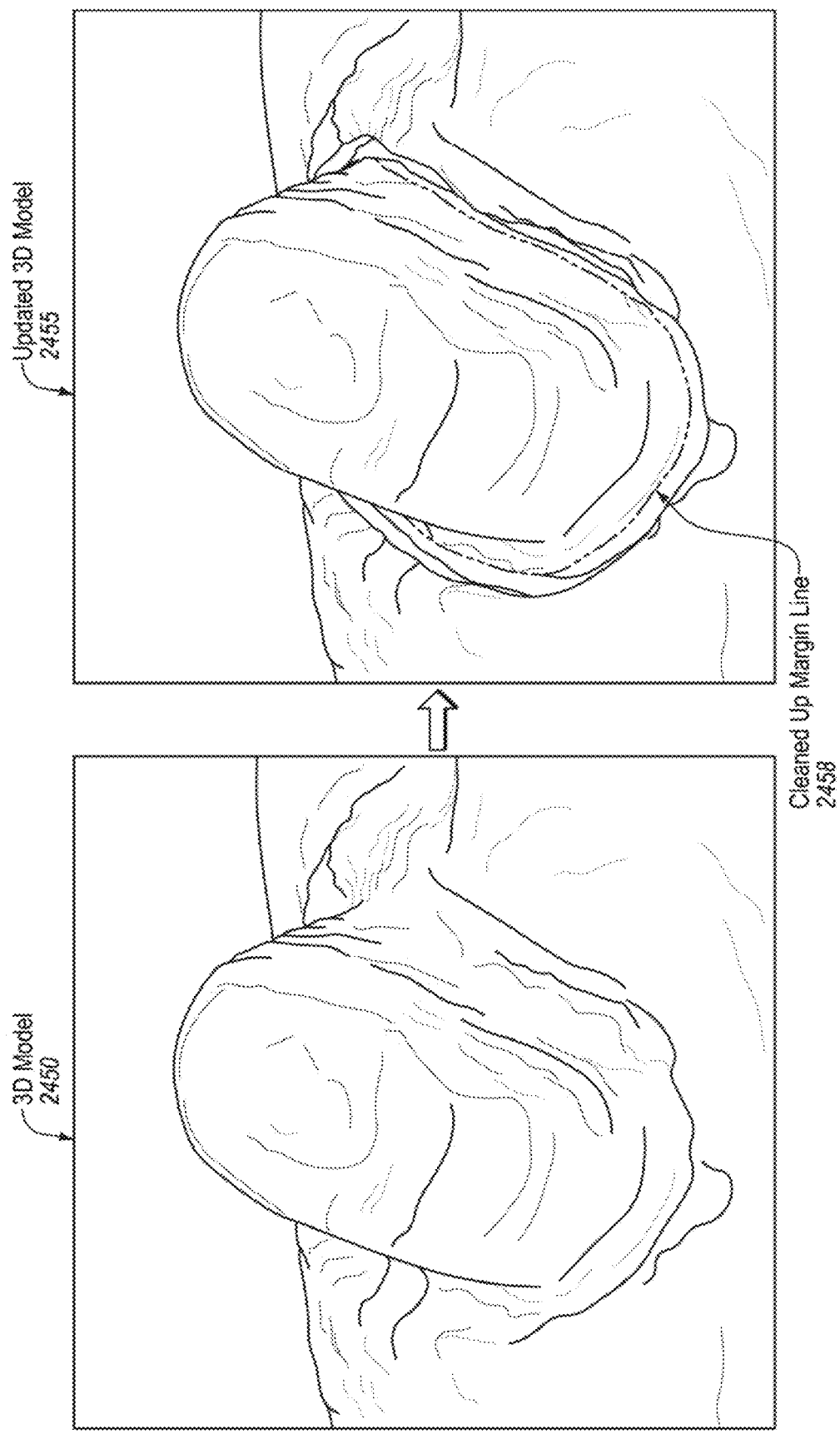
FIG. 24B illustrates a second example of automated correction of a 3D model of a tooth, in accordance with an embodiment.

FIG. 24B illustrates a second example of automated correction of a 3D model of a tooth, in accordance with an embodiment. As shown, a 3D model of a dental site 2450 is a starting 3D model. This 3D model may be projected onto a 2D surface to form a height map. The height map may be processed using a machine learning model that has been trained to a) modify images of preparation teeth in a manner that clarifies and/or improves a margin line in the images (e.g., cleans up the margin line) and that b) identifies the margin line. The ML model may output a modified height map that may have a same number of pixels as the input height map. The modified height map is then projected back onto the 3D model 2450, and data from the modified image is used to overwrite a portion of the 3D model to result in updated 3D model 2455. In one embodiment, the updated 3D model 2455 includes a labeled and cleaned up margin line 2458.

Figure 25:
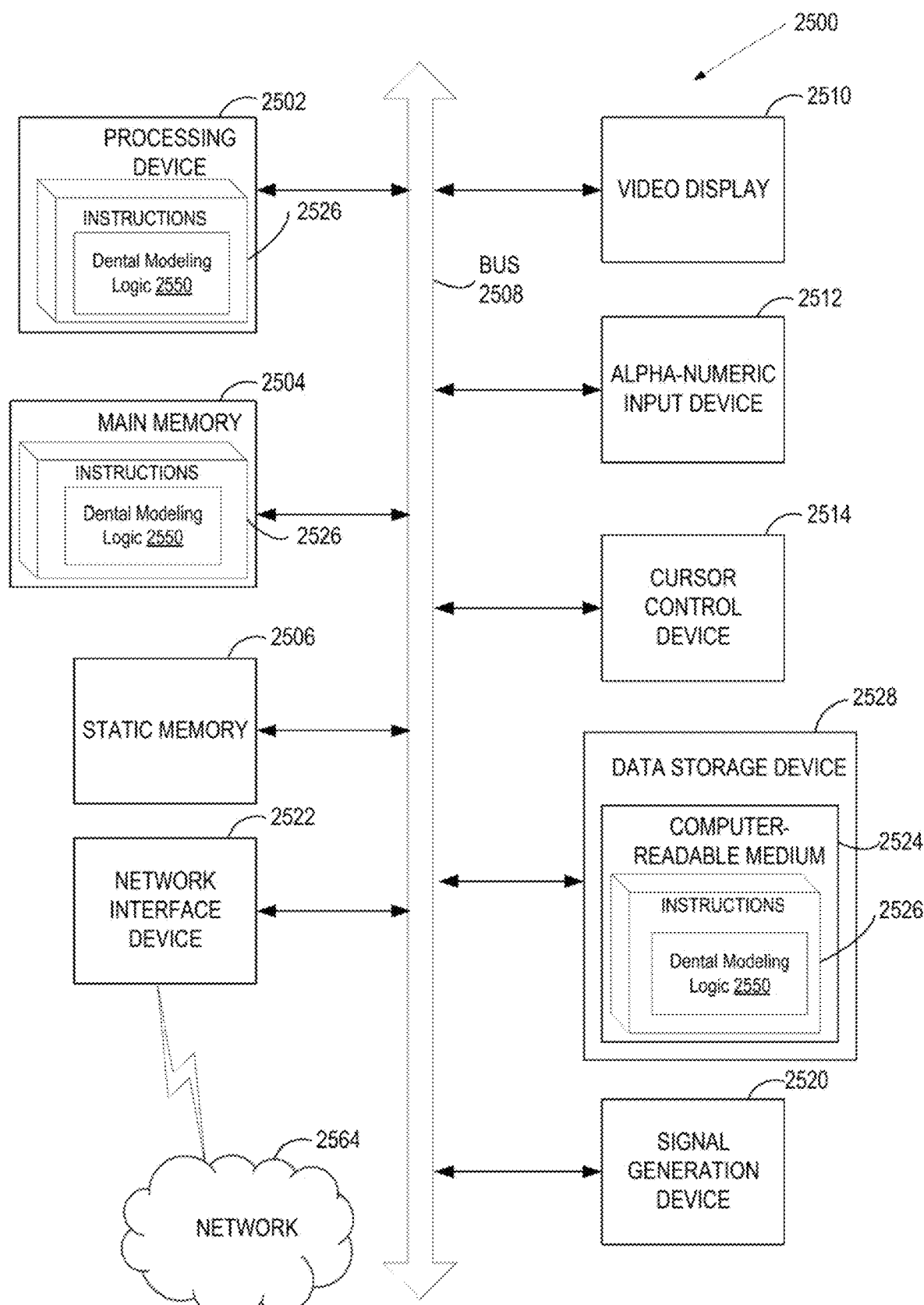
FIG. 25 illustrates a block diagram of an example computing device, in accordance with embodiments of the present disclosure.

FIG. 25 illustrates a diagrammatic representation of a machine in the example form of a computing device 2500 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The computing device 2500 may correspond, for example, to computing device 105 and/or computing device 106 of FIG. 1. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 2500 includes a processing device 2502, a main memory 2504 (e.g., read-only memory (ROM), flash memory, dynamic random access memory (DRAM) such as synchronous DRAM (SDRAM), etc.), a static memory 2506 (e.g., flash memory, static random access memory (SRAM), etc.), and a secondary memory (e.g., a data storage device 2528), which communicate with each other via a bus 2508.

Processing device 2502 represents one or more general-purpose processors such as a microprocessor, central processing unit, or the like. More particularly, the processing device 2502 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 2502 may also be one or more special-purpose processing devices such as an application specific integrated circuit (ASIC), a field programmable gate array (FPGA), a digital signal processor (DSP), network processor, or the like. Processing device 2502 is configured to execute the processing logic (instructions 2526) for performing operations and steps discussed herein.

The computing device 2500 may further include a network interface device 2522 for communicating with a network 2564. The computing device 2500 also may include a video display unit 2510 (e.g., a liquid crystal display (LCD) or a cathode ray tube (CRT)), an alphanumeric input device 2512 (e.g., a keyboard), a cursor control device 2514 (e.g., a mouse), and a signal generation device 2520 (e.g., a speaker).

The data storage device 2528 may include a machine-readable storage medium (or more specifically a non-transitory computer-readable storage medium) 2524 on which is stored one or more sets of instructions 2526 embodying any one or more of the methodologies or functions described herein, such as instructions for dental modeling logic 2550. A non-transitory storage medium refers to a storage medium other than a carrier wave. The instructions 2526 may also reside, completely or at least partially, within the main memory 2504 and/or within the processing device 2502 during execution thereof by the computer device 2500, the main memory 2504 and the processing device 2502 also constituting computer-readable storage media.

The computer-readable storage medium 2524 may also be used to store dental modeling logic 2550, which may include one or more machine learning modules, and which may perform the operations described herein above. The computer readable storage medium 2524 may also store a software library containing methods for the dental modeling logic 2550. While the computer-readable storage medium 2524 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. A non-transitory computer readable medium comprising instructions that, when executed by a processing device, cause the processing device to perform operations comprising:
   generating a three-dimensional model of a dental site from scan data of the dental site, the three-dimensional model comprising a representation of a preparation tooth;
   receiving or generating an image of the preparation tooth;
   processing data from the image using a trained machine learning model that has been trained to identify margin lines of preparation teeth, wherein the trained machine learning model outputs a probability map comprising, for each pixel in the image, a probability that the pixel depicts a margin line;
   determining, for each point of a plurality of points on the three-dimensional model that maps to a pixel in the image of the preparation tooth, a probability that the point depicts the margin line using the probability map;
   computing the margin line by applying a cost function to the plurality of points on the three-dimensional model based on probabilities associated with the plurality of points; and updating the three-dimensional model of the dental site by marking the margin line on the representation of the preparation tooth.

2. The non-transitory computer readable medium of claim 1, wherein the image of the preparation tooth is generated by projecting at least a portion of the three-dimensional model onto a two-dimensional surface.

3. The non-transitory computer readable medium of claim 1, wherein the scan data is intraoral scan data, and wherein the image of the preparation tooth is an intraoral image included in the intraoral scan data, and wherein the image comprises a height map.

4. The non-transitory computer readable medium of claim 1,
wherein the cost function selects points that together form a contour having a combined minimal cost, and wherein for each point a cost of the point is related to an inverse of the probability that the point depicts the margin line.

5. The non-transitory computer readable medium of claim 4, the operations further comprising:
determining whether the combined minimal cost exceeds a cost threshold; and
responsive to determining that the combined minimal cost exceeds the cost threshold, determining that the computed margin line has an unacceptable level of uncertainty.

6. The non-transitory computer readable medium of claim 4, the operations further comprising:
computing separate costs for different segments of the computed margin line;
determining that a segment of the computed margin line has a cost that exceeds a cost threshold; and
determining that the segment of the computed margin line has an unacceptable level of uncertainty.

7. The non-transitory computer readable medium of claim 6, the operations further comprising:
highlighting the segment of the computed margin line having the unacceptable level of uncertainty in the three-dimensional model.

8. The non-transitory computer readable medium of claim 6, the operations further comprising:
locking regions of the three-dimensional model comprising segments of the computed margin line having acceptable levels of uncertainty;
receiving a new intraoral image depicting the segment of the computed margin line with the unacceptable level of uncertainty; and
updating the three-dimensional model using the new intraoral image to output an updated three-dimensional model, wherein a first region comprising the segment of the computed margin line with the unacceptable level of uncertainty is replaced using information from the new intraoral image, and wherein locked regions of the three-dimensional model comprising the segments of the computed margin line having the acceptable levels of uncertainty are unchanged during the updating.

9. The non-transitory computer readable medium of claim 8, wherein the scan data comprises a plurality of blended images of the dental site, wherein each blended image of the plurality of blended images is based on a combination of a plurality of images, and wherein receiving the new intraoral image comprises:
accessing a plurality of individual intraoral images used to generate at least some of the plurality of blended images;
identifying a subset of the plurality of individual intraoral images that depict the segment of the computed margin line; and
selecting the new intraoral image from the subset of the plurality of individual intraoral images, wherein the new intraoral image comprises an improved depiction of the margin line as compared to the image of the preparation tooth.

10. The non-transitory computer readable medium of claim 9, the operations further comprising:
generating a plurality of different versions of the updated three-dimensional model, wherein each of the plurality of different versions is based on a different individual intraoral image from the subset of the plurality of individual intraoral images; and
receiving a user selection of a particular version of the updated three-dimensional model corresponding to the new intraoral image.

11. The non-transitory computer readable medium of claim 8, the operations further comprising:
generating a projected image of the first region by projecting at least a portion of the updated three-dimensional model onto an additional two-dimensional surface;
processing data from the projected image using the trained machine learning model, wherein the trained machine learning model outputs an additional probability map comprising, for each pixel in the projected image, a probability that the pixel depicts the margin line; and
further updating the updated three-dimensional model of the dental site by marking the margin line in the first region based on the additional probability map.

12. The non-transitory computer readable medium of claim 1, wherein the trained machine learning model further outputs an indication for at least a section of the margin line as to whether the section of the margin line depicted in the image is a high quality margin line or a low quality margin line.

13. The non-transitory computer readable medium of claim 1, the operations further comprising:
determining that the margin line is indeterminate in at least one section of the margin line associated with the image;
processing data from the image or a new image generated from the three-dimensional model using a second trained machine learning model that has been trained to modify images of teeth, wherein the second trained machine learning model outputs a modified image; and
updating the three-dimensional model of the dental site using the modified image, wherein an updated three-dimensional model comprises an updated margin line with an increased level of accuracy.

14. The non-transitory computer readable medium of claim 13, wherein the modified image comprises a plurality of pixels that are identified as part of the margin line.

15. The non-transitory computer readable medium of claim 13, wherein the image comprises a depiction of an interfering surface that obscures the margin line, wherein at least a portion of the depiction of the interfering surface is removed in the modified image, and wherein a portion of the margin line that was obscured in the image is shown in the modified image.

16. The non-transitory computer readable medium of claim 15, wherein the interfering surface comprises at least one of blood, saliva, soft tissue or a retraction material.

17. The non-transitory computer readable medium of claim 1, wherein the image is a monochrome image that contains height information, and wherein an input to the machine learning model comprises the data from the image and additional data from a two-dimensional color image that lacks height information.

18. A system comprising:
a memory; and
a computing device operatively connected to the memory, the computing device configured to:
generate a three-dimensional model of a dental site from scan data of the dental site, the three-dimensional model comprising a representation of a preparation tooth;
receive or generate an image of the preparation tooth;
process data from the image using a trained machine learning model that has been trained to identify margin lines of preparation teeth, wherein the trained machine learning model outputs a probability map comprising, for each pixel in the image, a probability that the pixel depicts a margin line;
determine, for each point of a plurality of points on the three-dimensional model that maps to a pixel in the image of the preparation tooth, a probability that the point depicts the margin line using the probability map;
compute the margin line by applying a cost function to the plurality of points on the three-dimensional model based on probabilities associated with the plurality of points; and
update the three-dimensional model of the dental site by marking the margin line on the representation of the preparation tooth.

19. The system of claim 18,
wherein the cost function selects points that together form a contour having a combined minimal cost, and wherein for each point a cost of the point is related to an inverse of the probability that the point depicts the margin line.

20. The system of claim 18, wherein the trained machine learning model is further to output an indication for at least a section of the margin line as to whether the section of the margin line depicted in the image is a high quality margin line or a low quality margin line.

* * * * *